United States Patent
Hauptmann et al.

(10) Patent No.: US 7,223,909 B2
(45) Date of Patent: May 29, 2007

(54) 4-KETOCAROTENOIDS IN FLOWER PETALS

(75) Inventors: Randal Hauptmann, Oswego, IL (US); Robert Eisenreich, North Aurora, IL (US); William Eschenfeldt, St. Charles, IL (US); Zubin Khambatta, Orland Park, IL (US)

(73) Assignee: Ball Horticultural, West Chicago, IL (US)

( * ) Notice: Subject to any disclaimer, the term of this patent is extended or adjusted under 35 U.S.C. 154(b) by 173 days.

(21) Appl. No.: 10/392,942

(22) Filed: Mar. 20, 2003

(65) Prior Publication Data

US 2004/0003430 A1 Jan. 1, 2004

Related U.S. Application Data

(63) Continuation-in-part of application No. 10/325,265, filed on Dec. 19, 2002, now Pat. No. 7,033,622.

(60) Provisional application No. 60/366,444, filed on Mar. 21, 2002.

(51) Int. Cl.
 C12N 15/52 (2006.01)
 C12N 15/63 (2006.01)
 C12N 15/82 (2006.01)
 A01H 5/02 (2006.01)

(52) U.S. Cl. .................. 800/323; 800/282; 800/287; 800/288; 800/298

(58) Field of Classification Search ............. 800/278, 800/282, 287, 288, 298, 323, 323.1; 536/23.1, 536/23.2, 23.7, 24.1
See application file for complete search history.

(56) References Cited

U.S. PATENT DOCUMENTS

| | | |
|---|---|---|
| 2,918,370 A | 12/1959 | Helgren |
| 4,670,247 A | 6/1987 | Scialpi |
| 5,043,170 A | 8/1991 | Borenstein et al. |
| 5,181,914 A | 1/1993 | Zook .................. 604/307 |
| 5,258,189 A | 11/1993 | Efstathiou |
| 5,270,063 A | 12/1993 | Wullschlefer et al. |
| 5,290,605 A | 3/1994 | Shapira |
| 5,308,759 A | 5/1994 | Gierhart |
| 5,382,714 A | 1/1995 | Khachik |
| 5,384,134 A | 1/1995 | Kross et al. .................. 424/661 |
| 5,427,783 A | 6/1995 | Gierhart |
| 5,605,699 A | 2/1997 | Bernhard et al. |
| 5,618,988 A | 4/1997 | Hauptmann et al. |
| 5,648,564 A | 7/1997 | Ausich et al. |
| 5,684,238 A | 11/1997 | Ausich et al. |
| 5,695,794 A | 12/1997 | Stark et al. |
| 5,747,544 A | 5/1998 | Garnett et al. |
| 5,811,273 A | 9/1998 | Misawa et al. |
| 5,827,652 A | 10/1998 | Garnett et al. |
| 5,849,345 A | 12/1998 | Giger et al. |
| 5,854,015 A | 12/1998 | Garnett et al. |
| 5,858,700 A | 1/1999 | Ausich et al. |
| 5,910,433 A | 6/1999 | Kajiwara et al. |
| 5,935,624 A | 8/1999 | DeLuca et al. |
| 5,955,102 A | 9/1999 | Gorenbein et al. |
| 5,965,795 A | 10/1999 | Hirschberg et al. |
| 5,972,690 A | 10/1999 | Misawa et al. |
| 6,056,962 A | 5/2000 | Kesharlial et al. |
| 6,150,130 A | 11/2000 | Misawa et al. |
| 6,191,293 B1 | 2/2001 | Levy |
| 6,218,436 B1 | 4/2001 | Howard et al. |
| 6,224,876 B1 | 5/2001 | Kesharlal et al. |
| 6,254,898 B1 | 7/2001 | Bragaglia |
| 6,329,432 B2 | 12/2001 | Howard et al. |
| 6,383,474 B1 | 5/2002 | Soudant et al. |
| RE38,009 E | 2/2003 | Garnett et al. |

FOREIGN PATENT DOCUMENTS

| | | |
|---|---|---|
| DE | 4020874 | 1/1991 |
| WO | WO 91/03571 | 3/1991 |
| WO | WO 92/16635 | 10/1992 |
| WO | WO 96/40092 | 12/1996 |
| WO | WO 98/18910 | 5/1998 |
| WO | WO 99/07867 | * 2/1999 |
| WO | WO 99/61652 | 12/1999 |
| WO | WO 00/32788 | 6/2000 |

OTHER PUBLICATIONS

Mann V. et al. Biotechnology; Aug. 2000, vol. 18 pp. 888-892.*
Misawa N. et al. J. of Bacteriology; Nov. 1995; p. 6575-6584.*
*Hortus Third A Concise Dictionary of Plants Cultivated in the United States and Canada*, MacMillan Publishing Company (1976).
W.I. Marusich et al., "Zeaxanthin as a Broiler Pigmenter", *Poultry Sci.*, 55:1486-1494 (1980).
Cetl et al, "Genetic and Cytogenetic Problems of *Tagetes* L. Breeding", *Folia Fac. Sci. Nat. Univ. Purkynianae Brun Biol.*, 21(1):5-56 (1985).

(Continued)

Primary Examiner—Russell P. Kallis
(74) Attorney, Agent, or Firm—Welsh & Katz, Ltd.

(57) ABSTRACT

The formation of a carotenoid compound containing a 4-keto-β-ionene ring such as astaxanthin or canthaxanthin in flowers, and particularly in the corolla and reproductive parts of a flower of a higher plant whose flowers produce a carotenoid compound containing a β-ionene ring such as β-carotene or zeaxanthin, but otherwise do not produce astaxanthin or canthaxanthin is disclosed. One or more genes controlled by a promoter are inserted (transformed) into a higher plant. The inserted gene encodes a chimeric enzyme including (a) a carotenoid-forming enzyme that is at least a ketolase. That gene is operatively linked to (b) a plastid-directed transit peptide. Some higher plants to be transformed produce at least zeaxanthin or β-carotene in their flowers prior to transformation, whereas other plants produce little if any colored carotenoid pigments prior to transformation and are transformed with a cassette of carotenoids-forming genes. Methods of transformation and use of the transformed plants are described.

18 Claims, 26 Drawing Sheets

OTHER PUBLICATIONS

Bone et al., "Preliminary Identification of the Human Macular Pigment", *Vision Res.*, 25(11):1531-1535 (1985).

Jyonouchi et al., "Studies of Immunomodulating Actions of Carotenoids. I. Effects of β-Carotene and Astaxanthin on Murine Lymphocyte Functions and Cell Surface Marker Expression in In Vitro Culture System", *Nutrition and Cancer*, 16(2):93-105 (1991).

Diaconu, "Utilization of Induced Variation in Breeding Pot Marigolds", *Agronomie*, 34(1):17-21 (1991).

Zaharia, et al., "Actiunea Radiathlor Gamma Asupra Germinatiei Si Biosintezei Pigmentilor Asimilatori Oa Unele Plante Floricole", *Seria Agricultura*, 44(1):107-114 (1991).

Tyczkowski et al., "Research Note: Preparation of Purified Lutein and Its Diesters from Extracts of Marigold (*Tagetes erecta*)", *Poultry Sci.*, 70(3):651-654 (1991).

Quackenbush et al., "Vitamins and Other Nutrients: Composition and Analysis of the Carotenoids in Marigold Petals", *J. Assoc. Off. Anal. Chem.*, 55(3):617-621 (1972).

Geetha et al., "Induced Chlorophyll and Viable Mutations in *Tagetes patula*L.", *Acta Botanica Indica*, 20(2):312-314 (1992).

Khachik et al., "Separation and Identification of Carotenoids and Their Oxidation Products in the Extracts of Human Plasma", *Anal. Chem.*, 64:2111-2122.

Jyonouchi et al., "Studies of Immunomodulating Actions of Carotenoids. II. Astaxanthin Enhances In Vitro Antibody Production to T-Dependent Antigens Without Facilitating Polyclonal B-Cell Activation", *Nutrition and Cancer*. 19(3):269-280 (1993).

Fray et al., "Identification and Genetic Analysis of Normal and Mutant Phytoene Synthase Genes of Tomato by Sequencing, Complementation and Co-Suppression", *Plant Mol. Biol.*, 22:589-602 (1993).

Bone et al., "Stereochemistry of the Human Macular Carotenoids," *Invest. Ophthalmol. Vis. Sci.*, 34(6):2033-2040 (1993).

Finnegan et al., "Transgene Inactivation: Plants Fight Back!", *Bio/Technology*, 12:883-888 (1994).

Tanaka et al., "Chemoprevention of Mouse Urinary Bladder Carcinogenesis by the Naturally Occurring Carotenoid Astaxanthin", *Carcinogenesis*, 15(1):15-19 (1994).

Seddon et al., "Dietary Carotenoids, Vitamins A, C, and E, and Advanced Age-Related Macular Degeneration", *JAMA*, 272(18):1413-1420 (1994).

Morris et al., "Serum Carotenoids and Coronary Heart Disease: The Lipid Research Clinics Coronary Primary Prevention Trial and Follow-Up Study", *JAMA*, 272(18):1439-1441 (1994).

Khachik et al., "Lutein, Lycopene, and Their Oxidative Metabolites in Chemoprevention of Cancer", *J. Cellular Biochem.*, 22:236-246 (1995).

Balnave et al., "Relative Efficiencies of Yellow Carotenoids for Egg Yolk Pigmentation", *AJAS*, 9(5):515-517 (1996).

Pogson et al., "Arabidopsis Carotenoid Mutants Demonstrate that Lutein is Not Essential for Photosynthesis in Higher Plants", *Plant Cell*, 8:1627-1639 (1996).

Bone et al., "Distribution of Lutein and Zeaxanthin Stereoisomers in the Human Retina", *Exp. Eye. Res.*, 64(2):211-218 (1997).

Khachik et al., "Identification, Quantification, and Relative Concentrations of Carotenoids and Their Metabolites in Human Milk and Serum," *Anal. Chem.*, 69:1873-1881.

Piccaglia et al., "Lutein and Lutein Ester Content in Different Types of Tagetes Patula and T. Erecta", *Ind. Crops and Prod.*, 8:45-51 (1998).

Moehs, et al., "Analysis of Carotenoid Biosynthesis Gene Expression During Marigold Petal Development", *Plant Mol. Biol.*, 45:281-293 (2001).

Bernstein et al., "Identification and Quantitation of Carotenoids and Their Metabolites in the Tissues of the Human Eye", *Exp. Eye Res.*, 72:215-223 (2001).

AOAC 1984, *Official Methods of Analysis* (14th Ed.), the Association of Official Analytical Chemists, Arlington, VA, USA.

Bone et al., "Analysis of the Macular Pigment by HPLC: Retinal Distribution and Age Study", *Invest. Ophthalmol. Vis. Sci.*, 29(6):843-849 (1998).

Giovannucci et al., "Intake of Carotenoids and Retinol in Relation to Risk of Prostate Cancer", *J. Nat. Cancer Inst.*, 87(23):1767-1776 (1995).

Datta, et al., "Short Communication: Gamma Ray-Induced Genetic Manipulations in Flower Colour and Shape in *Dendranthema grandiflorum* and Their Management Through Tissue Culture," *Plant Breeding*, 120:91-92 (2001).

Masakazu et al., "The Effects of Irradiating Gladiolus (Gladiolus X Grandiflora Hort.) Cormels with Gamma Rays on Callus Formation, Somatic Embryogenesis and Flower Color Variations in the Regenerated Plants", *J. Japanese Soc. Of Hort. Sci.*, 70(1):126-128 (2001).

Venkatachalam et al., "Effect of Gamma Rays on Some Qualitative and Quantitative Characters in Zinnia Elegans Jacq.", *Ind. J. Gen. & Plant Breeding*, 57(3):255-261 (1997).

Li et al., "A Fast Neutron Deletion Mutagenesis-Based Reverse Genetics System for Plants", *Plant Journal*, 27(3):235-242 (2001).

Love et al., "The Induction of Bud Sports in Coleus Blumei by Fast Neutrons", *Amer. Soc. Hort. Sci.*, 88:627-630 (1966).

Abe et al., *In Vitro Cell. & Dev. Bio.*, 38:93A (2002), Abstract P-1283.

Meyer et al., "Differences in DNA-Methylation are Associated With a Paramutation Phenomenon in Transgenic Petunia", *Plant Journal*, 4(1):89-100 (1993).

Napoli et al., "Introduction of a Chimeric Chalcone Synthase Gene into Petunia Results in Reversible Co-Suppression of Homologous Genes *in trans*", *Plant Cell*, 2:279-289 (1990).

Jorgensen et al., "Chalcone Synthase Cosuppression Phenotypes in Petunia Flowers: *Comparison of Sense* vs. *Antisense Constructs and Single-Copy* vs. *Complex T-DNA Sequences*", *Plant Mol. Biol.*, 31:957-973 (1996).

Hamilton et al. "A Species of Small Antisense RNA in Post-transcriptional Gene Silencing in Plants", *Science*, 286:950-952 (1999).

Metzlaff et al., "RNA-Mediated RNA Degradation and Chalcone Synthase A Silencing in Petunia", *Cell*, 88:845-854 (1997).

Chuang et al., "Specific and Heritable Genetic Infereference by Double-Stranded RNA in *Arabidopsis thaliana*", *PNAS*, 97(9):4985-4990.

Wesley et al., "Construct Design for Efficient, Effective and High-Throughput Gene Silencing in Plants", *Plant Journal*, 27(6):581-590 (2001).

Yang et al., "Ribozyme-Mediated High Resistance Against Potato Spindle Tuber Viroid in Transgenic Potatoes", *Proc. Natl. Acad. Sci.*, 94:4861-4865 (1997).

Miki et al., "Procedures for Introducing Foreign DNA into Plants", in *Methods in Plant Molecular Biology and Biotechnology*, Glick et al., Eds., CRC Press, Boca Raton, Florida, pp. 67-88 (1993).

Klein et al., "Transformation of Microbes, Plants and Animals by Particle Bombardment", *Bio/Technology*, 10:286-291 (1992).

Horsch et al., "A Simple and General Method for Transferring Genes into Plants", *Science*, 227:1229-1231 (1985).

Gruber et al., "Vectors for Plant Transformation", in *Methods in Plant Molecular Biology and Biotechnology*, Glick et al., Eds., CRC Press, Boca Raton, Florida, pp. 89-119 (1993).

Moloney et al., "High Efficiency Transformation of *Brassica napus* Using *Agrobacterium* Vectors", *Plant Cell Reports*, 8:238-242 (1989).

Lotan, et al., "Cloning and Expression in *Escherichia coli* of the Gene Encoding β-C-4-Oxygenase, that Converts β-Carotene to the Ketocarotenoid Canthaxanthin in *Haematococcus pluvialis*", *FEBS Letters*, 364:125-128 (1995).

Fraser, et al., "Enzymic Confirmation of Reactions Involved in Routes to Astaxanthin Formation, Elucidated Using a Direct Substrate in Vitro Assay", *Eur. J. Biochem.*, 252:229-236 (1998).

Misawa et al., "Elucidation of the Erwinia Uredovora Carotenoid Biosynthetic Pathway by Functional Analysis of Gene Products Expressed in *Escherichia coli*", *J. Bacteriology*, 172(12):6704-6712 (1990).

Misawa et al., "Production of β-Carotene in *Zymomonas mobilis* and *Agrobacterium tumefaciens* by Introduction of the Biosynthesis Genes from *Erwinia uredovora*", *Applied and Environmental Microbiology*, 57(6):1847-1849 (1991).

Mann et al., (Aug. 2000) *Nature Biotechnology* 18:888-892.
Harker et al., (1997) *FEBS Lett.* 404:129-134.
Giuliano et al., (1993) *The Plant Cell* 5:379-387.
Misawa et al. (Apr. 1995) *Biochem. Biophys. Res. Com.* 209(3):867-876.
Skreekala et al. (2003) *Theor. Appl. Genet.* 106:771-776 (published on line Oct. 30, 2002).
Comment, K. Esau, *Anatomy of Seed Plants*, John Wiley & Sons, 1977, p. 203, the cover of *Development*, (Nov. 2001) 128(22), The Company of Biologists Ltd.
Kajiwara, et al., *Plant Molecular Biology* 29:343-352 (1995).

Kajiwara, et al., "Isolation and functional identification of a novel cDNA for astaxanthin biosynthesis from *Hematococcus pluvialis*, and astaxanthin synthesis in *Escherichia coli*", *Plant Molecular Bio.*, 29: 343-352, 1995.
Mann, et al., "Metabolic engineering of astaxanthin production in tobacco flower", *Nature Biotechnology* vol. 18: 888-892 (Aug. 2000).
Harker, et al., "Biosynthesis of ketocarotenoids in transgenic cyanbacteria expressing the algal gene for β-C-4-oxygenase, *crtO*", *FEBS Letters* 404 129-134 (1997).

* cited by examiner

4-KETOCAROTENOIDS IN FLOWER PETALS

CROSS-REFERENCE TO RELATED APPLICATION

This application is a continuation-in-part of application Ser. No. 10/325,265, filed Dec. 19, 2002, now U.S. Pat. No. 7,033,622, and claims priority from U.S. provisional application Ser. No. 60/366,444 that was filed on Mar. 21, 2002.

FIELD OF INVENTION

The present invention relates to carotenoid biosynthesis and biotechnological production of astaxanthin. More specifically, this invention relates to the preferred expression in flowers, and particularly in the corolla and reproductive parts of a flower, e.g., the flower petals, of a gene that encodes an enzyme that converts a carotenoid compound containing a β-ionene ring such as β-carotene into a carotenoid compound containing a 4-keto-β-ionene ring so that the flower petal accumulates 4-keto-β-ionene ring-containing carotenoid compounds.

BACKGROUND ART

Carotenoids are natural pigments responsible for many of the yellow, orange and red colors seen in living organisms. Carotenoids are 40-carbon ($C_{40}$) terpenoids generally comprising eight isoprene ($C_5$) units joined together. Linking of the units is reversed at the center of the molecule. "Keto-carotenoid" is a general term for carotenoid pigments that contain a keto group in the ionene ring portion of the molecule, whereas "hydroxycarotenoid" refers to carotenoid pigments that contain a hydroxyl group in the ionene ring. Trivial names and abbreviations will be used throughout this disclosure, with IUPAC-recommended semi-systematic names usually being given in parentheses after first mention of a trivial name.

Carotenoids are synthesized from a five carbon atom metabolic precursor, isopentenyl pyrophosphate (IPP). There are at least two known biosynthetic pathways in the formation of IPP, the universal isoprene unit.

One pathway begins with mevalonic acid, the first specific precursor of terpenoids, formed from acetyl-CoA via HMG-CoA (3-hydroxy-3-methylglutaryl-CoA), that is itself converted to isopentenyl pyrophosphate (IPP). In this pathway, IPP condenses with its isomer dimethylallyl pyrophosphate (DMAPP) to produce geranyl pyrophosphate (GPP) that contains 10 carbon atoms. IPP condenses with GPP to produce farnesyl pyrophosphate (FPP) that contains 15 carbon atoms. FPP produces geranylgeranyl pyrophosphate (GGPP) with 20 carbon atoms by condensing with IPP again. Condensation of two GGPP molecules with each other produces colorless phytoene, which is the initial carotenoid.

Studies have also shown the existence of an alternative, mevalonate-independent pathway for IPP formation that was characterized initially in several species of eubacteria, a green alga, and in the plastids of higher plants. The first reaction in this alternative pathway is the transketolase-type condensation reaction of pyruvate and D-glyceraldehylde-3-phosphate to yield 1-deoxy-D-xylulose-5-phosphate (DXP) as an intermediate. The intermediate DXP is converted into 2-C-methyl-D-erythritol-4-phosphate that is thereafter converted into IPP. [See Harker et al., *FEBS Letters*, 448:115–119 (1999).]

Through a series of desaturation reactions, phytoene is converted to phytofluene, ζ-carotene, neurosporene and finally to lycopene. Subsequently, lycopene is converted by a cyclization reaction to β-carotene that contains two β-ionene rings. A keto-group and/or a hydroxyl group are introduced into each ring of β-carotene to thereby synthesize canthaxanthin, zeaxanthin, astaxanthin. [See Britton, Plant Pigments, Goodwin, T. W., ed., London, Academic Press, (1988), pp. 133–182; see also Misawa et al., *J. Bacteriol.*, 177:6575–6584 (1995).]

A hydroxylase enzyme has been shown to convert canthaxanthin to astaxanthin. Similarly, a ketolase enzyme has been shown to convert zeaxanthin to astaxanthin. The ketolase also converts β-carotene to canthaxanthin and the hydroxylase converts β-carotene to zeaxanthin. [See Kajiwara et al., *Plant Mol. Biol.*, 29:343–352 (1995); and Fraser et al., Eur. J. Biochem., 252:229–236 (1998).]

Findings from studies in *A. aurantiacum* and *E. uredovora* suggest that the gene(s) that code for the ketolase and hydroxylase are bifunctional in that each of those enzymes can bind and react at one β-ring, and then release the product and rebind, react and release a second product. There are several distinct biosynthesis pathways from β-carotene that can produce astaxanthin using only ketolase and hydroxylase enzymes for each conversion of the intermediary carotenoid. [See Misawa et al., *J. Bacteriol.*, 177:6575–6584 (1995).]

Canthaxanthin, whose structural formula is shown below, is a red xanthophyll carotenoid

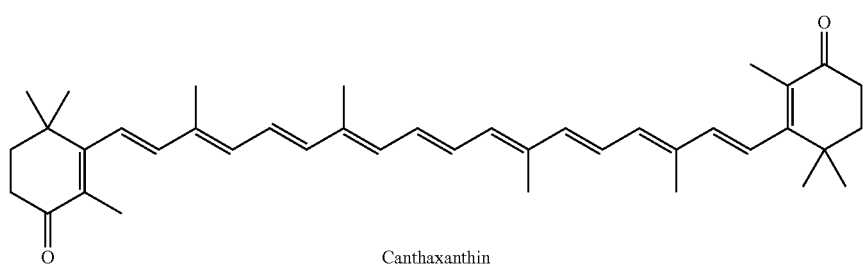

Canthaxanthin that normally does not occur in flower petals and is found in some mushrooms and in the feathers of flamingos. Canthaxanthin is used as a food coloring. It is also used as an oral suntan agent.

Astaxanthin, a red xanthophyll whose structural formula is shown below, is widely used as a pigmenting agent for cultured fishes and shellfishes. The complete biomedical properties of ods. However, when crustaceans such as a krill or the like are used, a great deal of work and expense are required for the isolation of astaxanthin from contaminants such as lipids and the like during the harvesting and extraction. Moreover, in the case of the cultured product of the yeast Phaffia, a great deal of expense is required for the gathering and extraction of astaxanthin because the yeast has rigid cell walls and produces astaxanthin only in a low yield.

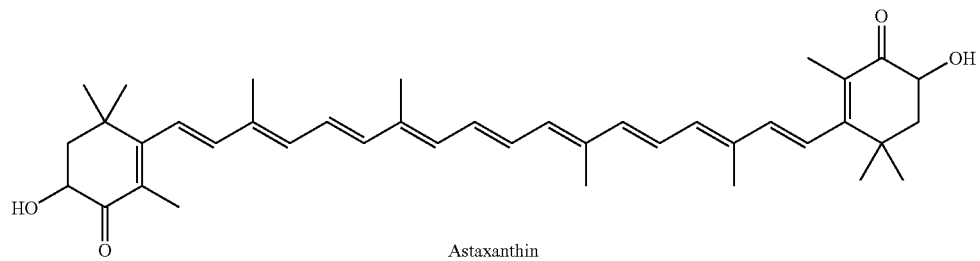

Astaxanthin astaxanthin remain to be elucidated, but initial results suggest that it could play an important role in cancer and tumor prevention, as well as eliciting a positive response from the immune system. [See Tanaka et al., *Carcinogenesis* 15(1): 15–19 (1994), Jyonouchi et al., *Nutrition and Cancer* 19(3): 269–280 (1993) and Jyonouchi et al., *Nutrition and Cancer* 16(2): 93–105 (1991).]

Astaxanthin is a carotenoid that occurs particularly in a wide variety of marine animals including fish such as salmonids and sea bream, and crustaceans such as crab, lobster, and shrimp. Because animals generally cannot biosynthesize carotenoids, they obtain those carotenoids present in microorganisms or plants upon which they feed. For this reason, astaxanthin has been widely used as a feed additive for the purpose of red color enhancement for cultured fish and shellfish such as sea bream, salmon, and shrimp and the like. Moreover, astaxanthin is attracting attention as an antioxidant to remove activated oxygen generated in a body, which is causative of a cancer. [See Matuno et al., *KAGAKU TO SEIBUTU* (Chemistry and Organisms), 28:219–227 (1990).]

Astaxanthin supplied from biological sources, such as crustaceans, yeast, and green alga is limited by low yield and costly extraction methods when compared with that obtained by organic synthetic methods. Usual synthetic methods, however, produce by-products that can be considered unacceptable. It is therefore desirable to find a relatively inexpensive source of (3S, 3'S)-astaxanthin to be used as a feed supplement in aquaculture and as a valuable chemical for other industrial uses.

Astaxanthin has been found to have diverse biological functions. It is a vitamin A precursor, acts as a scavenger and/or quencher of free radicals and active oxygen species, is seemingly a preventative against cancer and has been shown to enhance the immune response. [See Misawa et al., *J. Bacteriol.*, 177:6575–6584 (1995).] From studies of the properties of astaxanthin, it is a carotenoid of great interest to the pharmaceutical, "nutraceutical" (as a pre-cursor to vitamin A and other properties), and food industries.

Sources of astaxanthin include crustaceans such as a krill in the Antarctic Ocean, cultured products of the yeast *Phaffia*, cultured products of a green alga *Haematococcus pluvialis*, and products obtained by organic synthetic meth- Although *H. pluvialis* may produce one of the highest levels of astaxanthin (0.5–2 percent dry weight) among organisms, most of the astaxanthin synthesized by this alga is esterified. Such esterification may reduce its bioavilability to fish. Furthermore, *H. pluvialis* needs high light levels for astaxanthin formation.

For these reasons, astaxanthin produced from biological sources is deemed to be inferior to that obtained by the organic synthetic methods on the basis of cost. The organic synthetic methods however have a problem of by-products produced during the reactions in consideration of use of astaxanthin as a feed for fish and shellfish, and as an additive to foods. The products obtained by the organic synthetic methods can be contrary to some consumers' preference for naturally produced products. Thus, it would be desirable to supply an inexpensive astaxanthin that is free from contaminating side products and is produced from a biological source.

One approach to increase the productivity of astaxanthin or canthaxanthin production in a biological system is to use genetic engineering technology. Genes suitable for this conversion have been reported.

Ketolase (β-carotene ketolase or β-carotene oxygenase or just ketolase), as used herein, refers to the enzyme that causes a ketone (oxo) group to be added to the 4-position carbon atom of a carotenoid β-ionene ring to form various ketocarotenoid compounds in the later stages of the carotenoid biosynthesis pathway. There are several sources of genes that encode a ketolase enzyme that can convert carotenoid a β-ionene ring into a 4-keto-β-ionene ring that is present in canthaxanthin and astaxanthin.

For example, Misawa et al. (See, U.S. Pat. No. 6,150,130) specified DNA sequences including one isolated from the marine bacteria *Agrobacterium aurantiacum* sp. nov. MK1 or *Alcaligenes* sp. PC-1 that encodes a gene, referred to as crtW, used in the production of astaxanthin from a carotenoid β-ionene ring compound as a substrate by way of 4-ketozeaxanthin. Cunningham (See, WO 99/61652) reported isolation of a DNA that encodes a protein having ketolase enzyme activity from *Adonis aestivalis*, a plant species having deep red flower color due in part to the accumulation of the ketocarotenoid astaxanthin.

Two different genes that can convert a carotenoid β-ionene ring compound into astaxanthin have been isolated from the green alga *Haematococcus pluvialis*. The cloned cDNAs were shown to encode different β-carotene ketolase enzymes that convert a β-ionene ring methylene group to a β-ionene ring keto group (thus acting as a "ketolase").

One gene product has been designated as bkt by the first group to report its isolation encodes a polypeptide having a beta-C-4-oxygenase activity for the production of (3S,3'S)-astaxanthin from a host microorganism or a plant. [See Kajiwara et al., *Plant Molecular Biology*, 29:343–352 (1995); and Kajiwara et al. U.S. Pat. No. 5,910,433.] The second astaxanthin-forming gene and its translation product are referred to as crtO by the researchers that isolated the gene that encodes an enzyme that synthesizes astaxanthin. [See Harker et al., *FEBS Letters*, 404:129–134 (1997) and Lotan et al., *FEBS Letters*, 364:125–128 (1995); and Hirschberg et al. U.S. Pat. No. 5,965,795.] The crtO cDNA of the Hirschberg group had sequence identity of approximately 75–76 percent with the bkt gene of the Kajiwara group. The protein product of the crtO gene had a sequence identity of approximately 78 percent of that encoded by the bkt gene. The Lotan et al. paper reported a negative result in trying to transform zeaxanathin expressed in *E. coli* with the product of the crtO gene of *H. pluvialis*.

Genes that encode enzymes that can form astaxanthin from a carotenoid β-ionene ring compound such as zeaxanthin or β-carotene were also found in the marine bacteria *Agrobacterium aurantiacum* and Alcaligenes PC-1. These genes and their enzyme products, called crtW, exhibit about 75 percent identity to each other and about 37 percent homology to the bkt gene product of the *H. pluvialis*. The three β-carotene ketolases have four highly conserved regions. [See Kajiwara et al., *Plant Mol. Biol.*, 29:343–352 (1995); and also Misawa et al. U.S. Pat. No. 5,811,273 and No. 5,972,690.]

The term "hydroxylase" as used herein, refers to the gene or encoded enzyme that causes a hydroxyl group to be added to a carbon atom at the 3-position of a carotenoid β-ionene ring to form zeaxanthin or another hydroxylated intermediate in the later stages of the carotenoid biosynthesis pathway. More specifically, a contemplated hydroxylase (or β-carotene hydroxylase) is an enzyme that converts β-carotene or a 4-keto-β-carotene into one or more compounds that are hydroxylated at the 3-positon of the β-ring.

Different sources encoding a hydroxylase enzyme that converts carotenoid a β-ionene ring into a 3-hydroxy-β-ionene ring has been identified. The crtZ gene of *Erwinia uredovora* encodes one such hydroxylase. [See Kajiwara et al., *Plant Mol. Biol.*, 29:343–352 (1995).] A suitable hydroxylase is also encoded by the crtz gene of *Erwinia herbicola*. [See Ausich et. al., U.S. Pat. No. 5,684,238 (1997).]

A carotenoid biosynthesis gene cluster was identified in astaxanthin-producing bacteria, *Agrobacterium aurantiacum*. A crtz gene from that cluster was identified as coding for β-carotene hydroxylase. [See Misawa et al., *J. Bacteriol.*, 177:6575–6584 (1995).] In the Misawa et al. disclosure, *A. aurantiacum* crtZ gene was introduced to an *E. coli* transformant that accumulated all-trans-β-carotene. The transformant so formed produced zeaxanthin.

Although the experimental data did not demonstrate the ultimate production of astaxanthin, those data did demonstrate that the *Agrobacterium aurantiacum* crtZ gene encoded a hydroxylase. Because *A. aurantiacum* is an astaxanthin-producer, it is inferred that the hydroxylase, demonstrated to be bi-functional, converts canthaxanthin to astaxanthin. At minimum, this hydroxylase converts β-carotene to zeaxanthin, an intermediary in the carotenoid biosynthesis pathway from β-carotene into astaxanthin.

Furthermore, a crtZ gene having about a 90 percent identity to the crtZ gene of *A. aurantiacum* has been identified in *Alcaligenes* sp. strain PC-1. The function of the crtZ in *A. aurantiacum* and in the *Erwinia* family is as a hydroxylase. [See Misawa, "*J. Bacteriol.*, 177:6575–6584 (1995).]

A carotenoid biosynthesis gene cluster for the production of astaxanthin has been isolated from *A. aurantiacum*. The five-carotenogenic genes with the same orientation that were found in this cluster, have been designated crtW, crtZ, crtY, crtI, and crtB respectively. The stop codons of the individual crt genes, with the exception of crtB, overlapped with the start codons of the following crt genes. [See Misawa, "*J. Bacteriol.*, 177:6575–6584 (1995).] DNA sequences of *A. aurantiacum* and Alcaligenes sp. strain PC-1 for the crtW, crtZ and crtY genes that encode a ketolase, hydroxylase and lycopene cyclase enzyme are disclosed in U.S. Pat. No. 5,811,273 and No. 5,972,690.

A gene cluster encoding the enzymes for a carotenoid biosynthesis pathway has been also cloned from the purple photosynthetic bacterium *Rhodobacter capsulatus*. [See Armstrong et al., *Mol. Gen. Genet.*, 216:254–268 (1989).]

A similar cluster for carotenoid biosynthesis from ubiquitous precursors such as farnesyl pyrophosphate and geranyl pyrophosphate has been cloned from the non-photosynthetic bacteria *Erwinia herbicola*. The members of the gene cluster identified from *E. herbicola* include genes referred to as encoding GGPP synthase, phytoene synthase, phytoene dehydrogenase (4H), lycopene cyclase, and β-carotene hydroxylase genes. [See Ausich et al. U.S. Pat. No. 5,684,238; Sandmann et al., *FEMS Microbiol. Lett.*, 71:77–82 (1990); Hundle et al., *Photochem. Photobiol.*, 54:89–93 (1991); and Schnurr et al., *FEMS Microbiol. Lett.* 78:157–162(1991).]

Yet another carotenoid biosynthesis gene cluster has been cloned from *Erwinia uredovora*. In *E. uredovora*, these genes have been identified as crtE, crtB, crtI, and crtZ. [See Misawa et al. U.S. Pat. No. 5,429,939; and Misawa et al., *J. Bacteriol.*, 172:6704–6712 (1990).]

In the *Erwinia* and *Rhodobacter* species, crtE encodes GGPP synthase. CrtE, however, is absent in *A. aurantiacum*. Although the initial substrates of the enzymes encoded in the above gene clusters differ between species, it is the latter crt genes that have been demonstrated to play a significant role in the production of astaxanthin from the carotenoid precursor present. The production of astaxanthin in the marine *Agrobacteria* suggests that crtW and crtZ gene products, as identified in the various species, are primarily responsible for the conversion of β-carotene to astaxanthin via ketocarotenoid intermediates. [See Misawa et al., *J. Bacteriol.*, 177:6575–6584 (1995).]

The studies reported in Fraser et al., *Eur. J. Biochem.*, 252:229–236 (1998) indicate that β-carotene is the preferred substrate as compared to zeaxanthin for the *A. aurantiacum* ketolase and other possible oxygenated β-carotene derivatives when studied in an in vitro environment. Those authors also reported a less pronounced preference by the *A. aurantiacum* hydroxylase enzyme for a compound that contained a hydroxyl group on one ring and a keto group on the other (3-hydroxyechinenone) as compared to β-carotene or other oxygenated β-carotene derivatives. It is unknown and unpredictable as to whether the observed in vitro substrate preferences apply in vivo in *A. aurantiacum* or in a plant transformed with genes for those enzymes. It is also unknown and unpredictable as to whether enzymes encoded by other organisms behave similarly to that of *A. aurantiacum* in vitro or in vivo after transformation into the cells of a higher plant.

In many plants, lycopene is a branch point in carotenoid biosynthesis. Thus, some of the plant's lycopene is made into beta-carotene and zeaxanthin, and sometimes zeaxanthin diglucoside, whereas remaining portions of lycopene are formed into alpha-carotene and lutein (3,3'-dihydroxy-α-carotene), another hydroxylated compound.

Carotenoids in higher plants; i.e., angiosperms, are found in plastids; i.e., chloroplasts and chromoplasts. Plastids are intracellular storage bodies that differ from vacuoles in being surrounded by a double membrane rather than a single membrane. Plastids such as chloroplasts can also contain their own DNA and ribosomes, can reproduce independently and synthesize some of their own proteins. Plastids thus share several characteristics of mitochondria.

In leaves, carotenoids are usually present in the grana of chloroplasts where they provide a photoprotective function. Beta-carotene and lutein are the predominant carotenoids, with the epoxidized carotenoids violaxanthin and neoxanthin being present in smaller amounts. Carotenoids accumulate in developing chromoplasts of flower petals, usually with the disappearance of chlorophyll. As in flower petals, carotenoids appear in fruit chromoplasts as they develop from chloroplasts.

In a typical biosynthesis pathway for the production of β-carotene, enzymes convert geranylgeranyl pyrophosphate of the central isoprenoid pathway through phytoene and lycopene to β-carotene. Zeaxanthin, canthaxanthin and astaxanthin are among the xanthophylls that arise from β-carotene. Most enzymes that take part in conversion of phytoene to carotenes and xanthophylls are labile, membrane-associated proteins that lose activity upon solubilization. [See Breyer et al., *Eur. J. Biochem.*, 153:341–346 (1985); see also Hirschberg et al. U.S. Pat. No. 5,965,795 (1999)].

At the present time only a few plants are widely used for commercial colored carotenoid production. However, the productivity of colored carotenoid synthesis in most of these plants is relatively low and the resulting carotenoids are expensively produced. In addition, canthaxanthin and astaxanthin are not carotenoids that are so produced.

Hirschberg et al. U.S. Pat. No. 5,965,795 teaches that astaxanthin could be produced in the nectaries of transgenic tobacco plants. Those transgenic plants were prepared by *Argobacterium tumifaciens*-mediated transformation of tobacco plants using a vector that contained a ketolase-encoding gene from *H. pluvialis* denominated crtO along with the Pds gene from tomato as the promoter and to encode a leader sequence. The Pds gene was said by those workers to direct transcription and expression in chloroplasts and/or chromoplast-containing tissues of plants.

Results from that transformation indicated the production of five ketone-containing carotenoids, including astaxanthin in the nectary. Those results indicated that about 75 percent of the carotenoids found in the flower of the transformed plant contained a keto group. However, no evidence was presented as to the quantity of initial carotenoid present in the flower, nor about the about the amount of total carotenoid actually produced, nor about the production of carotenoids in the petals or reproductive parts of the flower.

The *Tagetes* genus is a member of the plant family Compositae, alternatively known as Asteraceae, and comprises some thirty species of strongly scented annual or perennial herbs. *Tagetes* are native from Arizona and New Mexico to Argentina. [See *Hortus Third A Concise Dictionary of Plants Cultivated in the United States and Canada*, MacMillan Publishing Company, New York (1976).] Cultivated genera include *Tagetes erecta*, commonly referred to as African marigold, *Tagetes patula*, commonly referred to as French marigold, *Tagetes erecta* x *patula*, commonly referred to as Triploid marigolds, and *Tagetes tenuifolia*, also known as *Tagetes signata* or signet marigold.

A marigold inflorescence is a solitary head comprised of a dense cluster of several hundred sessile or subsessile small flowers also known as florets. Marigolds have radiate flower heads with outer ray florets that are ligulate or strap-shaped around the central tubular-shaped disk florets. Some forms of marigold flower heads have most of their disk flowers transformed into ray flowers and contain few, if any, disk flowers. Such flower heads are referred to as double-flowered.

The ray flowers or florets are often referred to as petals by lay persons who may also refer to the flower heads as flowers. For ease of understanding, marigold flower heads will be referred to herein as flowers or flower heads, whereas the flower head-component flowers or florets, stamens, and pistils will be referred to as petals.

Cultivated marigolds possess showy flowers and are useful for ornamental purposes. In addition, the genus is recognized as a source for natural color, essential oils, and thiophenes. Dried marigold petals and marigold petal concentrates obtained from so-called xanthophyll marigolds are used as feed additives in the poultry industry to intensify the yellow color of egg yolks and broiler skin. [See Piccalia et al., *Ind. Crops and Prod.*, 8:45–51 (1998).] The carotenoids desired in poultry tissues are a function of their dietary concentration, because poultry do not have the ability to synthesize carotenoids de novo. [See Balnave et al., *Asian-Australiasian J. Animal Sci.*, 9(5): 515–517 (1996).]

The pigmenting ability of marigold petal meal resides largely in the carotenoid fraction known as the xanthophylls, primarily lutein esters. [See Piccalia et al., *Ind. Crops and Prod.*, 8:45–51 (1998)]. The xanthophyll zeaxanthin, also found in marigold petals, has been shown to be effective as a broiler pigmenter, producing a highly acceptable yellow to yellow-orange color [See Marusich et al., *Poultry Sci.*, 55:1486–1494 (1976)]. Of the xanthophylls, the pigments lutein and zeaxanthin are the most abundant in commercially available hybrids. Structural formulas for lutein and zeaxanthin are shown below.

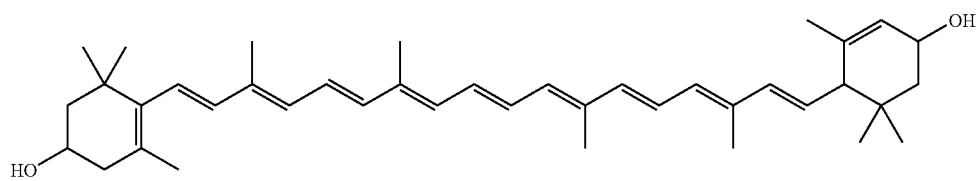

Lutein

-continued

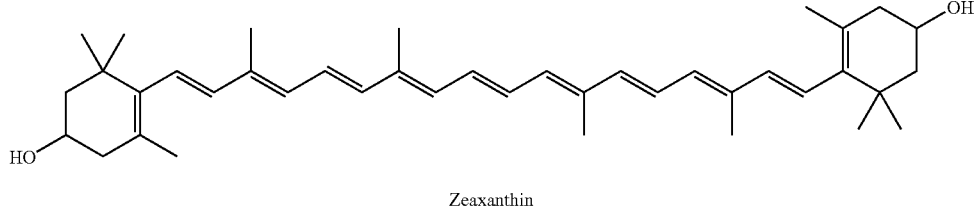

Zeaxanthin

Each lutein and zeaxanthin terminal ring structure contains one hydroxyl group, so that each molecule contains two hydroxyl groups. Lutein is believed to be biologically produced by two separate hydroxylations of α-carotene, whereas zeaxanthin is believed to be biologically produced by two separate hydroxylations of β-carotene. Both α-carotene and β-carotene are understood to be formed by the action of appropriate cyclase enzymes on δ-carotene and γ-carotene, respectively, which are formed by cyclization of lycopene. Lycopene, δ-carotene, γ-carotene, (α-carotene and β-carotene are each hydrocarbon carotenoids, and with their 40-carbon precursors are referred to as carotenes. Oxygenated carotenoids such as lutein, zeaxanthin, astaxanthin and violaxanthin are referred to as xanthophylls.

FIG. 1 shows a schematic representation of the biological synthesis pathway for the production of lutein and zeaxanthin and later products from phytoene, the first $C_{40}$ carotenoid in the pathway. Lutein and zeaxanthin are present in marigold petals primarily as mono- and dβ-esters of fatty acids. FIG. 1 also notes epoxide-containing later products that can arise from zeaxanthin, of which violaxanthin is an intermediate in the abscisic acid synthetic pathway.

Carotenoids have been found in various higher plants in storage organs and in flower petals. For example, marigold flower petals accumulate large quantities of esterified lutein as their predominant xanthophyll carotenoid (about 75 to more than 90 percent), with smaller amounts of esterified zeaxanthin. Besides lutein and zeaxanthin, marigold flower petals also typically exhibit a small accumulation of β-carotene and epoxidized xanthophylls, but do not produce or accumulate canthaxanthin or astaxanthin because a 4-keto-β-ionene ring-forming enzyme is absent in naturally-occurring marigolds or their hybrids.

Xanthophyll marigolds differ in several characteristics from ornamental marigolds. First and foremost, xanthophyll marigolds are used as an extractable source for carotenoids and have plant habits that differ from ornamental marigolds. Ornamental marigolds typically grow only about 45 to about 60 cm from the ground, whereas xanthophyll marigolds grow to about 65 to about 70 cm from the ground. Xanthophyll marigolds grow in a bushier habit than do ornamental marigolds, and can be grown as row crops whereas ornamental marigolds typically cannot. Xanthophyll marigolds are typically dark orange in color, whereas ornamentals can be white, yellow, or orange in color, or can have mixed colors, including mahogany colors due to anthocyanin pigments that are less abundant in xanthophyll marigolds.

One way to increase the productive capacity of biosynthesis is to apply recombinant DNA technology. Thus, it would be desirable to produce colored carotenoids generally and, with the use of recent advances in determining carotenoid biosynthesis from β-carotene to canthaxanthin or astaxanthin, or both, to control the production of carotenoids, specifically canthaxanthin and astaxanthin. That type of production permits control over quality, quantity and selection of the most suitable and efficient producer organisms. The latter is especially important for commercial production economics and therefore availability to consumers.

It would be advantageous if a marigold or other plants were available whose flowers produced large amounts of β-carotene, canthaxanthin, zeaxanthin, or other astaxanthin precursors and small amounts or no lutein so that such plants could be transformed with one or more of an appropriate hydroxylase gene and an appropriate ketolase gene to produce astaxanthin from the flowers of the resulting transformants. The invention discussed hereinafter relates in some embodiments to such transformed plants, and particularly to transformed marigold plants.

BRIEF SUMMARY OF THE INVENTION

The present invention relates to the formation of a 4-keto-β-ionene compound such as canthaxanthin and astaxanthin in flowers, and particularly at least in the corolla and reproductive parts of a flower, e.g., the flower petals, of a transformed higher plant. One or more genes controlled by a promoter such as a flower petal-preferred promoter is inserted (transformed) into a higher plant. The inserted gene encodes a chimeric enzyme including (a) a carotenoid-forming enzyme that is a ketolase, a hydroxylase or both enzymes, operatively linked to (b) a plastid-directed transit peptide. The flower petals of such a minimally transformed plant produce and preferably accumulate at least β-carotene or zeaxanthin prior to transformation.

Astaxanthin is typically produced by double hydroxylation and double ketolation of each of the two β-rings of β-carotene, whereas canthaxanthin is believed to be produced by double ketolation of each of the two β-rings of β-carotene. Some higher plants produce and accumulate β-carotene or other astaxanthin precursors in their flower petals and can be transformed with one or both of the genes that encode β-ring ketolating and β-ring hydroxylating enzymes. Other higher plant petals contain insufficient quantities of Carotene or other appropriate carotenoid precursors and are transformed with one or more additional genes that encode the necessary enzyme(s) for astaxanthin production from the precursors present, including ubiquitous precursors such as geranyl pyrophosphate and farnesyl pyrophosphate.

One aspect contemplated by the present invention is a transformed higher plant (a transgenic plant) or a regenerable portion thereof, whose flowers and at least corolla or other reproductive flower parts produce and preferably accumulate a carotenoid compound having a 4-keto-β-ionene ring, and preferably a carotenoid compound that contains two β-ionene rings each of which itself contains a 4-keto group. That transgenic plant contains a heterologous genomic DNA segment (transgene) that (a) encodes a chimeric ketolase enzyme and (b) contains a promoter that controls expression of the chimeric enzyme. The chimeric ketolase enzyme is comprised of (i) a N-terminal first portion comprising a plastid transit peptide portion fused to (ii) a second, ketolase enzyme portion that converts carotenoid β-ionene rings into carotenoid 4-keto-β-ionene rings. The promoter and the plastid transit peptide are preferably from different species. The result of expression of the transgene in a contemplated plant is flower petal accumulation of carotenoid compounds that contain 4-keto-β-ionene rings such as echinenone, 3-hydroxyechinenone, 3'-hydroxyechinenone, canthaxanthin, adonirubuin, adonixanthin, and astaxanthin. In preferred practice in one embodiment, those carotenoid compounds also contain 3-hydroxyl groups in their β-ionene rings.

A contemplated plant in one embodiment is an $F_1$ hybrid or later generation hybrid of a transgenic plant, or a selfing of a transgenic plant. In one preferred embodiment, the plant is an $F_1$ hybrid. In one aspect of this embodiment, both parents of the hybrid are transgenic, whereas in another aspect of this embodiment, one parent is transgenic and the other is not. One or both parent plants can be mutant plants that exhibit abnormal expression of one or more carotenoid pigments; i.e. expression of a carotenoid pigment that is not usually present in the plant in isolatable amounts, or one or more usually found carotenoid pigments that are present in abnormally high amounts.

A marigold is one preferred host plant for transformation, as such plants normally produce carotenoid pigments that contain β-ionene rings such as β-carotene and zeaxanthin. A particularly preferred non-transformed mutant marigold host plant produces xanthophylls in its petals at about 4 to about 20 mg/g fresh weight, and is a mutant that exhibits a zeaxanthin ratio greater than about 1:10 and preferably greater than about 2:10. More preferably, at least about 70 percent, and most preferably at least about 90 percent, of the xanthophylls is zeaxanthin so that the ratio approaches 1 (one). Another non-transformed mutant marigold host exhibits a β-carotene ratio of greater than about 1:10, and preferably greater than about 2:10.

The pollen and an ovule of a transformed plant are separately contemplated. The regenerable portion of such a contemplated transformed plant includes cells selected from the group consisting of embryos, cotyledons, hypocotyls, meristems, pollen, leaves, anthers, roots, root tips, and flowers, or protoplasts or callus derived therefrom.

A further embodiment contemplates a seed that on planting in a suitable environment and growth to maturity yields a transgenic plant such as a transgenic marigold whose flower petals and reproductive parts accumulate a carotenoid pigment that contains one or more 4-keto-β-ionene rings such as echinenone, 3-hydroxyechinenone, 3'-hydroxyechinenone, canthaxanthin, adonirubuin, adonixanthin, and astaxanthin, whereas the flower petals of a non-transgenic plant of the same type does not accumulate such pigments.

A transgenic plant contemplated by this invention preferably accumulates a carotenoid 4-keto-β-ionene ring compound at least in flower petals, and can also accumulate such compounds in reproductive flower parts such as the stamen and the pistil, as well as other flower parts. A contemplated transgenic plant can, but preferably does not, accumulate a carotenoid 4-keto-β-ionene ring compound in sepals or nectaries, when present. It is further preferred that the carotenoid 4-keto-β-ionene ring compound be a carotenoid 4,4'-diketo-β-ionene ring compound such as canthaxanthin, adonirubuin and astaxanthin, and particularly astaxanthin or canthaxanthin. It is most preferred that β-carotene or zeaxanthin is the β-ionene ring compound produced in the non-transformed host plant flowers, and astaxanthin is the 4,4'-diketo-β-ionene ring compound that is accumulated in the transformed plant (transformant) flowers. It is also particularly preferred in other embodiments that canthaxanthin is the 4,4'-diketo-β-ionene ring compound that is accumulated in the transformed plant (transformant) flowers.

Flower parts such as petals that contain one or both of canthaxanthin and astaxanthin are also contemplated. The flower parts are typically present in comminuted form. A further aspect of this embodiment is transgenic marigold flower petals that contain one or more of echinenone, 3-hydroxyechinenone, 3'-hydroxyechinenone, canthaxanthin, adonirubuin, adonixanthin, and astaxanthin. The transgenic marigold flower petals are preferably in comminuted form.

A plant oleoresin comprised of one or both of canthaxanthin and fatty acid esters of astaxanthin is also contemplated. A composition suitable for use as a food supplement is also contemplated. The food supplement comprises one or both of canthaxanthin and fatty acid esters of astaxanthin dissolved or dispersed in a comestible medium. A hydrolyzed (saponified) oleoresin can also be used in a food supplement or nutraceutical that contains a carotenoid 4-keto-β-ionene ring compound that is free of esterified hydroxyl groups.

Another aspect contemplated by this invention relates to a purified and isolated DNA segment. That DNA segment encodes a chimeric ketolase enzyme polypeptide that itself contains (i) an N-terminal first portion comprising a plastid transit peptide portion fused to (ii) a second portion that is a ketolase enzyme that converts a carotenoid β-ionene ring into a 4-keto-β-ionene ring. That DNA includes (iii) a promoter that directs expression, and preferably directs flower petal-preferred expression, operatively linked to the sequence that encodes the chimeric ketolase enzyme polypeptide. Transformation of this DNA into a higher plant results in expression in flower parts of an enzyme that catalyzes the conversion of a carotenoid β-ionene ring into a carotenoid 4-keto-β-ionene ring so that a 4-keto-β-ionene ring-containing carotenoid compound is accumulated in a transformed plant that produced carotenoid compound containing a β-ionene ring. Illustrative 4-keto-β-ionene ring-containing carotenoid compounds include echinenone, 3-hydroxyechinenone, 3'-hydroxyechinenone, canthaxanthin, adonirubuin, adonixanthin, and astaxanthin.

Still another embodiment of this invention contemplates a transgenic plant whose flower parts such as the corolla or other reproductive flower parts produce a carotenoid compound having a 3-hydroxy-4-keto-β-ionene ring. That transgenic plant contains a genomic first transgene that encodes a chimeric ketolase enzyme polypeptide (as described above) and also a genomic second transgene that (a) encodes a chimeric hydroxylase enzyme polypeptide and (b) contains a promoter that directs expression, which is preferably flower petal-preferred, of the chimeric hydroxylase enzyme. That second encoded chimeric hydroxylase enzyme polypeptide contains (i) an N-terminal first portion comprising a plastid transit peptide portion fused to (ii) a second, hydroxylase enzyme portion that converts a carotenoid β-ionene ring into a 3-hydroxy-β-ionene ring. The promoter and the plastid transit peptide are again preferably from different species. The result of expression of the transgene in a contemplated plant is flower-preferred accumulation of a 3-hydroxy-4-keto-β-ionene ring carotenoid compound.

A transgenic plant contemplated by this aspect of the invention accumulates a 3-hydroxy-4-keto-β-ionene ring carotenoid compound in flower parts such as petals, and can also accumulate such compounds in reproductive flower parts such as the stamen and the pistil. A contemplated transgenic plant can, but preferably does not, accumulate a carotenoid 3-hydroxy-4-keto-β-ionene ring compound in sepals or nectaries, when present. Illustrative carotenoid compounds that have a 3-hydroxy- and a 4-keto group in the β-ionene ring include astaxanthin, adonixanthin, adonirubuin, 3-hydroxyechinenone and 3'-hydroxyechinenone. It is preferred that the carotenoid 3-hydroxy-4-keto-β-ionene ring compound be a carotenoid 3,3'-dihydroxy-4-keto-β-inoene ring compound such as astaxanthin or adonixanthin.

A preferred plastid transit peptide for either or both chimeric polypeptides is the RUBISCO transit peptide. A preferred promoter is the about 1 kb segment 5' upstream of the *Clarkia breweri* linalool synthase 1 (LIS1) gene, the ubiquitin 3 (UBQ3) promoter or the ubiquitin 11 (UBQ11) promoter of *Arabidopsis thaliana*. The LIS1 promoter is flower-petal preferred, whereas the UBQ3 and UBQ11 promoters are constitutive.

A preferred ketolase enzyme that converts a carotenoid β-ring into 4-keto-β-ring is that encoded by the bkt gene of *Haematococcus pluvialis,* that encoded by the crtO gene of *Haematococcus pluvialis,* the enzyme encoded by the crtW gene of *Agrobacterium aurantiacum* or the enzyme encoded by the crtW gene of Alcalignes sp.PC-1. The ketolase gene is often referred to hereinafter as the crtw gene for ease in discussion, regardless of the source of the gene sequence.

A preferred hydroxylase enzyme that converts a carotenoid β-ionene ring into a carotenoid 3-hydroxy-β-ionene ring is encoded by the crtZ gene of *Erwinia uredovora,* that encoded by the crtZ gene of *Erwinia herbicola,* the enzyme encoded by the crtZ gene of *Agrobacterium aurantiacum* or the enzyme encoded by the crtz gene of Alcalignes sp.PC-1.

A further embodiment of the invention contemplates a transgenic plant that includes genomic DNA that encodes a ketolase enzyme, a hydroxylase enzyme as before, and one or more additional carotenoid-forming transgenes. Each additional transgene expresses a chimeric polypeptide carotenoid-forming enzyme that contains an N-terminal plastid transit peptide portion and each gene is preferably operatively linked to a promoter that directs flower petal-preferred expression. The additional carotenoid-forming transgenes can be obtained from a number of sources that include the (a) crtE, crtB, crtI, crtY, and crtZ genes of *Erwinia uredovora* as defined in Misawa et al. U.S. Pat. No. 5,429,939, or (b) GGPP synthase, phytoene synthase, phytoene dehydrogenase (4H), lycopene cyclase, and β-carotene hydroxylase genes of *Erwinia herbicola* as defined in Ausich et al. U.S. Pat. No. 5,684,238.

The invention thus contemplates embodiments in which the β-carotene, or other carotenoid precursor compounds in the production of astaxanthin, is present in the flowers of the flowering plant chosen as the host (for example, marigolds). The invention also contemplates embodiments in which a host plant's flowers lack β-carotene or other carotenoid precursors, such as the vinca. In a plant of the latter type, the inserted DNA includes genes that code for carotenoid precursors (compounds that can be converted biologically into β-carotene) and a ketolase, as well as a hydroxylase, if otherwise absent.

Preferred flowering plants include, but are not limited to: Amaryllidaceae (*Allium, Narcissus*); Apocynaceae (*Catharanthus*); Asteraceae, alternatively Compositae (*Aster, Calendula, Callistephus, Cichorium, Coreopsis, Dahlia, Dendranthema, Gazania, Gerbera, Helianthus, Helichrysum, Lactuca, Rudbeckia, Tagetes, Zinnia*); Balsaminaceae (*Impatiens*); Begoniaceae (*Begonia*); Caryophyllaceae (*Dianthus*); Chenopodiaceae (*Beta, Spinacia*); Cucurbitaceae (*Citrullus, Curcurbita, Cucumis*); Cruciferae (*Alyssum, Brassica, Erysimum, Matthiola, Raphanus*); Gentinaceae (*Eustoma*); Geraniaceae (*Pelargonium*); Graminae, alternatively Poaceae, (*Avena, Horedum, Oryza, Panicum, Pennisetum, Poa, Saccharum, Secale, Sorghum, Triticum, Zea*); Euphorbiaceae (*Poinsettia*); Labiatae (*Salvia*); Leguminosae (*Glycine, Lathyrus, Medicago, Phaseolus, Pisum*); Liliaceae (*Lilium*); Lobeliaceae (*Lobelia*); Malvaceae (*Abelmoschus, Gossypium, Malva*); Plumbaginaceae (*Limonium*); Polemoniaceae (*Phlox*); Primulaceae (*Cyclamen*); Ranunculaceae (*Aconitum, Anemone, Aquilegia, Caltha, Delphinium, Ranunculus*); Rosaceae (*Rosa*); Rubiaceae (*Pentas*); Scrophulariaceae (*Angelonia, Antirrhinum, Torenia*); Solanaceae (*Capsicum, Lycopersicon, Nicotiana, Petunia, Solanum*); Umbelliferae (*Apium, Daucus, Pastinaca*); Verbenaceae (*Verbena, Lantana*); Violaceae (*Viola*).

BRIEF DESCRIPTION OF THE DRAWINGS

In the drawings forming a part of this disclosure.

*rium* Ti-DNA that encodes nopaline synthase (nos), and several important restriction enzyme sites and their position numbers.

Figure 6:
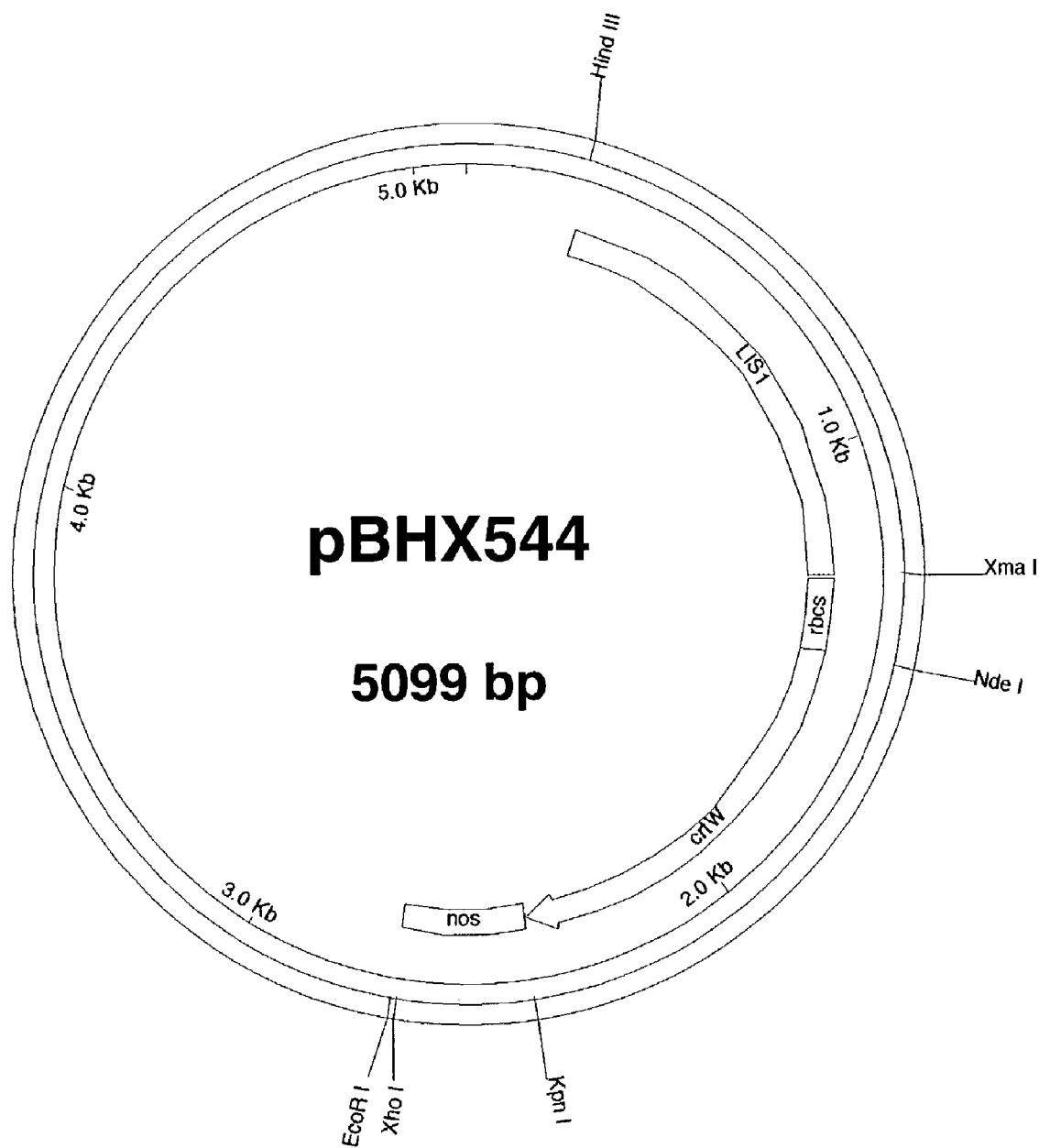

FIG. 6 schematically shows plasmid pBHX544 that contains an approximately 5099 base pair (bp) DNA segment that includes genes encoding the RUBISCO (RBCS)/ketolase (*Haematococcus pluvialis* crtW) chimeric polypeptide, as well as the promoter 5' upstream to the linalool synthase 1 gene (LIS1), the 3' termination sequence from *Agrobacterium* Ti-DNA that encodes nopaline synthase (nos), as well as several important restriction enzyme sites and their position numbers.

Figure 7:
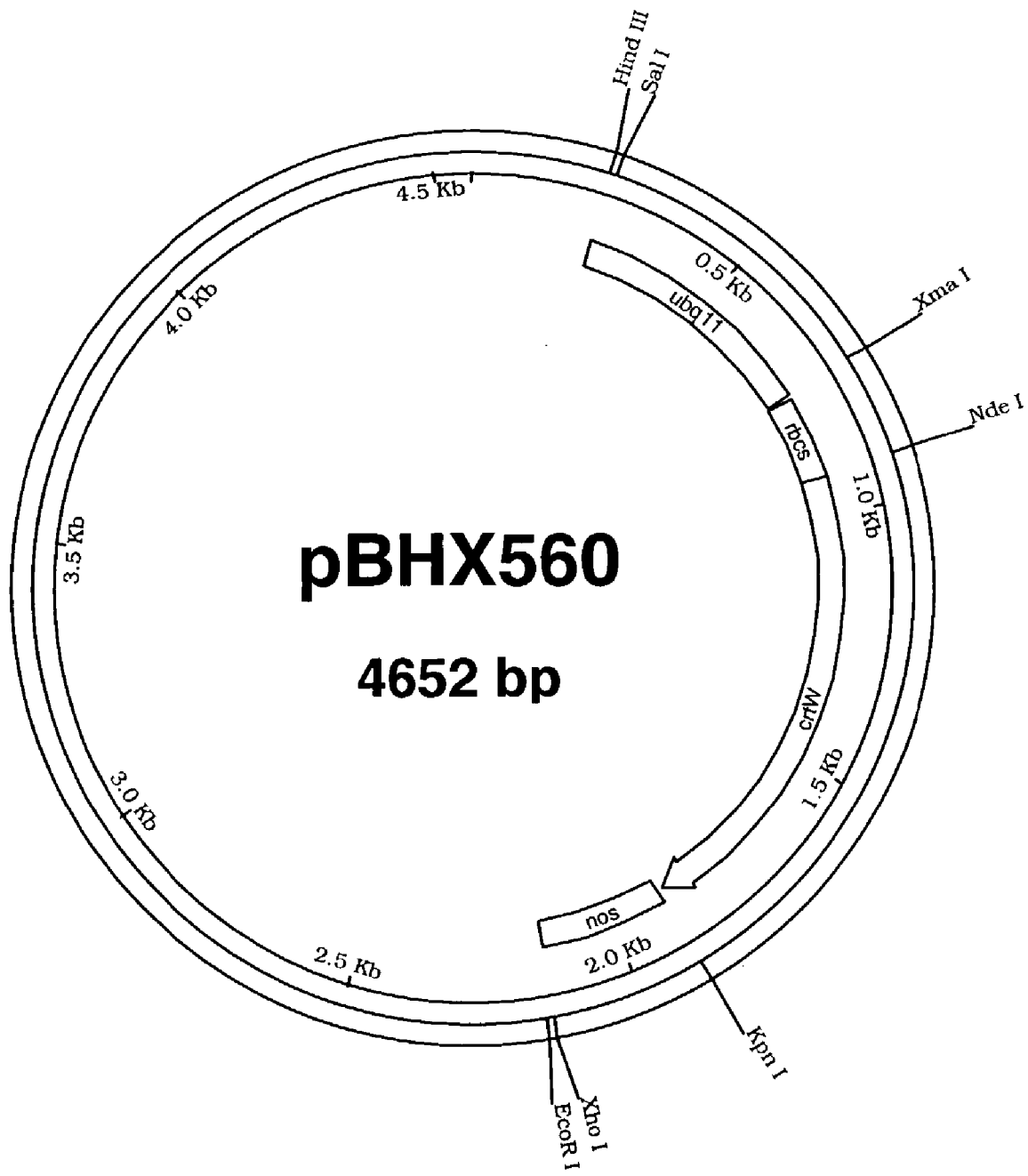

FIG. 7 schematically shows plasmid pBHX560 that contains the approximately 4652 bp DNA segment made from plasmid pBHX544 that contains the ubiquitin 11 (UBQ11) promoter from *Arabidopsis thaliana* in place of the LIS1 promoter, as well as several important restriction enzyme sites and their position numbers.

Figure 8:
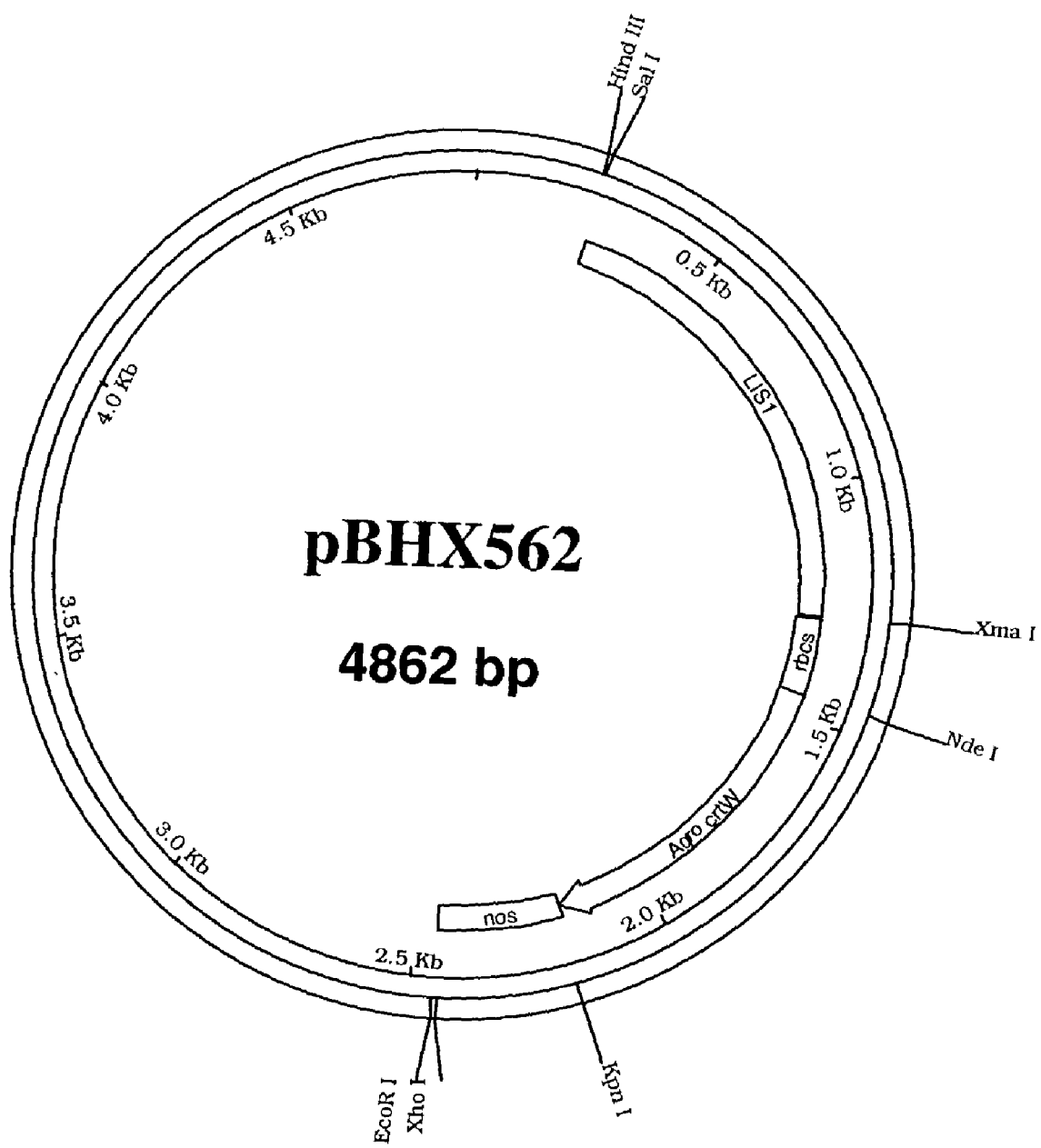

FIG. 8 schematically shows plasmid pBHX562 that contains the approximately 4862 bp DNA segment made from plasmid pBHX544 that contains the *Agrobacterium aurantiacum* crtW gene in place of the gene from *Haematococcus pluvialis*, as well as several important restriction enzyme sites and their position numbers.

Figure 9:
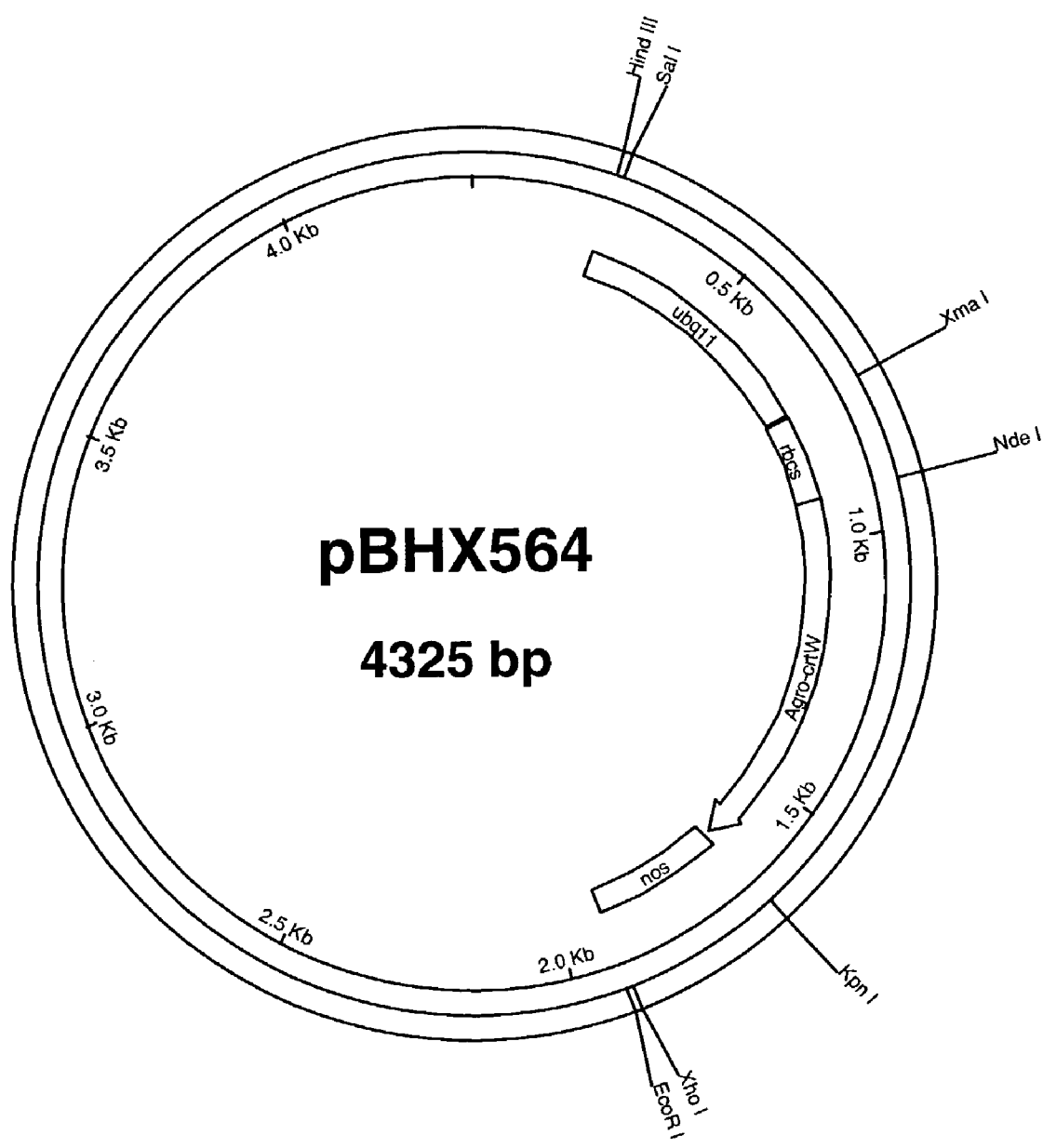

FIG. 9 schematically shows plasmid pBHX564 that contains the approximately 4325 bp DNA segment made from plasmid pBHX560 that contains the *Agrobacterium aurantiacum* crtW gene in place of the gene from *Haematococcus pluvialis*, as well as several important restriction enzyme sites and their position numbers.

Figure 10:
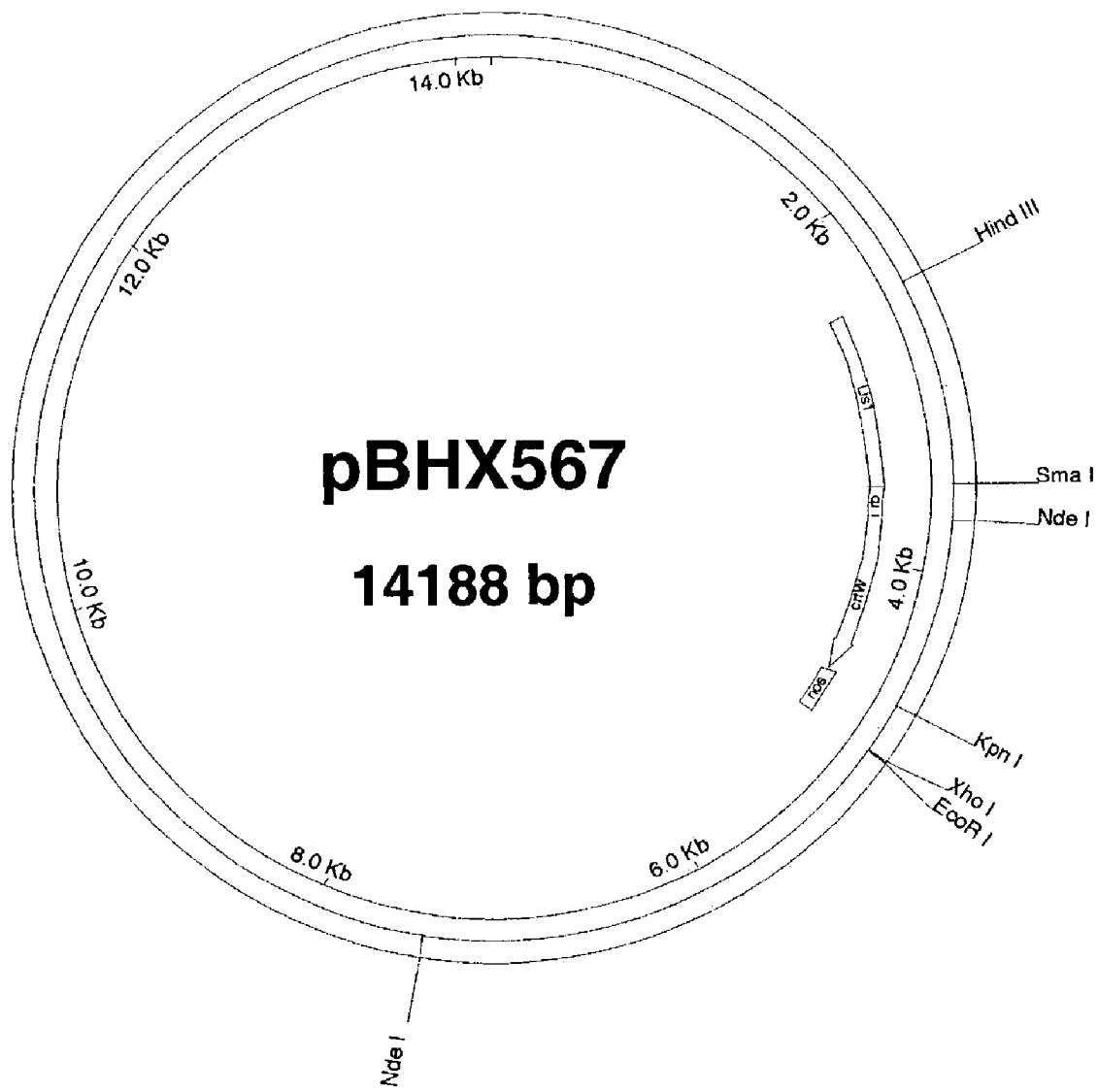

FIG. 10 schematically shows binary plasmid pBHX567 that contains the approximately 14,188 bp DNA segment that includes DNA encoding the RUBISCO (RBCS)/ketolase (*Haematococcus pluvialis* crtW) chimeric polypeptide, as well as the 3' termination sequence from Agrobacterium Ti-DNA that encodes nopaline synthase (nos), the promoter 5' upstream to the linalool synthase 1 gene (LIS1), as well as several important restriction enzyme sites and their position numbers.

Figure 11:
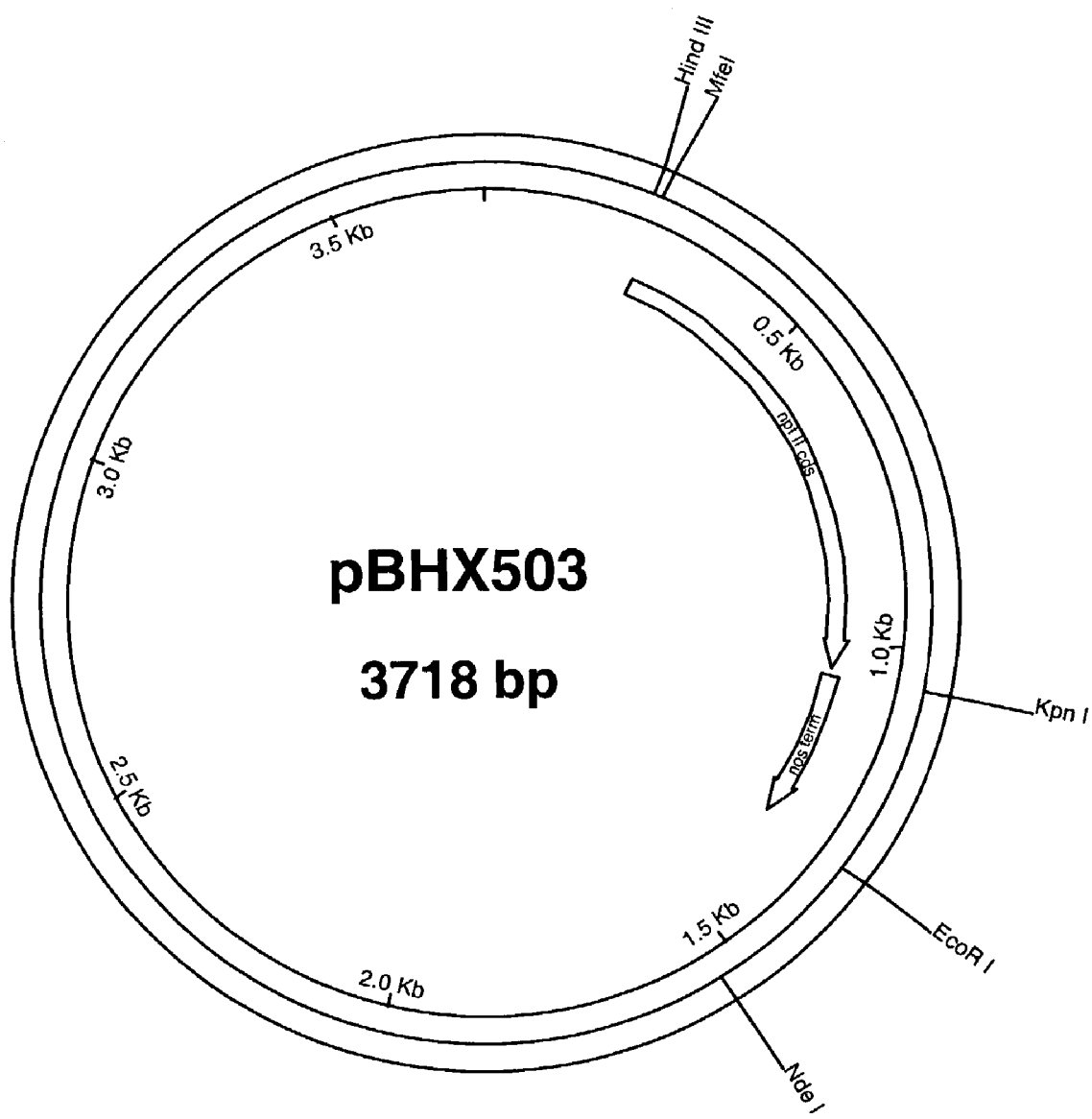

FIG. 11 schematically shows intermediate plasmid pBHX503 that was prepared from commercial vector pBI101 that was engineered to contain an approximately 3718 bp neomycin phosphotransferase II (nptII) selectable marker using PCR that also added a Hind III and MFE I site at the 5' end of the insert and a Kpn I site at the 3' end, as well as several important restriction enzyme sites and their position numbers.

Figure 12:
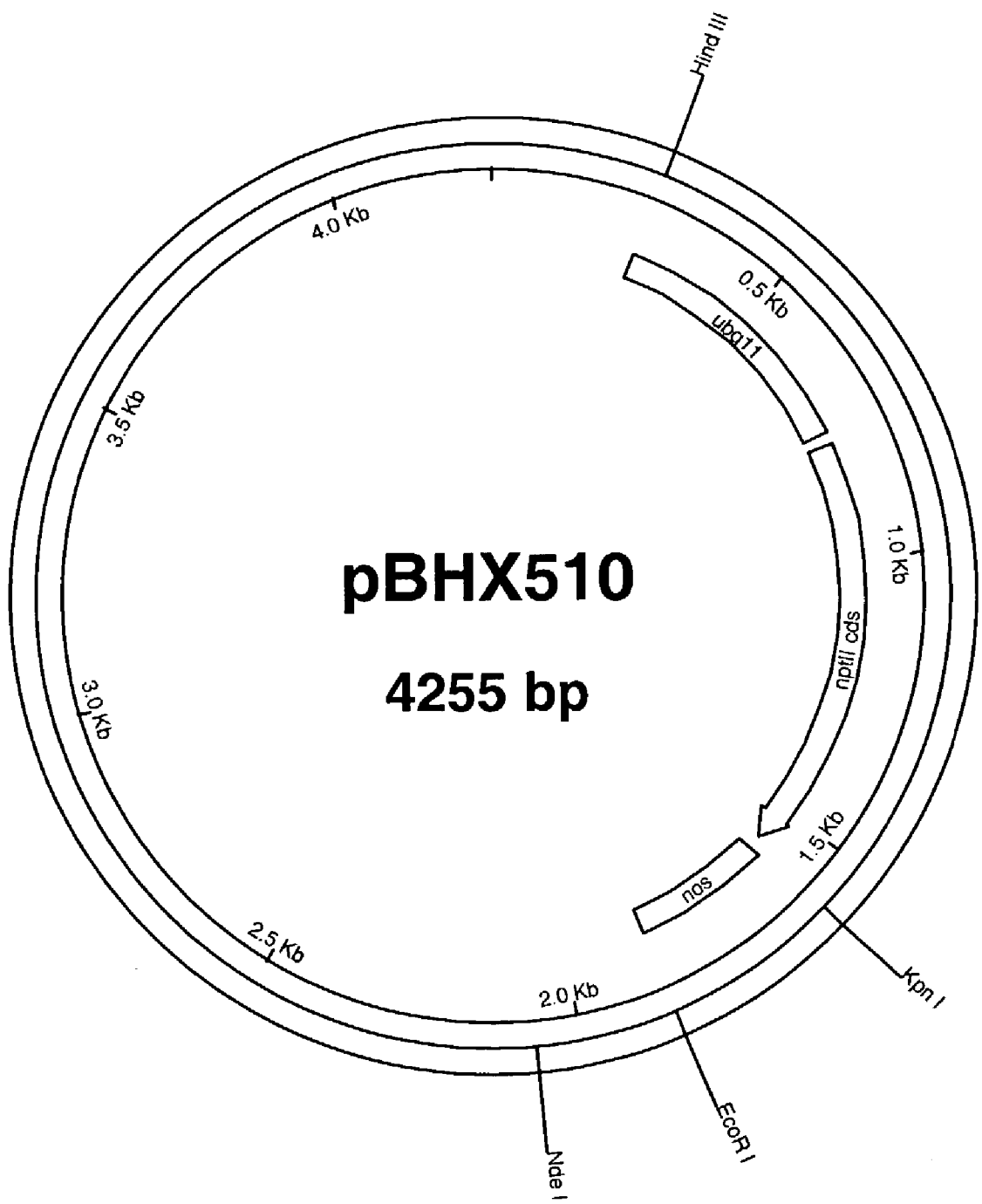

FIG. 12 schematically shows intermediate plasmid pBHX510 that was prepared from plasmid pBHX503 to which the UBQ11 promoter was operatively linked at the 3' terminus so that the plasmid contained an approximately 4255 bp DNA segment, as well as several important restriction enzyme sites and their position numbers.

Figure 13:
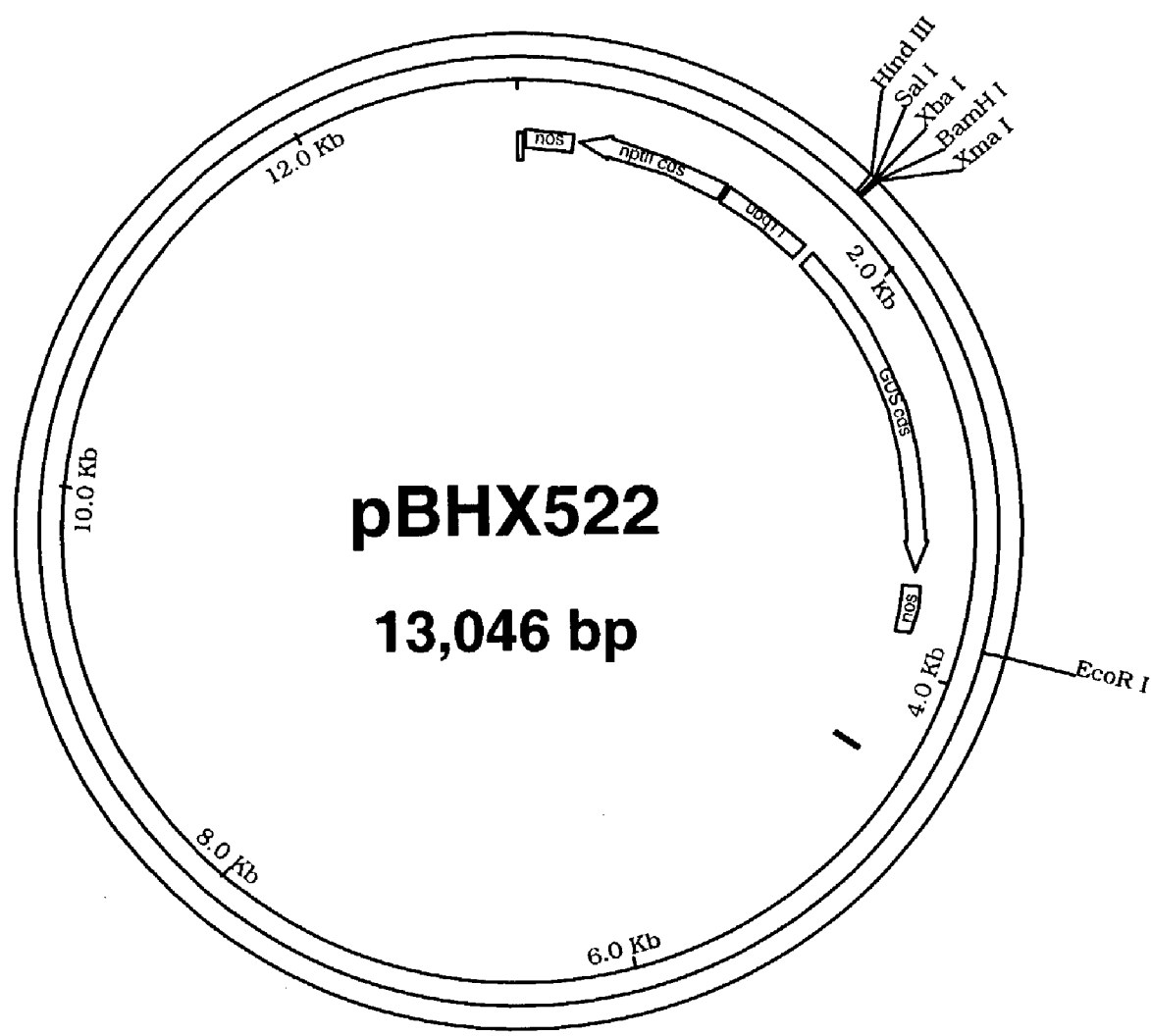

FIG. 13 schematically shows intermediate plasmid pBHX522 that was prepared from plasmid pBHX510 and was engineered to contain an approximately 13,046 bp DNA segment that includes the nptII marker gene controlled by the UBQ11 promoter and the nos polyadenylation site, as well as several important restriction enzyme sites and their position numbers.

Figure 14:
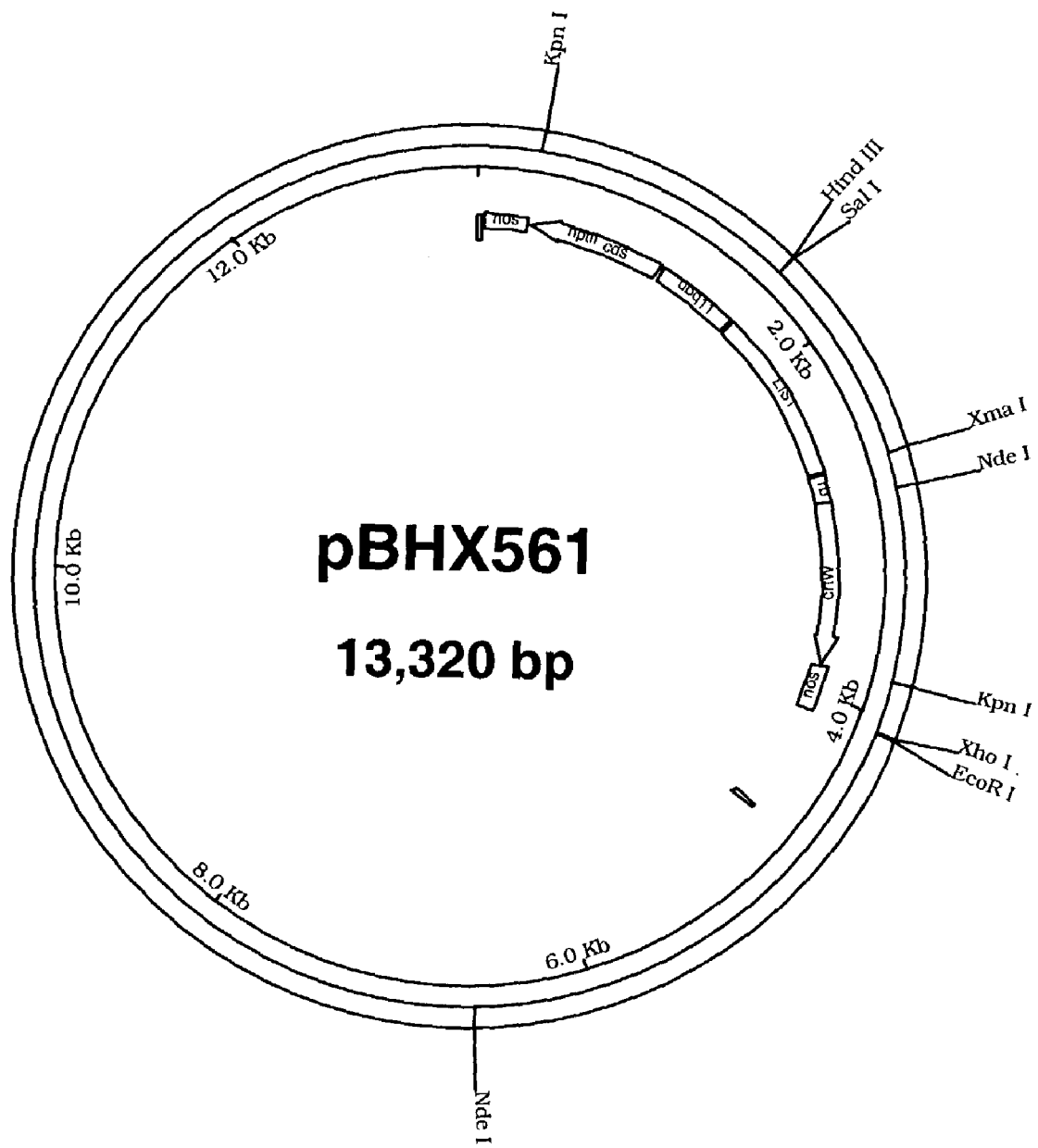

FIG. 14 schematically shows binary plasmid pBHX561 that contains the approximately 13,320 bp DNA segment that includes DNA encoding the chimeric enzyme and control sequences of plasmid pBHX544 in place of the β-glucuronidase coding region (gusA) and nos polyadenylation site of plasmid pBHX522, as well as several important restriction enzyme sites and their position numbers.

Figure 15:
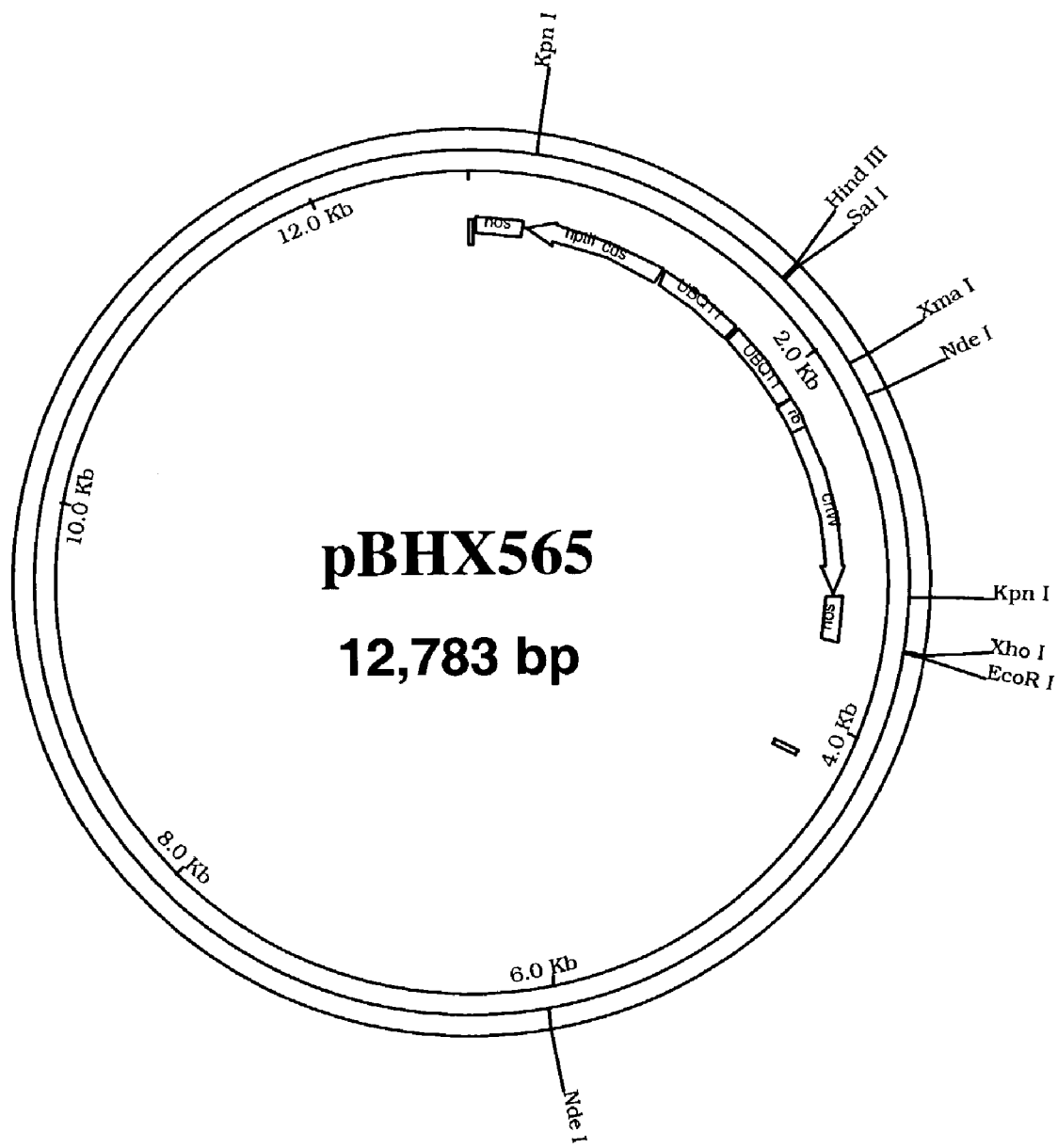

FIG. 15 schematically shows binary plasmid pBHX565 that contains the approximately 12,783 bp DNA segment that includes DNA encoding the chimeric enzyme and control sequences of plasmid pBHX560 in place of the β-glucuronidase (gusA) coding region and nos polyadenylation site of plasmid pBHX522, as well as several important restriction enzyme sites and their position numbers.

Figure 16:
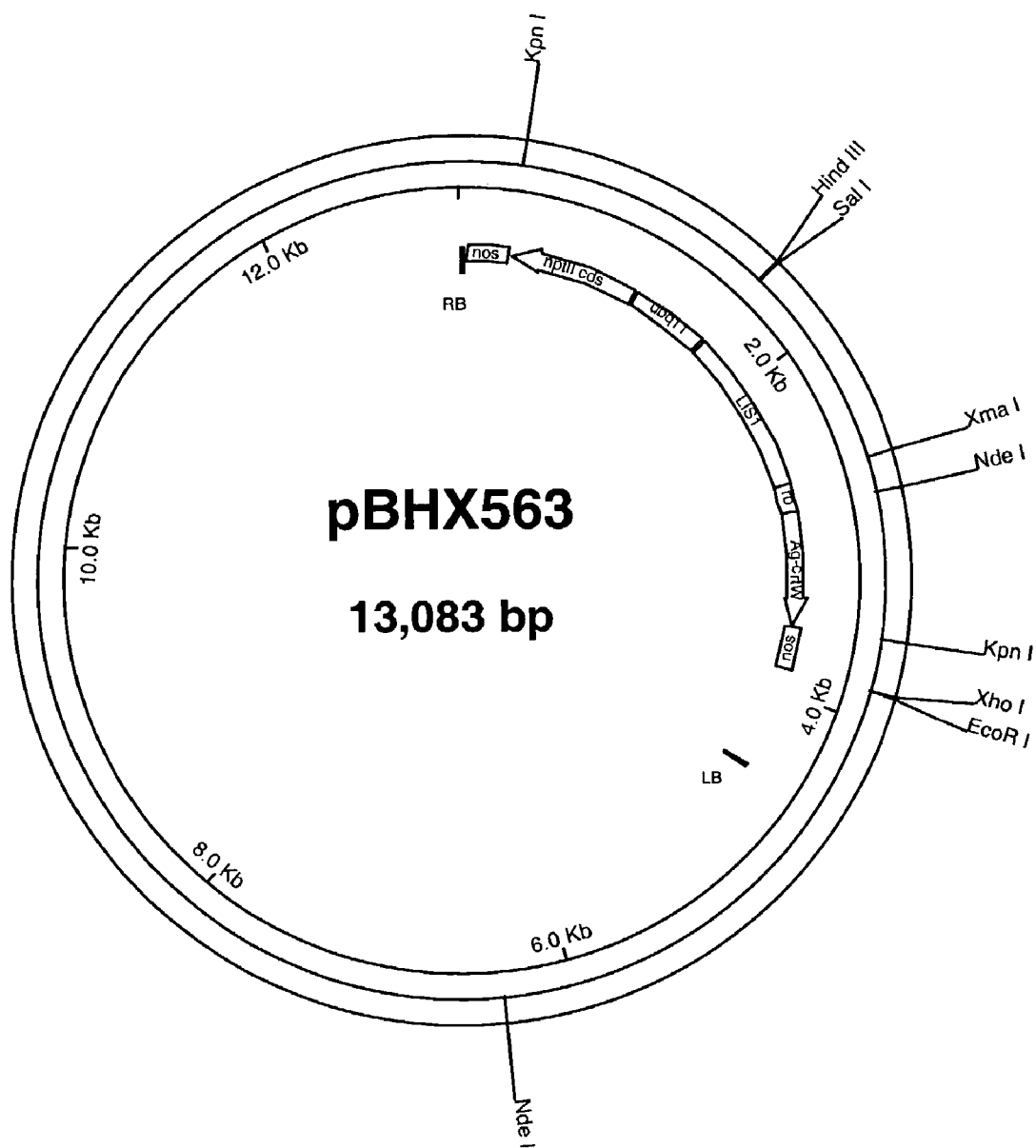

FIG. 16 schematically shows binary plasmid pBHX563 that contains the approximately 13,083 bp DNA segment that includes DNA encoding the chimeric enzyme and control sequences of plasmid pBHX562 in place of the β-glucuronidase (gusA) coding region and nos polyadenylation site of plasmid pBHX522, as well as several important restriction enzyme sites and their position numbers.

Figure 17:
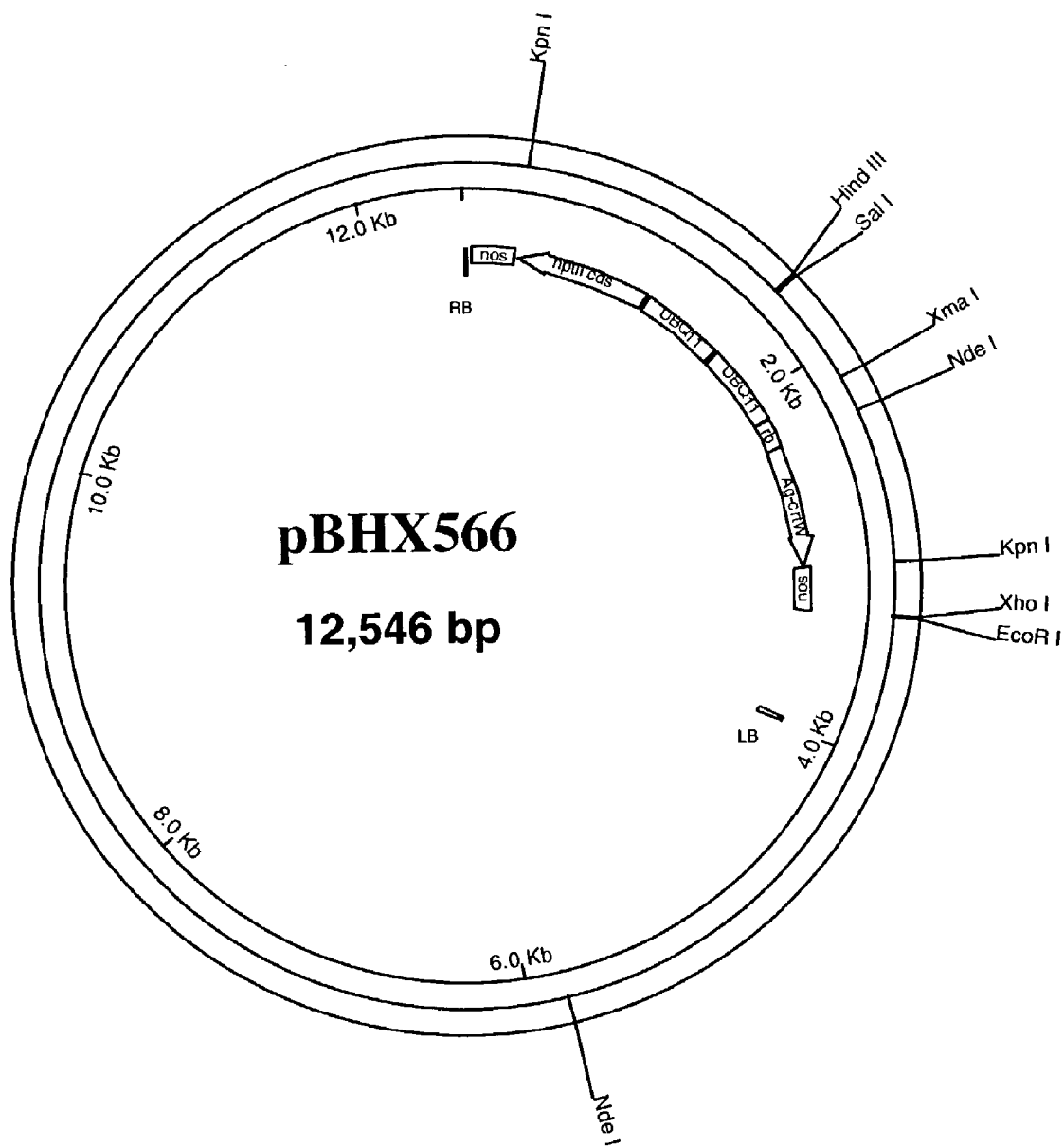

FIG. 17 schematically shows binary plasmid pBHX566 that contains the approximately 12,546 bp DNA segment that includes DNA encoding the chimeric enzyme and control sequences of plasmid pBHX564 in place of the β-glucuronidase (gusA) coding region and nos polyadenylation site of plasmid pBHX522, as well as several important restriction enzyme sites and their position numbers.

Figure 18:
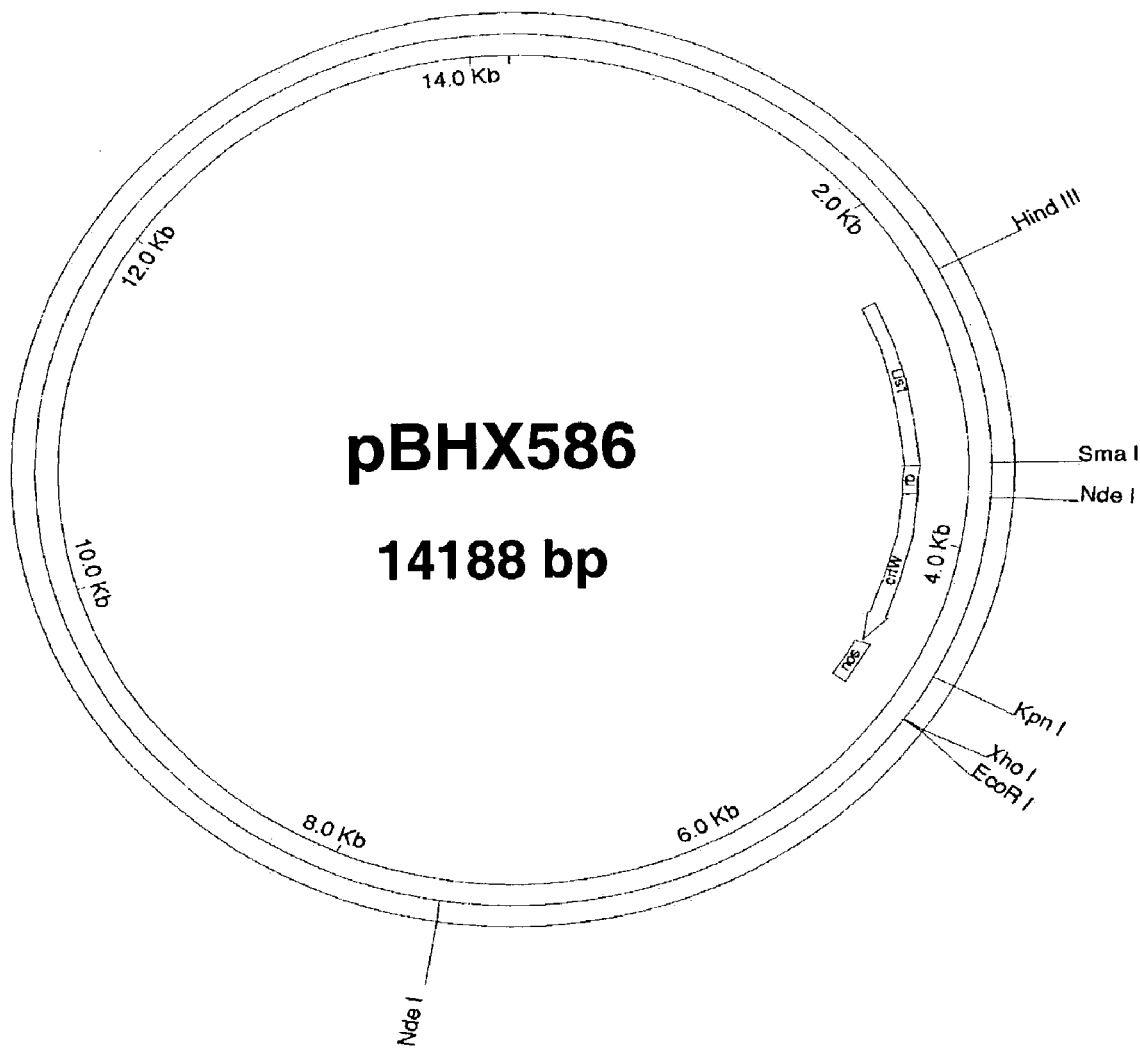

FIG. 18 schematically, shows binary plasmid pBHX586 that contains the approximately 14,188 bp DNA segment that includes DNA encoding the RUBISCO (RBCS)/ketolase (*Haematococcus pluvialis* crtW) chimeric polypeptide, as well as the 3' termination sequence from *Agrobacterium* Ti-DNA that encodes nopaline synthase (nos), the promoter 5' upstream to the linalool synthase 1 gene (LIS1), as well as several important restriction enzyme sites and their position numbers.

Figure 19:
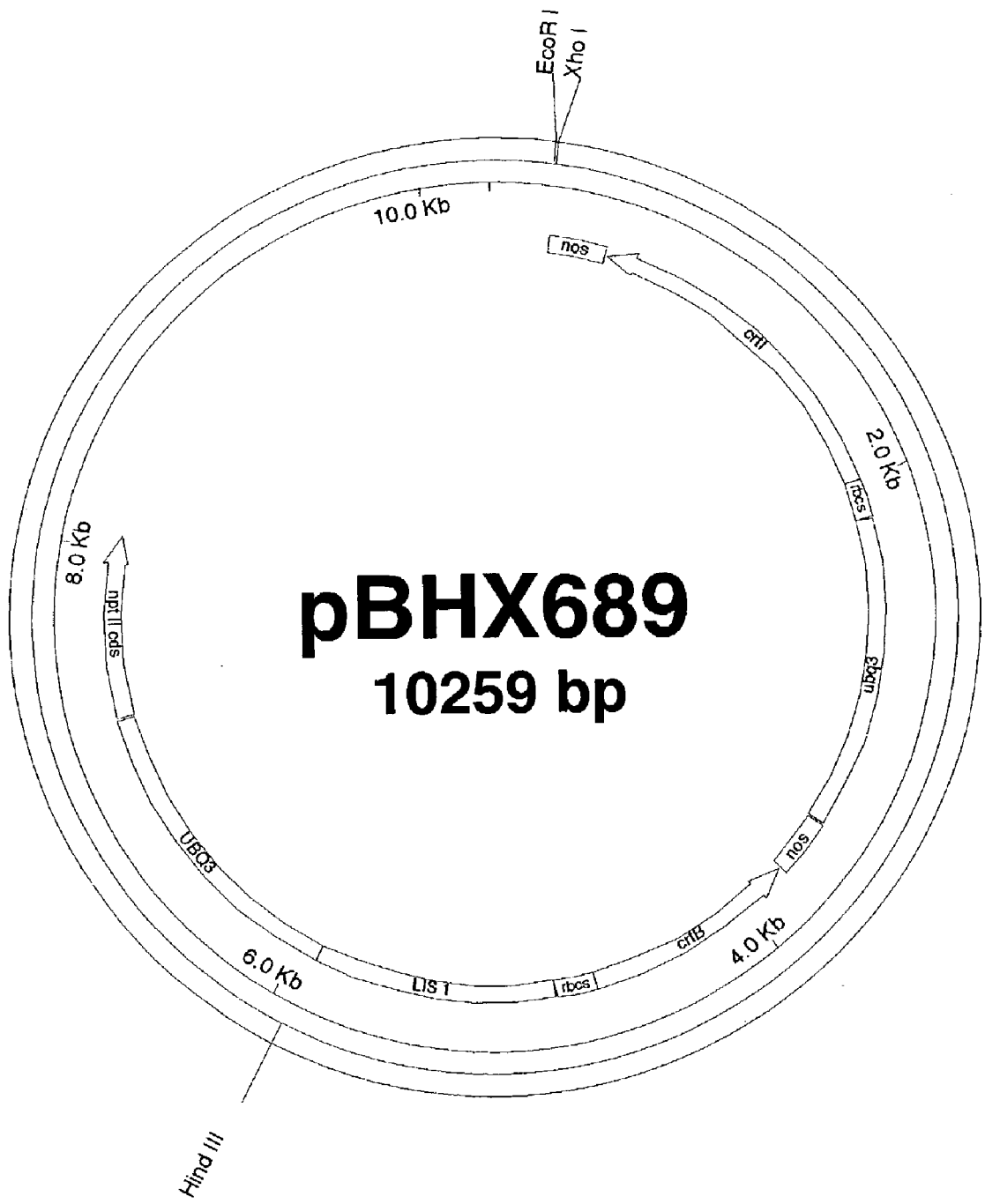

FIG. 19 schematically shows plasmid pBHX689 that contains an approximately 10259 base pair (bp) DNA segment that includes the promoter 5' upstream to the linalool synthase 1 gene (LIS1), the small subunit of RUBISCO (RBCS), a sequence that encodes a phytoene synthase (*Erwinia uredovora* crtb) polypeptide, the 3' termination sequence from *Agrobacterium* Ti-DNA that encodes nopaline synthase (nos), the ubiquitin 3 promoter, small subunit of RUBISCO (RBCS), a sequence that encodes phytoene desaturase (*Erwinia uredovora* crti) polypeptide, another 3' termination sequence from *Agrobacterium* Ti-DNA that encodes nopaline synthase (nos), another ubiquitin 3 promoter, and the selectable marker gene nptII, as well as several important restriction enzyme sites and their position numbers.

Figure 20:

FIG. 20 schematically shows plasmid pBHX691 that contains an approximately 9356 base pair (bp) DNA segment that includes the promoter 5' upstream to the linalool synthase 1 gene (LIS1), the small subunit of RUBISCO (RBCS), a sequence that encodes a ketolase (*Haematococcus pluvialis* crtW) polypeptide, the 3' termination sequence from *Agrobacterium* Ti-DNA that encodes nopaline synthase (nos), the ubiquitin 3 promoter, small subunit of RUBISCO (RBCS), a sequence that encodes a hydroxylase (*Erwinia uredovora* crtZ) polypeptide, another 3' termination sequence from *Agrobacterium* Ti-DNA that encodes nopaline synthase (nos), another ubiquitin 3 promoter, and the selectable marker gene nptII, as well as several important restriction enzyme sites and their position numbers.

Figure 21:
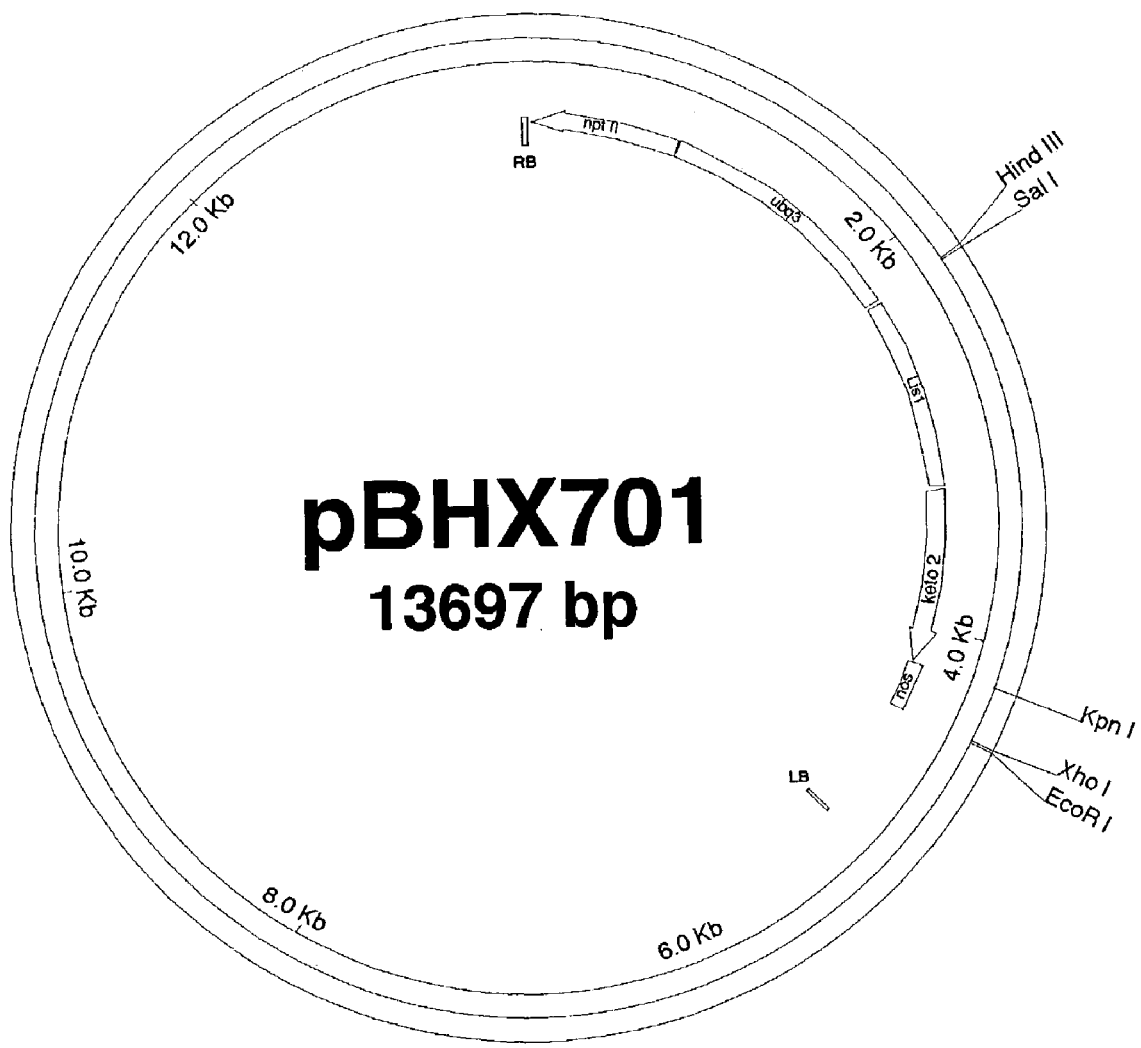

FIG. 21 schematically shows plasmid pBHX701 that contains an approximately 13697 base pair (bp) DNA segment that includes the promoter 5' upstream to the linalool synthase 1 gene (LIS1), a ketolase coding sequence, Keto2 cds, (*Adonis aestivalis* AdK6) and the 3' termination sequence from *Agrobacterium* Ti-DNA that encodes nopaline synthase (nos), the ubiquitin 3 promoter, and the selectable marker gene nptII, as well as several important restriction enzyme sites and their position numbers.

Figure 22:
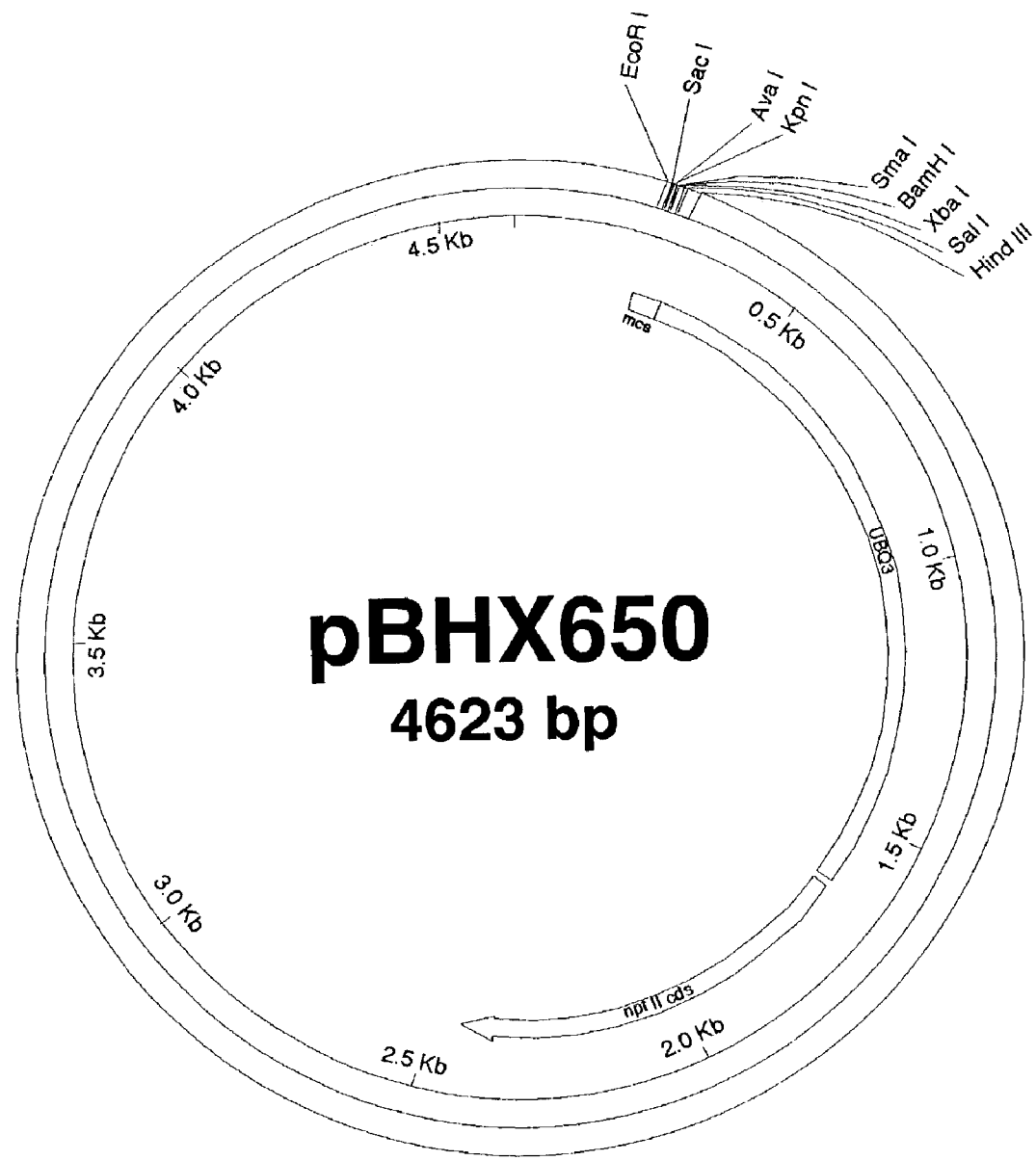

FIG. 22 schematically shows plasmid pBHX650 that contains an approximately 4623 base pair (bp) DNA segment that includes a multiple unique cloning site (mcs), ubiquitin 3 promoter (UBQ3) and the selectable marker gene nptII.

Figure 23:
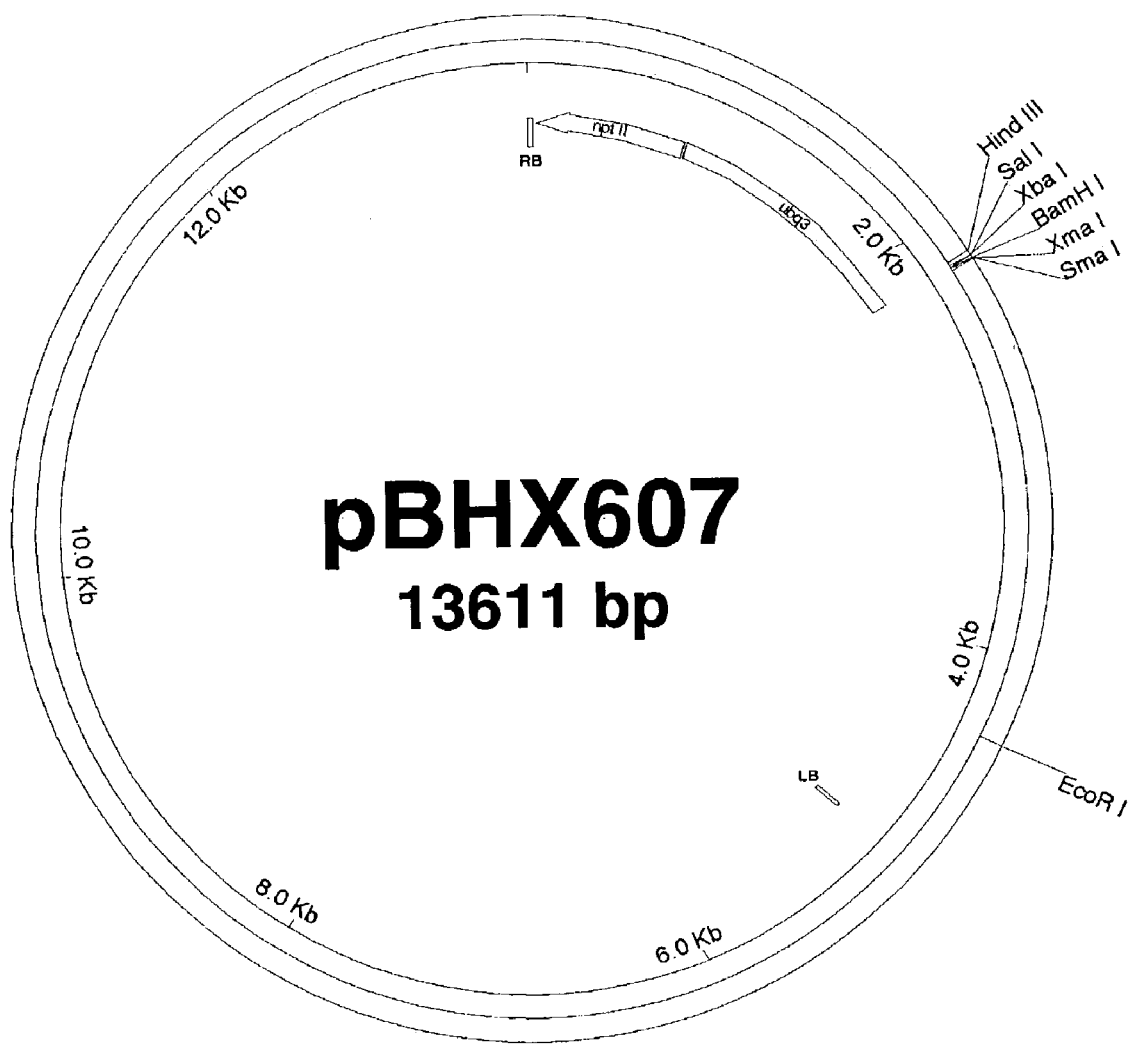

FIG. 23 schematically shows plasmid pBHX607 that contains an approximately 13611 base pair (bp) DNA segment that includes a multiple unique cloning site (mcs), the ubiquitin 3 promoter, and the selectable marker gene nptII.

Figure 24:
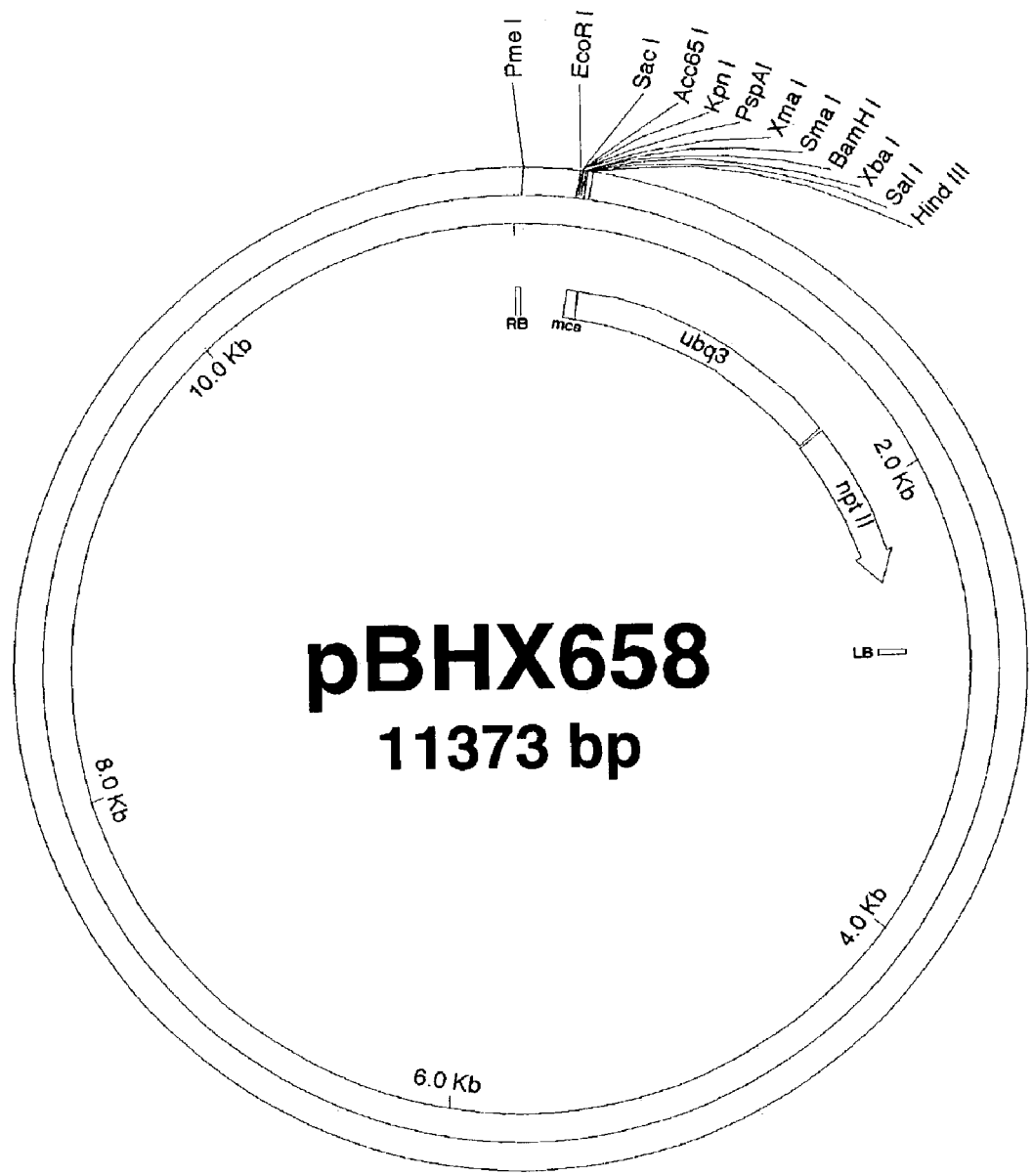

FIG. 24 schematically shows plasmid pBHX658 that contains an approximately 11373 base pair (bp) DNA segment that includes a multiple unique cloning site, the ubiquitin 3 promoter and the selectable marker gene nptII.

Figure 25:
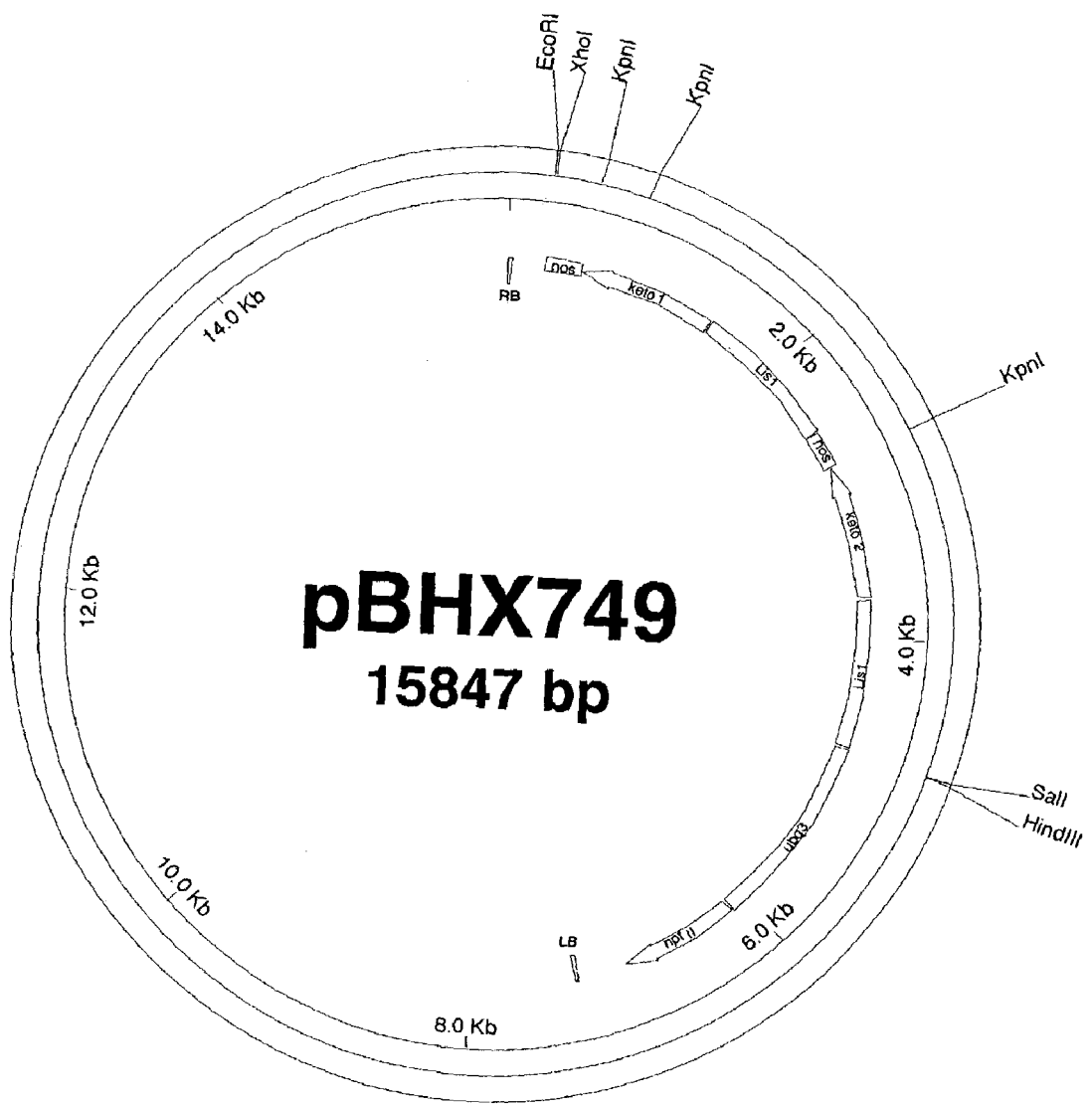

FIG. 25 schematically shows plasmid pBHX749 that contains an approximately 15847 base pair (bp) DNA segment that includes the promoter 5' upstream to the linalool synthase 1 gene (LIS1), a ketolase coding sequence, Keto2 cds, (Adonis aestivalis AdK6) and the 3' termination sequence from Agrobacterium Ti-DNA that encodes nopaline synthase (nos), the promoter 5' upstream to the linalool synthase 1 gene (LIS1), a ketolase coding sequence, Ketol cds, (Adonis aestivalis AdK1) and the 3' termination sequence from Agrobacterium Ti-DNA that encodes nopaline synthase (nos), the ubiquitin 3 promoter, and the selectable marker gene nptII, as well as several important restriction enzyme sites and their position numbers.

Figure 26:
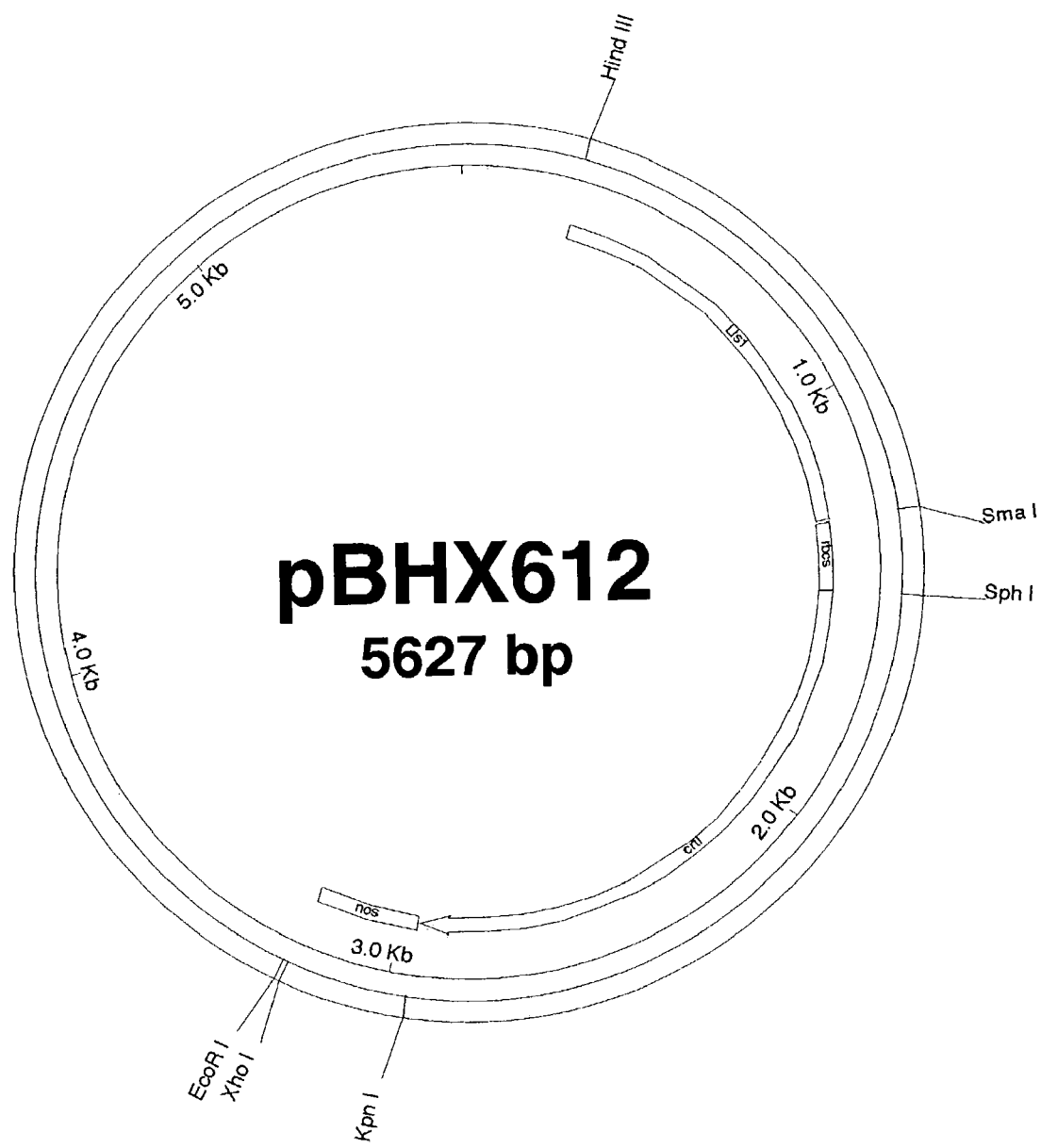

FIG. 26 schematically shows plasmid pBHX612 that contains an approximately 5627 base pair (bp) DNA segment that includes the promoter 5' upstream to the linalool synthase 1 gene (LIS1), the small subunit of RUBISCO (RBCS), a sequence that encodes a phytoene desaturase (Erwinia uredovora crtI) polypeptide, and the 3' termination sequence from Agrobacterium Ti-DNA that encodes nopaline synthase (nos), as well as several important restriction enzyme sites and their position numbers.

DEFINITION OF TERMS

Amino Acid: All amino acid residues identified herein are in the natural L-configuration. In keeping with standard polypeptide nomenclature, J. Biol. Chem., 243:3557–59 (1969), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

Carotene: A hydrocarbon carotenoid pigment such as lycopene, α-carotene and β-carotene.

Expression: The combination of intracellular processes, including transcription and translation undergone by a structural gene to produce a polypeptide.

Expression vector: A DNA sequence that forms control elements that regulate expression of structural genes when operatively linked to those genes within a vector.

Flower petal-preferred promoter: Refers to a promoter that preferentially directs the over-expression or production of an operatively linked gene in the flower petals.

Hybridization: The term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

Hydroxylase: Refers to the gene and encoded enzyme that causes a hydroxyl group to be added to the carbon atom at the 3-position of a carotenoid β-ionene ring to form zeaxanthin or another hydroxylated intermediate in the later stages of the carotenoid biosynthesis pathway. Specifically, "hydroxylase" (or β-carotene hydroxylase) is an enzyme that converts β-carotene or a 4-keto-β-carotene into one or more compounds that are hydroxylated at the 3-positon of the β-ionene ring.

Different sources encoding the hydroxylase enzyme portion that converts a carotenoid β-ionene ring into a 3-hydroxy-β-ionene ring has been identified. The crtZ gene of Erwinia uredovora encodes hydroxylase as does the crtZ gene of Erwinia herbicola. (See Misawa et al. U.S. Pat. No. 5,419,939; and Ausich, et. al. U.S. Pat. No. 5,684,238).

Integrated: A heterologous DNA sequence incorporated into a host chromosome (genome) is integrated.

Ketolase: Refers to the gene and encoded enzyme (β-carotene ketolase or β-carotene oxygenase) that causes a ketone (oxo) group to be added to the 4-position carbon atom of a carotenoid β-ionene ring to form various keto-carotenoid compounds in the later stages of the carotenoid biosynthesis pathway. There are several sources of genes that encode the ketolase enzyme that converts a carotenoid β-ionene ring into a 4-keto-β-ionene ring such as the crtW gene, the bkt gene and the crtO gene. [See Kajiwara et al., Plant Molecular Biology, 29:343–352, (1995); Misawa et al.

U.S. Pat. Nos. 5,811,273 and No. 5,972,690; Kajiwara et al. U.S. Pat. No. 5,910,433; Harker et al., *FEBS Letters,* 404: 129–134 (1997); Lotan et al., *FEBS Letters,* 364:125–128 (1995); and Hirschberg et al. U.S. Pat. No. 5,965,795.]

Two cDNA molecules isolated from *Haematococcus pluvialis* have been separately shown to encode β-carotene ketolase (β-carotene oxygenase) enzymes that convert a methylene group of a carotenoid β-ring into a keto group (thus acting as a "ketolase"). One gene and gene product has been designated as bkt. [See Kajiwara et al. U.S. Pat. No. 5,910,433; and Kajiwara et al., *Plant Mol. Biol.,* 29:343–352 (1995).] The other gene was designated crtO for β-carotene 4-oxygenase. [See Hirschberg et al. U.S. Pat. No. 5,965,795; Harker et al., *FEBS Letters,* 404:129–134 (1997) and Lotan et al., *FEBS Letters,* 364:125–128 (1995).]

Genes corresponding to bkt were found in the marine bacteria *Agrobacterium aurantiacum* and *Alcaligenes* PC-1. These genes and gene predicts, referred to as crtW, have about 37 percent identity to the bkt gene product of the *H. pluvialis*. [See Misawa et al. U.S. Pat. No. 5,972,690.]

Nucleic Acid Hybridization: A function of sequence identity (homology), G+C content of the sequence, buffer salt content, sequence length and duplex melt temperature ($T_m$) among other variables. [See Maniatis et al., *Molecular Cloning,* Cold Spring Harbor Laboratory, Cold Spring Harbor, N.Y. (1982), page 388.] High stringency conditions, for example, utilize high temperature hybridization (e.g., 65° C. to 70° C.) in aqueous solution containing 4× to 6×SSC (1×SSC=0.15 M NaCl, 0.015 M sodium citrate) or 40 to 45° C. in 50% formamide combined with washes at high temperature (e.g. 5° C. to 25° C. below the $T_m$), in a solution having a low salt concentration (e.g., 0.1×SSC). Moderate stringency conditions typically utilize hybridization at a temperature about 50° C. to about 65° C. in 0.2 to 0.3 M NaCl, and washes at about 50° C. to about 55° C. in 0.2×SSC, 0.1% SDS. Low stringency conditions can utilize lower hybridization temperature (e.g. 35° C. to 45° C. in 20% to 50% formamide) with washes conducted at a low intermediate temperature (e.g. 40 to 55° C.) and in a wash solution having a higher salt concentration (e.g. 2× to 6×SSC). Moderate stringency conditions are preferred for use in conjunction with the disclosed polynucleotide molecules as probes to identify clones encoding nucleoside diphosphate kinases of the invention. [See Ausich, et al. U.S. Pat. No. 5,684,238.]

Operatively linked or inserted: A vector DNA sequence is operatively linked to a structural gene DNA sequence if the two are covalently bonded in correct reading frame and situated so that the promoter DNA sequence influences the transcription or translation of the structural gene DNA sequence.

Promoter: A recognition site on a DNA sequence or group of DNA sequences that provide an expression control element for a gene and to which RNA polymerase specifically binds and initiates RNA synthesis (transcription) of that gene.

Recombinant DNA molecule: A hybrid DNA sequence comprising at least two nucleotide sequences not normally found together in nature.

Plant of the same type: The phrase "plant of the same type" is used herein to describe a representative plant that is used as a basis for comparisons of flower petal carotenoid accumulation. A "plant of the same type" is a plant of the same genus and species, and is preferably of the same parentage (cross) as the mutant and/or transformed plant to which it is compared. A plant contemplated for such comparative use is a hybrid that is typically commercially available such as the marigold 'Scarletade' that is used illustratively herein, and unless otherwise stated, is itself neither a mutant nor a plant transformed to enhance production of one or more carotenoids. Thus, as is seen hereafter, the carotenoids extracted from the petals and leaves of the marigold 'Scarletade' are used for comparison with those extracted from mutagenized or transformed *T. erecta* marigolds. Where alleic variations among siblings of a cross are small, as with extensively inbred plants, comparisons between siblings can be used or an average arrived at using several siblings. Otherwise, clones are preferred for the comparison to mutated or transformed plants.

In some comparisons, the mutagenized or transformed plants can themselves be the representative plant against which a differently mutagenized or transformed plant is compared for extracted carotenoids. Thus, for example, the carotenoids extracted from a transformed, previously mutagenized plant can be compared to those extracted from the mutagenized plant.

Stringency: The term "stringency" is used in reference to the conditions of temperature, ionic strength, and the presence of other compounds, under which nucleic acid hybridizations are conducted. With "high stringency" conditions, nucleic acid base pairing occurs only between nucleic acid fragments that have a high frequency of complementary base sequences. Thus, conditions of "weak" or "low" stringency are often required when it is desired that nucleic acids that are not completely complementary to one another be hybridized or annealed together. The art knows well that numerous equivalent conditions can be employed to comprise low stringency conditions. The choice of hybridization conditions is generally evident to one skilled in the art and is usually be guided by the purpose of the hybridization, the type of hybridization (DNA-DNA, or DNA-RNA), and the level of desired relatedness between the sequences [See for example Ausich et al., U.S. Pat. No. 5,684,238.]

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridization often is determined by the salt concentration and/or temperature used for the post-hybridization washes. In general, the stringency of the hybridization reaction itself can be reduced by reducing the percentage of formamide in the hybridization solution.

High stringency conditions, for example, can utilize high temperature hybridization (e.g., 65° C. –68° C. in aqueous solution containing 4–6×SSC (1×SSC=0.15 M NaCl, 0.015 M sodium citrate) or 42° C. in 50% formamide combined with washes at high temperature (e.g. 5° C.–25° C. below the $T_m$), in a solution having a low salt concentration (e.g., 0.1×SSC). Low stringency conditions can utilize lower hybridization temperature (e.g. 35° C.–42° C. in 20–50% formamide) with washes conducted at an intermediate temperature (e.g. 40–60° C.) and in a wash solution having a higher salt concentration (e.g. 2–6×SSC). Moderate stringency conditions, which can utilize hybridization in 0.2–0.3 M NaCl at a temperature between 50° C.–65° C. and washes in 0.2×SSC, 0.1% SDS at between 50° C. and 55° C., can be used in conjunction with the disclosed polynucleotide molecules as probes to identify clones encoding NDPK.

Structural gene: A DNA sequence that is expressed as a polypeptide; i.e., an amino acid residue sequence.

$T_m$ (melting temperature): The term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The $T_m$ of a hybrid nucleic acid is often estimated using a formula adopted from hybridization assays in 1 M salt, and commonly used for calculating $T_m$ for PCR primers: [(number of A+T)×2° C.+(number of G+C)×4° C.]. C. R. Newton et al. PCR, $2^{nd}$ Ed., Springer-Verlag (New York: 1997), p. 24. This formula was found to be inaccurate for primers longer that 20 nucleotides. Id. Other more sophisticated computations exist in the art which take structural as well as sequence characteristics into account for the calculation of $T_m$. A calculated $T_m$ is merely an estimate; the optimum temperature is commonly determined empirically.

Vector: A DNA molecule capable of replication in a cell and/or to which another DNA segment can be operatively linked so as to bring about replication of the attached segment. A plasmid is an exemplary vector. The symbol "::" is used herein to indicate a fusion between adjacent elements in a plasmid or other vector, such as between the LIS1 promoter, the crtW carotenoid enzyme-forming gene and the nos terminating sequence.

Xanthophyll: A carotenoid pigment having an oxygen-containing group such as a hydroxyl group, a keto group or an epoxy group present in one or both ionene rings.

DETAILED DESCRIPTION OF INVENTION

Overview

Many flowering plants (including but not limited to preferred flowering plants) contain carotenoids or carotenoid precursors in their flower parts such as their petals and/or reproductive parts. Even in the absence of β-carotene, higher plants can serve as host for the biotechnological production of carotenoid compounds that contain a β-ring that contains a 4-keto group such as canthaxanthin and astaxanthin.

A carotenoid, once formed, can be the precursor for the next-made carotenoid along the biosynthetic pathway. If a carotenoid is present along with an appropriate enzyme to convert that carotenoid to the next carotenoid molecule in a selected pathway, that conversion usually occurs for each step in a pathway, so long as the precursor carotenoid substrate and suitable enzyme are present in appropriate parts of a flower.

The above product as precursor results in an accumulation in the plant of one or more carotenoids formed later in the biosynthetic reaction pathway relative to a small or no accumulation of earlier-formed precursor carotenoids. This relative lack of accumulation of precursor carotenoids is particularly evident where any of α- or β-carotene, lutein or zeaxanthin are the terminally-produced carotenoids in that little or no precursor lycopene is usually observed in mature plant parts such as fruits.

As is well known, the relative amounts of biologically produced materials such as a contemplated 4,4'-diketo carotenoid are subject to several variables that here include the concentration of precursor carotenoid, the rate of enzymatic conversion to the next carotenoid and possible product feedback inhibition by which a produced carotenoid inhibits its own further reaction. Some plants can also produce a non- or poorly-functional converting enzyme so that later seemingly producible carotenoids are not produced or are produced in only relatively small amounts. Man-made inhibitors that work on late, but not early conversion enzymes can also play a role in which carotenoid is accumulated.

The present invention contemplates a transgenic plant and a process for using that plant as well as products produced from that plant. Useful flowering plants that can be made transgenic include Amaryllidaceae (Allium, Narcissus); Apocynaceae (Catharanthus); Asteraceae, alternatively Compositae (Aster, Calendula, Callistephus, Cichorium, Coreopsis, Dahlia, Dendranthema, Gazania, Gerbera, Helianthus, Helichrysum, Lactuca, Rudbeckia, Tagetes, Zinnia); Balsaminaceae (Impatiens); Begoniaceae (Begonia); Caryophyllaceae (Dianthus); Chenopodiaceae (Beta, Spinacia); Cucurbitaceae (Citrullus, Curcurbita, Cucumis); Cruciferae (Alyssum, Brassica, Erysimum, Matthiola, Raphanus); Gentinaceae (Eustoma); Geraniaceae (Pelargonium); Graminae, alternatively Poaceae, (Avena, Horedum, Oryza, Panicum, Pennisetum, Poa, Saccharum, Secale, Sorghum, Triticum, Zea); Euphorbiaceae (Poinsettia); Labiatae (Salvia); Leguminosae (Glycine, Lathyrus, Medicago, Phaseolus, Pisum); Liliaceae (Lilium); Lobeliaceae (Lobelia); Malvaceae (Abelmoschus, Gossypium, Malva); Plumbaginaceae (Limonium); Polemoniaceae (Phlox); Primulaceae (Cyclamen); Ranunculaceae(Aconitum, Anemone, Aquilegia, Caltha, Delphinium, Ranunculus); Rosaceae (Rosa); Rubiaceae (Pentas); Scrophulariaceae (Angelonia, Antirrhinum, Torenia); Solanaceae (Capsicum, Lycopersicon, Nicotiana, Petunia, Solanum); Umbelliferae (Apium, Daucus, Pastinaca); Verbenaceae (Verbena, Lantana); Violaceae (Viola). Of the before-noted plants, plants of the genus Tagetes are preferred, with Tagetes erecta (marigold) plants being particularly preferred.

One aspect contemplated by the present invention is a transformed higher plant (a transgenic plant) or a regenerable portion of such a plant, whose flower parts such as the corolla or other reproductive flower parts produce and preferably accumulate a carotenoid compound having a β-ionene ring. That transgenic plant contains a heterologous genomic DNA sequence (transgene) that (a) encodes a chimeric ketolase enzyme and (b) contains a promoter that directs expression of the chimeric enzyme. The encoded chimeric ketolase enzyme is itself comprised of two parts: (i) a N-terminal first portion comprising a plastid transit peptide portion fused to (ii) a second, ketolase enzyme portion that converts a carotenoid β-ionene ring into a 4-keto-β-ionene ring; i.e., an enzyme encoded by a crtw gene. The promoter and the plastid transit peptide are preferably from different species. The result of expression of the transgene in a contemplated plant is flower petal-preferred accumulation of a 4-keto-β-ionene ring carotenoid compound.

A contemplated plant produces a β-ionene ring-containing carotenoid compound in flower parts. Exemplary β-ionene ring-containing carotenoid compounds include β-carotene, zeaxanthin, β-cryptoxanthin, adonixanthin, 3-hydroxyechinenone, 3'-hydroxyechinenone, echinenone, canthaxanthin, and adonirubuin. Contemplated flower parts include the reproductive flower parts include: petals (corolla), stamen and pistils. For zeaxanthin, it is preferred that the (3R,3'R)-zeaxanthin be produced, whereas for astaxanthin, it is preferred that the (3S,3'S)-astaxanthin be the product produced. (3S,3'S)-Astaxanthin is the product produced by double ketolation of (3R,3'R)-zeaxanthin as the substrate for the ketolase enzyme.

Exemplary preferred non-higher plant ketolase enzymes that convert a carotenoid β-ionene ring into a 4-keto-β-ionene ring and form a portion of a chimeric enzyme are those discussed before and are disclosed in Kajiwara et al., *Plant Molecular Biology*, 29:343–352, (1995); Misawa et al. U.S. Pat. Nos. 5,811,273 and No. 5,972,690; Kajiwara et al. U.S. Pat. No. 5,910,433; Harker et al., *FEBS Letters*, 404: 129–134 (1997); Lotan et al., *FEBS Letters*, 364:125–128 (1995); and Hirschberg et al. U.S. Pat. No. 5,965,795.

Further ketolase genes whose expression products can be used herein are listed hereinafter, first by genus/species of the organism from which the gene was isolated, wherein names in parentheses are new or alternate designations from NCBI, but may not be officially recognized. The name of the gene is sometimes provided within those parentheses, and the citation at which the gene is reported follows: *Adonis aestivalis* (*Adonis palaestina;* ketolase 1) WO99/61652; *Adonis aestivalis* (*Adonis palaestina;* ketolase 2) WO99/61652; *Agrobacterium aurantiacum* (*Paracoccus* sp. MBIC1143) Misawa et al. (1995) *J. Bacteriol.* 177:6575–6584; *Alcaligenes* sp., Misawa et al. (1995) *Biochem. Biophys. Res. Comm.* 209:867–876; *Bradyrhizobium* sp. ORS278, Hannibal et al. (2000) *J. Bacteriol.* 182: 3850–3853; *Brevundimonas aurantiaca* WO02/079395 A2; *Haematococcus pluvialis* (crtW), Kajiwara et al. (1995) *Plant Mol. Biol.* 29:343–352; *Nostoc* sp. PCC 7120 (*Anabaena* sp. strain PCC 7120), Kaneko et al. (2001) *DNA Res.* 8:205–213; *Paracoccus marcusii*, U.S. Pat. No. 5,935,808; *Phaffia rhodozyma* (*Xanthophyllomyces dendrorhous*) (astaxanthin synthetase), U.S. Pat. No 6,365,386; *Synechocystis* sp. PCC 6803, Kaneko et al. (1995) *DNA Res.* 2:163–166 and Fernández-González et al. (1997) *J. Biol. Chem.* 272: 9728–9733; *Synechococcus* sp. WH 8102,GenBank ZP_00115639 (hypothetical protein Synwh1213); *Thermosynechococcus elongatus* BP-1 (crtZ), Nakamura et al. (2002) *DNA Res.* 9:135–148; and *Trichodesmium erythraeum* IMS101, GenBank ZP_00070906 (hypothetical protein Tery0029). Appropriate DNA sequences that encode those enzymes are also listed in those citations.

The N-terminal portion of a contemplated chimer comprises a plastid transit peptide fused to the ketolase portion of the chimer by a peptide bond. The C-terminus of the transit peptide portion is fused to the N-terminus of the ketolase enzyme portion.

The plastid transit peptide can be from substantially any source, and typically contains about 30 to about 80 amino acid residues. Exemplary useful peptides are disclosed in von Heijne et al., *Eur. J. Biochem.*, 180:535–545 (1989); and Clark et al., *J. Biol. Chem.*, 264(29):17544–17550 (1989). Further plastid-specific (chloroplast) transit peptides are discussed more generally in della-Cioppa et al., *Plant Physiol.*, 84:965–968 (1987).

Exemplary transit peptides include the spinach ferredoxin reductase, Rieske Fe-S protein, silene ferredoxin, pea heat-shock protein, Gln synthase, and brassica acyl carrier protein transit peptides. Amino acid residue sequences for these transit peptides and others are provided in the publication by von Heijne et al., above. A preferred plastid transit peptide is one of the tobacco RUBISCO, petunia EPSP synthase, and pepper PSY gene transit peptides.

The pepper plant transit peptide gene adjacent to the PSY gene as reported by Romer et al., *Biochem. Biophys. Res. Commun.*, 196(3):1414–1421 (1993) can be fused to or operatively linked to one of the before-mentioned ketolase-encoding genes to create a contemplated chimeric polypeptide conjugate that is heterologous to the transformed plant. The petunia hybrida (MP4-G) transit peptide gene that encodes a 72 codon (216 bp) transit peptide of EPSP synthase as disclosed by Shah et al., *Science*, 233:478–481 (1986) can also be used.

A particularly preferred plastid transit peptide is a modified version of the ribulose bis-phosphate carboxylase-oxygenase (RUBISCO; RBSC) signal (transit) peptide of tobacco (Nicotiana tabacum)-reported by Mazur et al., *Nucl. Acids Res.*, 13:2343–2386 (1985). Frequent modifications in the gene introduce an NcoI site at the 5' terminus and a NarI site that cleaves between bases 73 and 74. Neither modification alters the amino acid residue sequence.

The resulting plastid transit peptide gene contains 177 base pairs (bp). This gene is preferably utilized as a 177 bp Sal I-Sph I fragment that can be ligated to a before-described ketolase gene. Such ligation creates a gene (about 900 to about 1200 bp) that encodes a heterologous (chimeric) polypeptide having an N-terminal transit peptide whose C-terminus is linked to the N-terminus of a polypeptide that exhibits ketolase activity. Plasmid pATC1616 (ATCC 40806) deposited in connection with Hauptmann et al. U.S. Pat. No. 5,618,988 contains a Sal I-Sph I 177 bp DNA that encodes the RUBISCO transit peptide.

A contemplated DNA sequence (transgene) not only encodes a contemplated chimeric polypeptide, but also includes control sequences that include a promoter that directs or controls expression of the chimer in the designated flower parts, and also preferably includes a termination/polyadenylation sequence that follows the chimer-encoding sequence; i.e., is down stream from or is 3' to the chimer-encoding sequence. Preferential expression in a flower part or site-specific expression such as the in the petals or other reproductive flower parts can be controlled by the promoter that is used. Such a promoter is referred to herein as a promoter for petal-preferred expression.

Exemplary petal-preferred expression can be obtained by use of the so-called petunia chalcone synthase (CHS) gene that works strongly only in the petals (van der Meer et al., *Plant Mol. Biol.*, 15:95–109, 1990). Additional promoters of interest can include the about 1 kilobase (kb) segment that is 5' upstream of the Clarkia breweri linalool synthase 1 (LIS1) gene [See Cseke et al., *Mol. Biol. Evol.*, 15(11): 1491–1498 (1998)],the promoter for APETALA 3 [See Hill et al., *Development* 125: 1711–1721 (1998)] and a petal-preferred plant promoter from *Brassica napus* (See Institut National De La Recherche Agronomique INRA, Fr 2768746). In addition, constitutive promoters for transcription of the foreign gene can be controlled by a plant promoter or by a viral promoter, such as a Cauliflower Mosaic Virus (CaMV) 35S promoter and its derivative, the enhanced 35S version ("E35S"), a Figwort Mosaic Virus promoter, and the like. [See Gruber et al., "Vectors for Plant Transformation," in *Methods in Plant Molecular Biology and Biotechnology*, Glick et al. (eds.), CRC Press, 89–119 (1993); Odell et al., *Nature* 313:810 (1985); and Kay et al., *Science* 236:1299 (1987).] The polyubiquitin gene promoters from *Arabidopsis thaliana*, UBQ3, UBQ10 and UBQ11, are useful for directing gene expression in the petal. [See Norris et al., *Plant Molecular Biology* 21: 895–906 (1993)). The LIS1 or UBQ promoters are preferred herein.

The LIS1 promoter is flower-preferred, whereas the UBQ3 promoter is constitutive. In both cases, a desired 4-keto-β-ionene ring carotenoid compound accumulates in flower parts. In the case of the LIS1 promoter, the reason for flower part accumulation is understood to be that that is the place of expression by the promoter. In the case of the constitutive UBQ31 promoter, a desired 4-keto-β-ionene ring carotenoid compound accumulates in flower parts because the carotenoid substrate for the enzyme is located in the flower parts, rather than throughout the plant.

Figure 1:
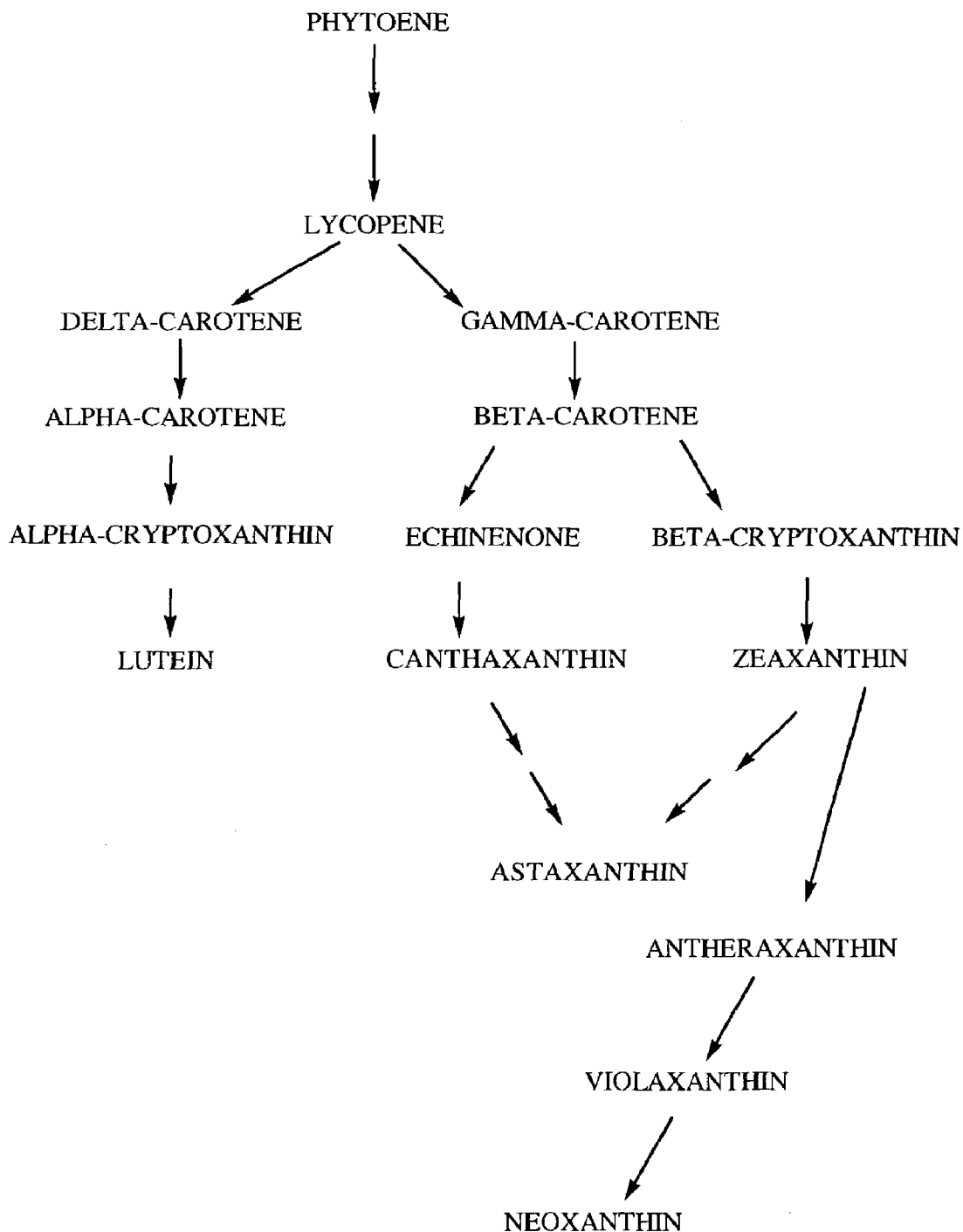
FIG. 1 is a simplified schematic representation of the biological synthesis pathway for the production of lutein, astaxanthin and other xanthophylls in which phytoene, the first $C_{40}$ carotenoid in the pathway, is converted in several steps (two arrows) to lycopene after which the pathway splits to form δ-carotene that contains one ε-ring, then α-carotene that contains one ε-ring and one β-ring, and then α-cryptoxanthin to lutein; or to form γ-carotene that contains one β-ring then β-carotene that contains two β-rings. After β-carotene the pathway branches to form β-cryptoxanthin then zeaxanthin that continues either to the epoxide-containing xanthophylls antheraxanthin, violaxanthin and neoxanthin, or through an additional step (two arrows) to astaxanthin. Through the alternate branch, β-carotene is converted to echinenone then canthaxanthin and with one additional step (two arrows) to astaxanthin.

As is shown in FIG. 1, a desired 4-keto-β-ionene ring carotenoid compound such as astaxanthin is a product that is formed after several steps in a carotenoid synthesis pathway have been completed. Those necessary steps are typically completed only in the flower parts of a contemplated host plant. Thus, expression of the 4-keto-β-ionene ring carotenoid compound-forming enzyme only in the flower parts is unnecessary because expression of that enzyme elsewhere in the plant does not lead to formation of a 4-keto-β-ionene ring carotenoid compound product in that the necessary precursor substrates and enzymes are substantially absent in parts of the plant other than the flowers.

Each of the promoter sequences utilized is substantially unaffected by the amount of carotenoid in the cell. As used herein, the term "substantially unaffected" means that the promoter is not responsive to direct feedback control (inhibition) by the carotenoids accumulated in transformed cells or transgenic plants.

Termination/polyadenylation sequences are also well known. Exemplary termination/polyadenylation sequences that can be used here include the 3' termination sequence from *Agrobacterium* Ti-DNA that encodes nopaline synthase (nos), as well as the 3'sequence from octopine synthase (ocs), the CaMV 35S RNA gene, the termination sequence from β-conglycinin, chalcone synthase, and the small subunit of RUBISCO. [See U.S. Pat. No. 5,618,988; Fujiwara et al., *Plant Mol. Biol.*, 20:1059 (1992); van den Meer et al., *Plant Cell*, 4:253 (1992); Tieman et al., *Plant Cell*, 4:667 (1992); and Mazur et al., *Nucleic Acids Res.*, 13(7):2373–2386 (1985).] The nos sequence is one particularly preferred 3' termination sequence.

A preferred embodiment of the present invention includes a DNA that encodes the chimeric ketolase enzyme polypeptide conjugate operatively linked to a DNA segment that directs marigold flower petal expression. Marigold petals produce β-carotene and are natural sources of zeaxanthin and lutein, and thus could provide a good host for astaxanthin production if the amount of β-carotene or zeaxanthin present were sufficient to provide a meaningful amount of astaxanthin. However, marigolds that are commercially available contain only about 5 to about 7 percent zeaxanthin, about 90 or more percent lutein and less than about 1 percent β-carotene. Such plants are inappropriate hosts because of the relatively low amount of zeaxanthin or β-carotene present in the petals.

Marigolds that have abnormally greater (enhanced) percentages of zeaxanthin to lutein than the normal strains or have almost all zeaxanthin (with little to no lutein), or high concentrations of β-carotene have been grown through selective cross-breeding of mutagenized seeds, and are exemplified hereinafter. These mutant marigold plants having a high percentage of zeaxanthin relative to lutein are one,preferred host plant for the insertion of DNA that encodes a carotenoid β-ionene ring ketolase. Another marigold mutant that is a preferred host plant for insertion of DNA that encodes a carotenoid β-ketolase exhibits an abnormally high β-carotene to lutein ratio.

Illustrative host mutant or transformed marigold plants prior to ketolase gene transformation have marigold flower petals that contain a zeaxanthin ratio greater than about 1:10 and preferably greater than about 2:10. More preferably, zeaxanthin is at least about 70 percent, and most preferably at least about 90 percent, of the xanthophylls. Zeaxanthin can thus be present in contemplated flower petals at about a 10-fold to about a 20-fold enhancement relative to that present in a non-mutant or non-transformed plant of the same type. The zeaxanthin and lutein are typically present in the flower petals as fatty acid esters, although significant amounts of free zeaxanthin have been isolated from the flower petals of several mutant marigold plants. In another embodiment, the host mutant or transformed marigold plant exhibits a β-carotene ratio that is greater than at least about 1:10, more preferably greater than about 2:10, and up to about 1 (one). β-carotene can thus be present at about 5- to about 200-fold enhancement relative to that present in a non-mutant or non-transformed plant of the same type. In a further embodiment, one or both of zeaxanthin and β-carotene can be enhanced to one or both of the extents discussed above relative to those amounts present in a non-mutant or non-transformed plant of the same type.

The petals of a contemplated host plant often contain a measurable amount of zeta-carotene, typically at least 1 percent or more prior to transformation. Zeta-carotene is not normally found in marigold petals and its presence is an example of abnormal expression of one or more carotenoid pigments.

The "zeaxanthin ratio" is defined as the quantity of zeaxanthin present in a flower petal divided by the quantity of zeaxanthin plus lutein [zeaxanthin/(lutein+zeaxanthin)] present in that petal. The usual zeaxanthin ratio in marigold petals is on the order of about 1:15 to about 1:25, so that when only zeaxanthin and lutein amounts are used for calculations, zeaxanthin is about 5 to about 7 percent of the amount of lutein plus zeaxanthin. A preferred zeaxanthin ratio in petals contemplated here is even larger, being greater than about 1:10 and preferably greater than about 2:10, on up to about 1 (one).

An article by Quackenbush et al., *J. Assoc. Off. Agri. Chem.*, 55:617–621 (1972) reported a zeaxanthin to lutein ratio in one group of American yellow T. erecta marigold flower petals that was unusually high at about 1:4.4, whereas the total concentration of xanthophylls in those petals was unusually low at about 0.4 mg/g dry weight. A Mexican variety was said by those authors to contain 11.1 percent zeaxanthin when lyophilized petals were assayed and 3.8 percent when fresh petals were assayed. The higher value is not in keeping with the remainder of the data and is believed to be incorrect.

The "β-carotene ratio" is similarly defined; i.e., β-carotene/(lutein+β-carotene), as are any other "ratios" mentioned herein. The β-carotene ratio in non-mutant plants is typically about less than 0.007 for flower petals. In a contemplated mutant marigold, that ratio is about 1:10 and preferably greater than about 2:10 in petals. More preferably still, a contemplated marigold plant has flower petals that contain a β-carotene ratio greater than about 3:10. Most preferably, that ratio is greater than 5:10, and can be about 1 (one).

Those quantities are determined by high performance liquid chromatography (HPLC) after saponification of a flower petal extract as discussed hereinafter so that each of lutein and zeaxanthin is measured in the alcohol form present after saponification rather than in the esterified form that is present in the fresh flower petal. A standard analytical method used in the industry for determining carotenoid levels in plant extracts is that of the AOAC 1984, *Official Methods of Analysis* (14$^{th}$ ed), the Association of Official Analytical Chemists, Arlington, Va., USA, the results of whose assays are similar to those obtained herein.

A contemplated marigold plant is a mutant of a parental line. That is, a first line or cross or seed is treated with a mutagen (mutagenized) to provide a mutagenized plant that is typically self-pollinated (selfed) one or more times. A plant contemplated herein can arise from the mutagenesis itself, from one of the selfings or from a cross of a mutagenized plant or offspring with another mutagenized or non-mutagenized plant. Such plants are thus of the same type.

Substantially any kind of mutagen can be used to produce a contemplated plant, and exemplary mutagens are discussed hereinafter. Although some contemplated mutant marigolds have a phenotype that is substantially different from that of adjacently-grown non-mutant marigold parental plant, other contemplated mutants exhibit substantially the same phenotype as that of an adjacently-grown non-mutant parental plant, except for phenotypic traits related to carotenoids. More specifically for the latter plants, when one compares plant properties such as plant height, plant diameter, flower head diameter, flower head height, time to flowering, branching amount, length of branches, flower stalk length, hypocotyl length, cotyledon length and cotyledon width between a parent and a mutant plant, the values of those properties for some contemplated mutant plants are each within about 90 percent of those of the parental plant, including the standard deviations in the measurements. More preferably, the values for those properties of the mutant are within about 95 percent of the parent, and most preferably, the values are the same, within the standard deviation. On the other hand, other mutant plants differ greatly in one or more phenotypic traits.

A carotenoid-related phenotypic difference between the parental and mutant plants is the quantity of xanthophyll or carotene pigment that can be obtained from the flowers of the mutant. Parental plants such as 'Scarletade' or 'Deep Orangeade' typically have about 10 to about 18 mg/g dry whole flower head weight of extractable xanthophyll pigments and contain very little carotenes. A contemplated mutant plant having a high zeaxanthin ratio preferably contains about the same amount of carotenoid in the flower petals, but can contain as little as about 4 mg/g dry weight, particularly where the ratio of zeaxanthin to lutein is very high such as about 9:1 or greater. Other mutants can contain little xanthophylls and a relatively large amount of one or more carotenes. As noted before, β-carotene is usually absent from marigold petals.

Phenotypic comparisons are made between adjacently-grown plants. As used herein, the term "adjacently-grown" is used to mean plants grown under as similar conditions of light, heat, growth medium, humidity and nutrients as can be achieved so that growth conditions do not govern the phenotype. For greenhouse-grown plants, "adjacently-grown" means plants grown under conditions as similar as possible on the same bench. For field-grown plants, "adjacently-grown" means plants grown under conditions as similar as possible in the same or adjoining fields.

Mutagenic agents useful for altering plants are well known in the art, as are methods of using such agents. Exemplary chemical mutagens include nitrosomethylurea (NMU), ethyl methanesulfonate (EMS), methyl methanesulfonate, diethyl sulfate, nitrosoguanidine, and ethylnitrosourea of which EMS is preferred herein. NMU can be used as discussed in Cetl et al., *Folia Fac. Sci. Nat. Univ. Purkynianae Brun. Biol.*, 21(1): 5–56 (1980), whereas EMS is typically utilized at about 0.25 to about 1 percent by volume (v/v), and preferably at about 0.2 to about 0.8 percent. Gamma irradiation is also a useful mutagenic agent when used to irradiate seeds at a dose of 200 to about 20,000 rads (0.2 to about 20 krads).

In addition to chemical mutants, plants can also be mutated using ionizing radiation as by gamma rays or neutrons and also by recombinant DNA techniques. Thus, ionizing radiation and recombinant DNA techniques such as gene silencing can also be used to effect alterations in carotenoid profiles. These plants can be thus referred to as chemically-induced, ionizing radiation-induced and recombinantly-induced mutants, respectively. As a consequence, a mutant host plant such as a preferred marigold is defined herein as a marigold plant obtained by chemically-induced mutation, ionizing radiation-induced mutation or recombinantly-induced mutation.

Thus, gamma rays and fast neutron bombardment have been used for other plants to cause deletions of one or more genes. Gene silencing can be effected by over expression of a sense strand of a gene that leads to down-regulation via a mechanism referred to as co-suppression. Down regulation can also be achieved by expression of antisense genes for one or more enzymes present in a carotenoid-production pathway. Still further techniques are well known to workers skilled in this art.

Regardless of the mutagen used, the phenotype of most of the resulting mutant plants, including carotenoid-related traits such as the zeaxanthin ratio, and the amount of xanthophylls in the petals, is usually substantially identical to that of the parent, so that a very large percentage of the mutants obtained are not useful. In addition, plants seeming to have the same phenotype as the parent need to be screened to locate a desired mutant plant. Those screenings, although tedious, are routinely carried out and involve analysis of carotenoid pigments from one or more single flower petals or leaves or both. Thus, the preparation of a desired mutant is a relatively rare, but repeatable event. For example, in one study herein, only twenty-three useful mutants were obtained from almost 22,000 mutant plants examined that had zeaxanthin ratios of about 1:10 or more, and only two plants out of those twenty-three had zeaxanthin ratios greater than about 9:1. In another study, about 43 mutants out of about 8200 examined plants exhibited zeaxanthin ratios of about 1:10 or greater.

As already noted, a contemplated plant can be a plant that grows from the mutagenized seed or can be a selfing or cross. In one preferred embodiment, a contemplated plant host such as a marigold is a hybrid formed by crossing the flowers of two plants that arose from two different mutagenized plants from independent $M_1$ plants ($M_1 \times M_1$). In another embodiment, a contemplated marigold host is a hybrid formed by crossing the flowers of one plant that arose from one mutagenized plant with a non-mutagenized plant. In still another embodiment, a contemplated plant is a hybrid formed by back-crossing a hybrid with one or the other of its immediate parental flowers. The product of the crossing of two different hybrid plants is contemplated as is the product of the selfing of a hybrid.

As has already been mentioned, a contemplated host plant can itself be an immediate product of a mutation event, such as a product of the seed produced after the mutation process. That plant can also be a product of one or more crosses of one mutant with another or of mutant selfings. A contemplated plant can also be the result of a cross between mutant and non-mutant parental plants. The produced plants are screened and selected for desired carotenoid characteristics.

A contemplated host plant can be a plant that grows from the mutagenized seed or can be a selfing or cross. In one preferred embodiment, a contemplated marigold is an $F_1$ hybrid formed by crossing the flowers of two plants that arose from two different mutagenized plants ($M_1 \times M_1$). In another embodiment, a contemplated marigold is an $F_1$ hybrid formed by crossing the flowers of one plant that arose from one mutagenized plant with a non-mutagenized plant. In still another embodiment, a contemplated plant is a hybrid formed by back-crossing an $F_1$ hybrid with one or the other of its immediate parental flowers. The product of the crossing of two different $F_1$ hybrid plants is contemplated as is the product of the selfing of a $F_1$ hybrid.

The use of marigold plant mutants that have β-carotene- or zeaxanthin-rich petals as host plants for transformation to produce one or both of canthaxanthin and astaxanthin is commercially viable and efficient. The marigold provides a host that is economically advantageous because of the wide experience had in the art of growing such plants for the production of lutein. A transgenic marigold also provides a cost efficient source for easily isolated astaxanthin.

In another embodiment, the present invention relates to the insertion of a DNA segments encoding a chimeric ketolase enzyme polypeptide conjugate and the insertion of a DNA segment encoding a chimeric hydroxylase enzyme peptide conjugate, both of which enzymes utilize a carotenoid β-ionene ring as substrate as already discussed herein for the production of a 4-keto β-ionene ring and a 3-hydroxy β-ionene ring, respectively. The DNA that encodes each of the ketolase and the hydroxylase is separately operatively linked to a flower petal-preferred promoter.

Exemplary genes (crtZ) that encode useful hydroxylase enzymes from *E. urodovora* (See U.S. Pat. No. 5,429,939), *E. herbicola* (See U.S. Pat. No. 5,684,238), *H. pluvialis* (See U.S. Pat. Nos. 5,811,273 and No. 5,972,690), as well as *Agrobacterium aurantiacum* and *Alcaligenes* sp. strain PC-1 [See Misawa, et al., *J. Bacteriol.*, 177:6575–6584 (1995)] have been previously discussed.

The hydroxylase and ketolase enzymes such, as those discussed above can be inserted into a higher plant whose flower petals produce an appropriate carotenoid precursor that contains a β-ionene ring such as β-carotene. A non-higher plant hydroxylase is preferred in some embodiments. The β-carotene can then be converted to astaxanthin. At least eight β-ionene ring-containing carotenoid compounds that include zeaxanthin, β-cryptoxanthin, adonixanthin, 3-hydroxyechinenone, 3'-hydroxyechinenone, echinenone, canthaxanthin, and adonirubuin can be intermediates between β-carotene and astaxanthin.

Hydroxylase and ketolase chimeric enzymes whose expression is controlled by a flower petal-preferred promoter can result in the production of canthaxanthin and then astaxanthin in the flower petals of higher plants. Canthaxanthin and astaxanthin result from the conversion of β-carotene or other carotenoid precursors through various carotenoids to 4-keto-β-ionene ring-containing carotenoid compounds and then to 3-hydroxy-4-keto-β-ionene ring-containing carotenoid compounds. Because the hydroxylase and ketolase enzymes are from species other than the higher plant host, the phenomenon of co-suppression that can be observed when a transformed gene is the same as is already present in the host plant is not observed.

A different aspect of the invention includes a transgenic plant whose flowers do not normally exhibit production of carotenoids (i.e., the flowers of a "normal", non-transgenic plant do not produce appreciable beta-carotene and its family of carotenoids), the vinca and the lisianthus being examples of such plants. A group or cluster of genes that encodes enzymes that catalyze the production of carotenoid intermediates, canthaxanthin and astaxanthin from common precursors can be transformed into such plants so that the flower petals produce astaxanthin. The gene group includes enzymes sufficient to produce beta-carotene, as well as one or both of a hydroxylase and a ketolase to transform the beta-carotene into zeaxanthin, or canthaxanthin and to astaxanthin.

The above-described gene group includes genes that encode a ketolase, and a hydroxylase as discussed before, as well as genes that encode enzymes that transform ubiquitous precursors such as geranyl pyrophosphate and farnesyl pyrophosphate into GGPP, and GGPP into β-carotene. Ausich et al. U.S. Pat. No. 5,684,238, discloses appropriate methods, *E. herbicola* nucleic acid sequences and deposited *E. herbicola* DNA-containing cells for the formation of GGPP and the conversion of GGPP into phytoene, phytoene into lycopene and lycopene into beta-carotene in a transformed host plant. That patent also teaches methods, *E. herbicola* nucleic acid sequences and deposited *E. herbicola* DNA-containing cells for the conversion of β-carotene into zeaxanthin in a host plant. Transformation of a host plant to express each of those genes and also a before-described ketolase gene, each gene encoding a chimeric enzyme containing an N-terminal transit peptide sequence, provides a transgenic plant that produces astaxanthin in flower petals.

More specifically, a DNA segment comprising a nucleotide sequence that contains at least 850 base pairs that define a structural gene for the *Erwinia herbicola* enzyme geranylgeranyl pyrophosphate synthase can be utilized for the production of GGPP. Illustrative DNA segments are present in a plasmid selected from the group consisting of pARC417BH having ATCC Accession No. 40755, pARC489B having ATCC Accession No. 40758 and pARC489D having ATCC Accession No. 40757.

A DNA segment comprising a nucleotide sequence that contains at least 1000 base pairs that define a structural gene for the *Erwinia herbicola* enzyme phytoene synthase can be used as another gene in the group for the production of lycopene. Illustrative DNA segments are present in plasmid pARC285 having ATCC Accession No. 40756 or plasmid pARC140N having ATCC Accession No. 40754.

A DNA segment comprising a nucleotide sequence encoding the structural gene for the *Erwinia herbicola* enzyme phytoene dehydrogenase-4H is also useful for the production of lycopene. Illustrative DNA segments are present in a plasmid selected from the group consisting of pARC496A having ATCC accession No. 40803, pARC146D having ATCC accession No. 40801, pATC228 having ATCC accession No. 40802, and pATC1616 having ATCC accession No. 40806.

A DNA segment comprising a nucleotide sequence encoding the structural gene for the *Erwinia herbicola* enzyme lycopene cyclase can be used for the preparation of β-carotene. Exemplary DNA segments are present in a plasmid selected from the group consisting of pARC1509 having ATCC accession No. 40850, pARC1510 having ATCC accession No. 40851, and pARC1520 having ATCC accession No. 40852.

A DNA segment comprising a nucleotide sequence encoding the structural gene for the *Erwinia herbicola* enzyme β-carotene hydroxylase can be used for the preparation of zeaxanthin. Illustrative DNA segments are present in a plasmid selected from the group consisting of pARC406BH, pARC429BH and pARC145H.

A DNA variant of one or more of the above DNA segments that has at least 80 percent identity to one of those genes and hybridizes with that gene under moderately high stringency conditions comprising hybridization at a temperature of about 500° to about 65° C. in 6×SSC and a final wash at a temperature of 68° C. in 1–3×SSC can also be used.

It is to be understood that each of the above-discussed *E. herbicola* genes or variants encodes a chimer enzyme that contains an N-terminal transit peptide as discussed previously, and each gene is controlled by a promoter that provides petal-preferred expression of the chimer as was also discussed before.

It is also to be understood that a DNA sequence of an appropriate gene from *E. uredovora, A. aurantiacum, Alcaligenes* sp. *A. aurantiacum* and *Alcaligenes* sp. or *Rhodobacter capsulatus* as discussed previously, or a variant discussed as above, that encodes a chimeric enzyme having an N-terminal plastid transit peptide can be used in place of a DNA sequence from *E. herbicola*. A host plant can also contain mixtures of genes whose sequences correspond to genes from a plurality of sources.

Where a plant does not normally produce colored carotenoids in its petals; i.e., a non-transformed plant, it is preferred to utilize a flower-specific promoter rather than a constitutive promoter to direct expression of the colored carotenoid. It is thus preferred to use a flower-specific promoter for the expression of enzymes that catalyze the production of lycopene, beta-carotene, gamma-carotene and the xanthins, although the 4-keto-β-ionene ring-producing enzyme can be expressed using a constitutive promoter, as already discussed.

A recombinant DNA molecule comprising a vector operatively linked to heterologous genomic DNA sequence (transgene) that (a) encodes a chimeric ketolase enzyme and (b) contains a promoter that directs expression of the chimeric enzyme. The chimeric ketolase enzyme is comprised of (i) a N-terminal first portion comprising a plastid transit peptide portion fused to (ii) a second, ketolase enzyme portion that converts a carotenoid β-ionene ring into a carotenoid 4-keto-β-ionene ring. The promoter and the plastid transit peptide are preferably from different species. The result of expression of the transgene in a contemplated plant is flower-preferred accumulation of a 4-keto-β-ionene ring carotenoid compound. The structural gene has a nucleotide base sequence discussed before.

In living organisms, the amino acid residue sequence of a protein or polypeptide is directly related via the genetic code to the deoxyribonucleic acid (DNA) sequence of the structural gene that codes for the protein. A structural gene can be defined in terms of the amino acid residue sequence; i.e., protein or polypeptide, for which it codes.

Thus, through the well-known redundancy of the genetic code, additional DNA and corresponding RNA sequences can be prepared that encode the same amino acid residue sequences, but are sufficiently different from a before-discussed gene sequence that the two sequences do not hybridize at high stringency, but do hybridize at moderately high stringency. Thus, for example, in vitro mutagenesis can be used to change a DNA sequence so that the same residue of the expressed enzyme is expressed using one or more different codons. In addition, that same technique can be used to change one amino acid residue to another where it is desired to insert or delete specific restriction endonuclease sites. Furthermore, allelic variants of a structural gene can exist in other organisms that are also useful, but form hybrid duplex molecules only at moderately high stringency.

A DNA segment that includes a DNA sequence encoding a promoter operatively linked to DNA that encodes a plastid transit peptide whose DNA is linked to the 5' of a DNA segment that encodes a ketolase or other contemplated enzyme can be prepared by excising and operatively linking appropriate restriction fragments from deposited plasmids or by PCR from those DNAs discussed elsewhere herein using well known methods. The DNA molecules useful here that are produced in this manner typically have cohesive termini; i.e., "overhanging" single-stranded portions that extend beyond the double-stranded portion of the molecule. The presence of cohesive termini on the DNA molecules useful in the present invention is preferred, although molecules having blunt termini are also contemplated.

A recombinant DNA molecule useful herein can be produced by operatively linking a vector to contemplated isolated DNA segment to form a plasmid such as those discussed herein. Particularly preferred recombinant DNA molecules are discussed in detail in the examples, hereafter. Vectors capable of directing the expression of the gene are referred to herein as "expression vectors".

The expression vectors described above contain expression control elements including the promoter. The chimeric polypeptide coding genes are operatively linked to the expression vector to permit the promoter sequence to control RNA polymerase binding and expression of the desired polypeptide coding gene. Useful in expressing the polypeptide coding gene are promoters that are inducible, viral, synthetic, constitutive as described by Poszkowski et al., *EMBO J.*, 3:2719 (1989) and Odell et al., *Nature,* 313:810 (1985), and temporally regulated, spatially regulated, and spatiotemporally regulated as given in Chua et al., *Science,* 244:174–181 (1989).

The choice of which expression vector and ultimately to which preselected promoter a polypeptide-coding gene is operatively linked depends directly on the functional properties desired, e.g. expression efficiency, the location and timing of protein expression, and the host cell to be transformed. These are well known limitations inherent in the art of constructing recombinant DNA molecules. However, a vector useful in practicing the present invention integrates into the genome of the host higher plant, is capable of directing the replication, and also the expression of the chimeric polypeptide coding gene included in the DNA segment to which it is operatively linked. It is well known that the entire expression vector does not integrate into the host plant genome, but only a portion integrates. Nonetheless, the vector will be said to integrate for ease of expression.

In one preferred embodiment, a vector includes a prokaryotic replicon; i.e., a DNA sequence having the ability to direct autonomous replication and maintenance of the recombinant DNA molecule extrachromosomally in a prokaryotic host cell transformed therewith. Such replicons are well known in the art.

Those vectors that include a prokaryotic replicon can also include a prokaryotic promoter region capable of directing the expression of the phytoene synthase conjugate gene in a host cell, such as *E. coli,* transformed therewith. Promoter sequences compatible with bacterial hosts are typically provided in plasmid vectors containing one or more convenient restriction sites for insertion of a DNA segment of the present invention. Typical of such vector plasmids are pUC18, pUC19, and pBR322 available from Gibco BRL, Gaithersburg, Md., and pPL and pKK223–3 available from Pharmacia, Piscataway, N.J. These vectors can be utilized in the synthesis of the DNA segments present in the integrating expression vectors.

Typical vectors useful for expression of genes in higher plants are well known in the art and include vectors derived from the tumor-inducing (Ti) plasmid of *Agrobacterium tumefaciens* described by Rogers et al., *Meth. in Enzyymol.,* 153:253–277 (1987). These vectors are plant-integrating vectors in that on transformation, the vectors integrate a portion of vector DNA into the genome of the host plant. For integrating vectors based on the Ti plasmid, the region integrated into the host plant chromosomes is that between the right and left borders of the Ti plasmid.

Exemplary *A. tumefaciens* vectors useful herein are plasmids pKYLX6 and pKYLX7 of Schardl et al., *Gene,* 61:1–11 (1987) and Berger et al., *Proc. Natl. Acad. Sci. U.S.A.,* 86:8402–8406 (1989). Plasmid pKYLX6 is an *E. coli* vector designed for intermediate constructs, whereas plasmid pKYLX7 is an *A. tumefaciens* vector designed for integration of cloned genes. Modified vectors pKYLX61 and pKYLX71 contain Hind III, Xho I, BamH I, Pst I and Sst I sites in place of the original Hind III-Sst I fragment multiple cloning site region. Another useful vector herein is plasmid pBI101.2 that is available from Clontech Laboratories, Inc., Palo Alto, Calif. Plasmids pKYLX7, pKYLX71 and pB7101.2 are binary vectors that are used in *A. tumefaciens* with another vector having a vir gene.

Another plant transformation system is based on *Agrobacterium rhizogenes* that induces hairy roots rather than a tumor on transformation. Application PCT/US87/02512 (WO 88/02405 published Apr. 7, 1988) describes the use of *A. rhizogenes* strain A4 and its Ri plasmid along with *A. tumefaciens* vectors pARC8 or pARC16 to transform the cucumber Cucumis sativas L., cv, Straight Eight, and form regenerated cucumber plants.

The use of retroviral expression vectors to form the recombinant DNAs of the present invention is also contemplated. As used herein, the term "retroviral expression vector" refers to a DNA molecule that includes a promoter sequence derived from the long terminal repeat (LTR) region of a retrovirus genome. Because some of these carotenoid products can be associated with food production and coloration, the retroviral expression vector is preferably replication-incompetent in eukaryotic cells. The construction and use of retroviral vectors have been described by Verma, PCT Publication No. WO 87/00551, and by Cocking et al, *Science,* 236:1259–62 (1987).

In preferred embodiments, the vector used to express the chimer-coding gene includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described by Rogers et al., in *Methods For Plant Molecular Biology,* A. Weissbach and H. Weissbach, eds., Academic Press Inc., San Diego, Calif. (1988). Another preferred marker is the assayable chloramphenicol acetyltransferase (CAT) gene from the transposon Tn9.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the integrating expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an integrating expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above-described recombinant DNA molecules.

Methods for introducing polypeptide-coding genes into higher, multicelled flowering plants include *Agrobacterium*-mediated plant and callus transformation, protoplast transformation, gene transfer into pollen, injection into reproductive organs and injection into immature embryos. Each of these methods has distinct advantages and disadvantages. Thus, one particular method of introducing genes into a particular plant species may not necessarily be the most effective for another plant species, but it is well known which methods are useful for a particular plant species.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated expression vectors to introduce DNA into plant cells via Ti-DNA is well known in the art. See; for example, the methods described by Fraley et al., *Biotechnology,* 3:629 (1985) and Rogers et al., *Methods in Enzymology,* 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.,* 205:34 (1986) and Jorgensen et al., *Mol. Gen. Genet.,* 207:471 (1987).

Modern *Agrobacterium* transformation vectors such as those discussed before are capable of replication in *E. coli* as well as *Agrobacterium*, permitting convenient manipulations as described by Klee et al., in *Plant DNA Infectious Agents,* T. Hohn and J. Schell, eds., Springer-Verlag, N.Y. (1985) pp. 179–203.

Moreover, recent technological advances in vectors for, *Agrobacterium*-mediated gene transfer have improved the arrangement of genes and restriction sites in the vectors to facilitate construction of vectors capable of expressing various polypeptide-coding genes. The vectors described by Rogers et al., *Methods in Enzymology,* 153:253 (1987), have convenient multi-linker regions flanked by a promoter and a polyadenylation site for direct expression of inserted polypeptide coding genes and are suitable for present purposes.

In those plant species where *Agrobacterium*-mediated transformation is efficient, it is often the method of choice because of the facile and defined nature of the gene transfer. However, few monocots appear to be natural hosts for *Agrobacterium*, although transgenic plants have been produced in asparagus using *Agrobacterium* vectors as described by Bytebier et al., *Proc. Natl. Acad. Sci. U.S.A.,* 84:5345 (1987).

*Agrobacterium*-mediated transformation of leaf disks and other tissues such as callus appears to be limited to plant species that *Agrobacterium* naturally infects. *Agrobacterium*-mediated transformation is therefore most efficient in dicotyledonous plants. However, as mentioned above, the transformation of asparagus using *Agrobacterium* can also be achieved.

Transformation of plant protoplasts can be achieved using methods based on calcium phosphate precipitation, polyethylene glycol treatment, electroporation, and combinations of these treatments. [See for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimiya et al., *Mol. Gen. Genet.*, 204:204 (1986); Callis et al., *Genes and Development*, 1:1183 (1987); Marcotte et al., *Nature*, 335:454 (1988); Wang et al., *Bio/Technology*, 10:691–696 (1992); and Fennell et al., *Plant Cell Reports*, 11:567–570 (1992).]

Application of these systems to different plant species depends upon the ability to regenerate that particular plant species from protoplasts. To transform plant species that cannot be successfully regenerated from protoplasts, other ways to introduce DNA into intact cells or tissues can be utilized.

For example, "particle gun" or high-velocity microprojectile technology can be utilized. Using such technology, DNA is carried through the cell wall and into the cytoplasm on the surface of small metal particles as described in Klein et al., *Nature*, 327:70 (1987); Klein et al., *Proc. Natl. Acad. Sci. U.S.A.*, 85:8502 (1988); and McCabe et al., *Biotechnology*, 6:923 (1988); and Vasil et al., *Bio/Technology*, 9:667–674 (1992). Metal particles can be coated with all or part of a previously described vector such as a vector usually used for *Agrobacterium*-mediated transformation. Thus, the particle is used to carry the vector into the plant cell rather than the bacterium. Once in the cell, an *Agrobacterium*-mediated transformation vector acts in much the same way it does when used with *Agrobacterium* to effect transformation.

The metal particles penetrate through several layers of cells and thus permit the transformation of cells within tissue explants. Transformation of tissue explants eliminates the need for passage through a protoplast stage and thus speeds the production of transgenic plants.

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide-coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Apl. Genet.*, 75:30 (1987); and Benbrook et al., in *Proceedings Bio Expo. 1986*, Butterworth, Stoneham, Mass., pp. 27–54 (1986).

The regeneration of plants from either single plant protoplasts or various explants is well known in the art. [See for example, *Methods for Plant Molecular Biology*, A. Weissbach and H. Weissbach, eds., Academic Press, Inc., San Diego, Calif. (1988).] This regeneration and growth process includes the steps of selection of transformant cells and shoots, rooting the transformant shoots and growth of the plantlets in soil.

The regeneration of plants containing the foreign gene introduced by *Agrobacterium* from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth.

Transformant shoots that rooted in the presence of the selective agent to form plantlets are then transplanted to soil or other growth media to permit the production of roots. These procedures vary depending upon the particular plant species employed, such variations being well known in the art.

Seed from a cross or selfing as discussed before is also contemplated herein. Such seed, upon planting in a suitable environment and growth to maturity yields a transgenic plant such as a transgenic marigold whose flower petals contain astaxanthin.

The present invention also contemplates the pollen and an ovule of a contemplated transgenic plant. The regenerable portion of a contemplated transgenic plant is also itself contemplated and includes cells selected from the group consisting of embryos, cotyledons, hypocotyls, meristems, pollen, leaves, anthers, roots, root tips, and flowers, or protoplasts or callus derived therefrom. Methods for regenerating plants from cells are well known to those skilled in the art, and dicotyledonous plants such marigolds are particularly susceptible to such regeneration.

Another contemplated aspect of this invention is transgenic flower parts such as marigold flower petals that contain canthaxanthin or astaxanthin, in which astaxanthin is typically present as astaxanthin fatty acid esters of acids such as lauric, palmitic and myristic acids. These flower petals are usually dried and are in comminuted form.

An oleoresin comprised of one or both of canthaxanthin and fatty acid esters of astaxanthin is also contemplated. As is well known in the art, an oleoresin is a solid extract of plant tissues that contains plant pigments such as the canthaxanthin in free, uncombined form and astaxanthin esters here in esterified forms, sometimes accompanied by small amounts of other plant products and pigments such as other xanthophyll esters, as well as small amounts of the extracting solvent such as hexane or acetone. A contemplated transgenic, preferably marigold, oleoresin contains one or both of canthaxanthin and astaxanthin and other xanthophyll fatty acid esters as are present in the petals of a contemplated transgenic plant. Oleoresins are items of commerce and are sold to processors for further treatment in the production of human or other animal food supplements, nutraceuticals, anti-oxidants and the like.

In an illustrative transgenic marigold oleoresin preparation, free xanthophylls and xanthophyll esters, including astaxanthin esters and possibly other xanthophyll esters or carotenes, is extracted from dried transgenic marigold flowers with hexane, acetone, ethyl acetate or the like organic solvent. The extraction is carried out according to procedures known in the art. The solvent(s) is removed, resulting in an extract that contains a high level of the free xanthophyll and xanthophyll esters and is about 99 percent and preferably about 99.9 percent free of the extracting organic solvent; i.e., contains less than about 1 percent and preferably less than about 0.1 percent organic solvent by weight. The resulting solvent-free extract is referred to as a transgenic marigold oleoresin or more as an astaxanthin-containing marigold oleoresin.

A composition suitable for use as a food supplement for human or other animals such as poultry like chickens and turkeys, fish like trout and salmon and crustaceans like shrimp, lobsters and crabs is also contemplated. A contemplated food supplement can be used to provide color to the meat or skin of those animals as well as to the eggs of such animals, and particularly chickens. The food supplement comprises one or more of canthaxanthin and a mixture of fatty acid esters of astaxanthin as are present in a marigold oleoresin, and can contain carotenes and fatty acid esters of other xanthophylls present in that oleoresin. That mixture of fatty acid esters is dissolved or dispersed in a comestible medium. This food supplement can thus be prepared by suitable purification of a before-described oleoresin as by dissolution and filtration, followed by dissolution or dispersion of the purified mixed esters in an appropriate comestible medium such as an edible vegetable oil.

In some embodiments, the comestible medium is an edible triglyceride oil. The 4-keto-β-ionene ring-containing carotenoid (e.g., canthaxanthin or astaxanthin ester-containing xanthophyll ester or both) content of the admixture as free xanthophylls is typically about 0.2 to about 40 percent by weight, and more preferably about 2 to about 20 weight percent. Exemplary edible oils include candelilia, coconut, cod liver, cotton seed, menhaden, olive, palm, corn, soybean, peanut, poppy seed, safflower and sunflower oil. The use of an oil having a relatively high concentration of unsaturated fatty acids is preferred; i.e., the use of an oil having an iodine value of about 100–150 is preferred. The admixture is typically carried out using a high shear mixing apparatus, as is well known. Co-solvents and additives such as ethanol and α-tocopherol, respectively, can also be present as is noted in U.S. Pat. No. 5,382,714.

The 4-keto-β-ionene ring-containing composition (e.g., canthaxanthin, astaxanthin or mixture of both) can also be provided in the form of generally spherical small pellets containing 0.5 to about 20 percent, and preferably about 1 to about 4 percent, of free canthaxanthin, astaxanthin, free astaxanthin-containing xanthophyll, as astaxanthin esters or a mixture of canthaxanthin and astaxanthin-containing xanthophyll esters that are conventionally referred to as "beadlets". These beadlets can be used admixed in a desired amount into human food such as ready to eat cereals as is disclosed in U.S. Pat. No. 5,270,063 or admixed into chicken or other animal feed as are the beadlets or other particles disclosed for the feed additive in U.S. Pat. No. 5,849,345, No. 5,695,794, No. 5,605,699 and No. 5,043,170.

Exemplary beadlets are water-insoluble and are prepared by encapsulation of a 4-keto-β-ionene ring-containing composition by cross-linked gelatin or an alginate such as sodium alginate as is disclosed in U.S. Pat. No. 4,670,247. A water insoluble beadlet containing the desired carotenoid(s) is prepared by forming an emulsion containing the carotenoid(s), water, gelatin, and a sugar. The emulsion is converted into droplets that are individually collected in a mass of starchy powder in such a manner that the particles from the droplets are kept separated from each other until their particulate form is permanently established. The carotenoid-containing particles are separated from the starchy collecting powder, and heat-treated at a temperature of about 90° C. to about 180° C. The heat treatment step insolubilizes the gelatin matrix of the beadlet by a reaction between the carbonyl group of the sugar with the free amino moieties of the gelatin molecule. The resulting beadlets are water-insoluble and exhibit increased stability to the stresses of feed pelleting. The cross-linking process utilizes the ingredients employed in making the beadlet and does not require addition of a cross-linking reagent or additive to the composition.

U.S. Pat. No. 5,695,794 discloses another form of beadlets that can be adapted for use herein as an additive for animal feed. Thus, beadlets having diameters of about 30 to about 55 microns are prepared by spraying a molten solution of a desired amount of astaxanthin-containing xanthophyll esters in hydrogenated vegetable oil such as hydrogenated cotton seed oil, wheat-germ oil, safflower oil, soybean oil and the like, that also can contain mono- and diglycerides such as those prepared from hydrogenated soybean mono- and diglycerides, cottonseed mono- and diglycerides and the like, as well as citric acid and 2,6-di-tert-butyl-4-methylphenol (BHT) as antioxidants. Other antioxidants such as ethoxiquin, vitamin E and the like can also be used, as is well known. The molten mixture is sprayed at a temperature of about 160° F. (about 70° C.) into a cyclonic air stream of a spray chiller such as available from Niro, Inc., Columbia, Md. to produce the beadlets that solidify on cooling. The cooled beadlets are dusted with an anticaking agent such as fumed silica, calcium phosphate, powdered starch or cellulose as are well known to form the beadlets that are preferably added to the feed as supplement. An exemplary beadlet contains about 10 to about 100 milligrams of astaxanthin-containing xanthophyll per gram (mg/g) and preferably at about 10 to about 50 mg/g.

Animal feeds to which a contemplated 4-keto-β-ionene ring-containing carotenoid composition (e.g., canthaxanthin, astaxanthin, mixture of astaxanthin-containing xanthophyll esters or mixture of both) is added are well known in the art. The above-noted U.S. Pat. No. 5,849,345, No. 5,695,794, No. 5,605,699 and No. 5,043,170 provide exemplary diets that are particularly useful for poultry. U.S. Pat. Nos. 5,935,624 and 2,918,370 provide further illustrative poultry diets.

U.S. Pat. No. 5,258,189 teaches the addition of beta-carotene to a ready to eat cereal product for humans in which the beta-carotene is admixed with a cooked cereal product dispersed in a vegetable oil or in dry form. A 4-keto-β-ionene ring-containing carotenoid composition can be used at a desired level in place of beta-carotene in a similar food product.

Another composition suitable for use as a food supplement comprises a 4-keto-β-ionene ring-containing carotenoid composition dissolved or dispersed in a comestible medium. This composition contains one or both of canthaxanthin and hydrolyzed 4-keto-β-ionene ring-containing carotenoid composition such as astaxanthin-containing xanthophylls that are free alcohol (or keto) compounds as compared to the esters that are present in a marigold oleoresin.

Methods are well known for saponifiying marigold oleoresins to provide free xanthophylls. See, for example, Tcyczkowski et al., *Poultry Sci.* 70(3): 651–654, 1991; and U.S. Pat. No. 5,382,714, that crystallized lutein from the saponified marigold oleoresin by the addition of organic solvents.

In addition, Ausich et al. U.S. Pat. No. 5,648,564 teaches the production of crystalline lutein from a marigold oleoresin by admixing the oleoresin with a composition containing propylene glycol and an aqueous alkali, preferably potassium hydroxide, to form a reaction mixture of which oleoresin and propylene glycol together constitute at least 75 weight percent. The reaction mixture so formed is maintained at a temperature of about 65° C. to about 80° C. for a time period (typically at least 3 hours) sufficient to saponify the xanthophyll ester and form a saponified reaction mixture that contains free xanthophyll in the form of crystals. The saponified extract is admixed with a diluting amount of water to dissolve the water-soluble impurities and reduce the viscosity of the reaction mixture. The diluted admixture is gently admixed until homogeneous and then filtered to collect the xanthophyll crystals. The collected xanthophyll crystals are washed with warm water, and dried. No organic solvent other than propylene glycol is used in the isolation and purification of the xanthophyll from the xanthophyll ester-containing oleoresin. The dried xanthophyll crystals so formed are typically admixed with a comestible medium such as the triglyceride discussed above. The xanthophyll content of the admixture is typically about 0.1 to about 35 percent by weight, and preferably about 1 to about 10 percent by weight.

Methods are well known for saponifiying (hydrolyzing) astaxanthin esters to provide the free xanthophyll. See, for example, Kamata and Simpson, *Comp. Biochem. Physiol.* 86B(3):587–591, 1987; and Yuan and Chen, *J. Agric. Food Chem.* 47: 31–35, 1999, that both teach saponification of astaxanthin esters under nitrogen.

For fatty acid analysis, Kamata and Simpson saponified a purified astaxanthin diester from *Adonis aestivalis* using 0.1 N methanolic KOH and heating at 100° C. for 40 minutes under nitrogen. After saponification, 0.5 N HCl was added to acidify the sample and astacene, a structural transformation of astaxanthin, was extracted with petroleum ether.

Yuan and Chen, above, identified a saponification method for the hydrolysis of astaxanthin esters in pigment extract of *Haematococcus pluvialis* without significant degradation or structural transformation of astaxanthin. Complete hydrolysis of astaxanthin esters was achieved in six hours for different concentrations (10–100 mg/l) of pigment extracts using 0.018 M metanolic NaOH under nitrogen in darkness. With a higher concentration of methanolic NaOH solution, the reaction rate of hydrolysis was high, but astaxanthin degradation occurred significantly.

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

Construction of β-Carotene Ketolase (β-Carotene Oxygenase) Expression Vectors

A. β-Carotene Ketolase from *H. pluvialis*

Figure 2:
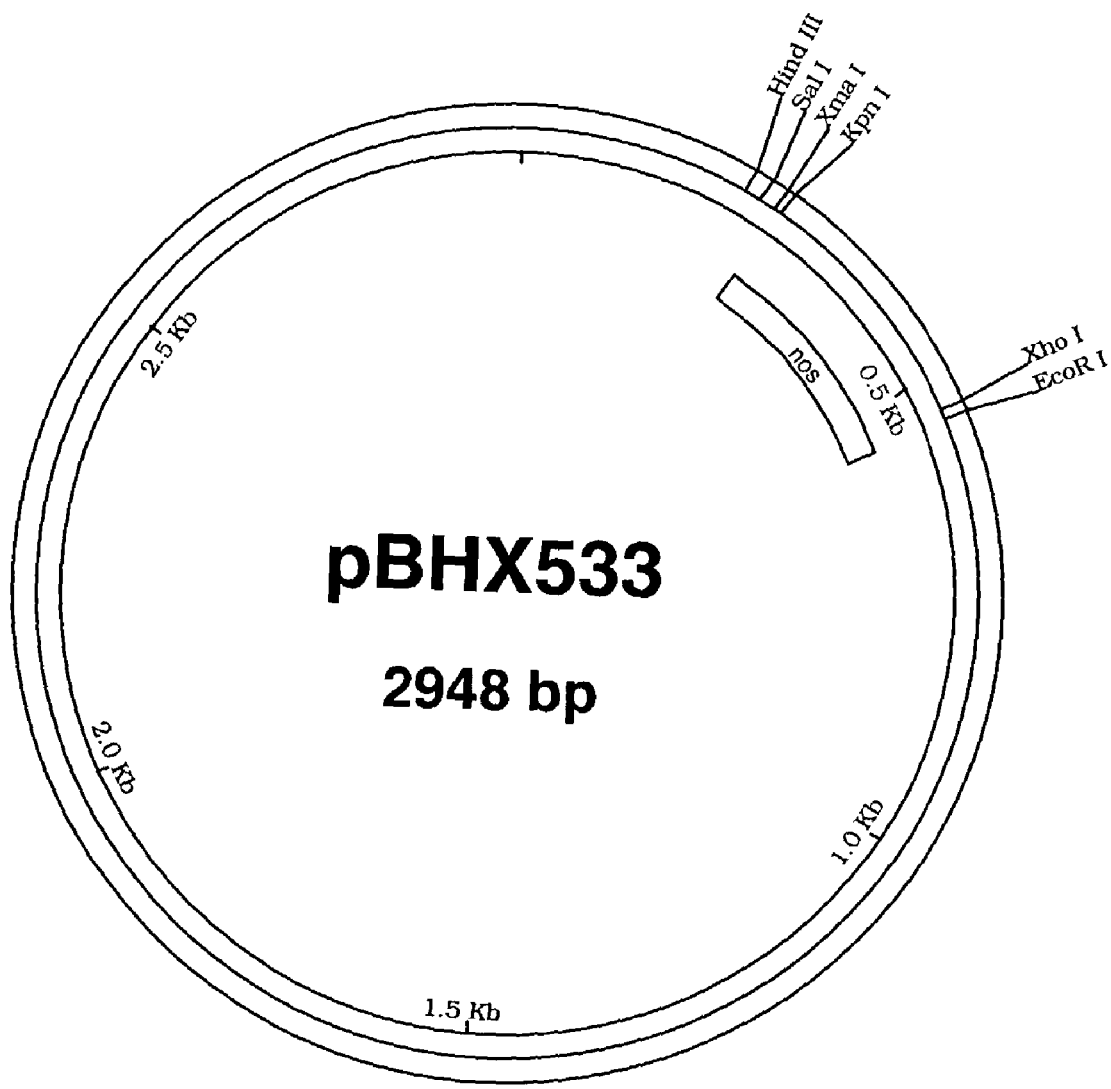
FIG. 2 schematically shows plasmid pBHX533 that contains an approximately 2948 base pair (bp) DNA segment that includes the 3' termination sequence from *Agrobacterium* Ti-DNA that encodes nopaline synthase (nos), as well as several important restriction enzyme sites and their position numbers.
Figure 3:
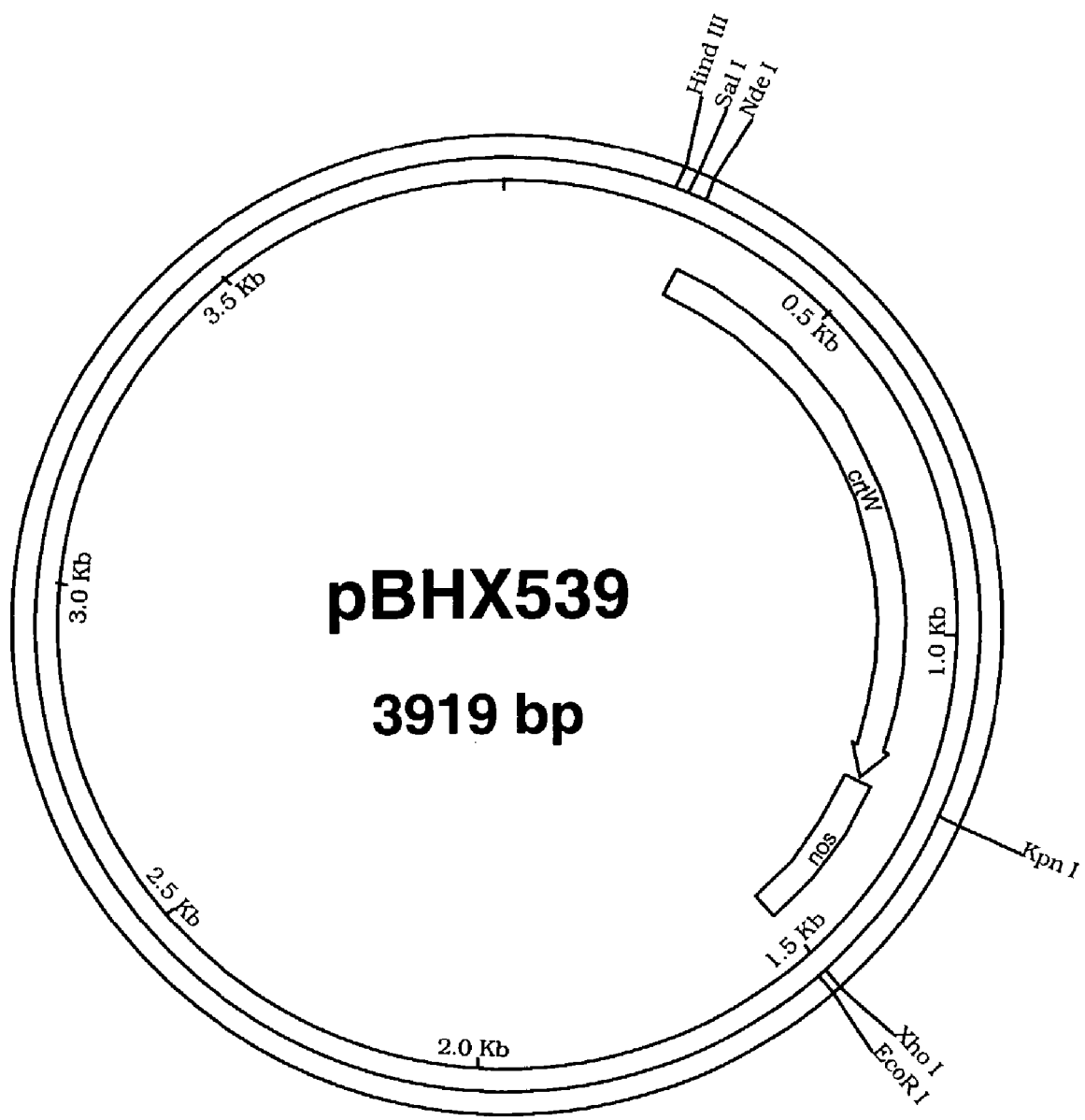
FIG. 3 schematically shows plasmid pBHX539 that contains an approximately 3919 bp DNA segment that includes a sequence that encodes a ketolase (*Haematococcus pluvialis* crtW) polypeptide, operatively linked to the 3' termination sequence from *Agrobacterium* Ti-DNA that encodes nopaline synthase (nos), as well as several important restriction enzyme sites and their position numbers.

The β-carotene ketolase gene (crtw) from *Haematococcus pluvialis* [See Kajiwara et al., *Plant Mol Biol.*, 29(2): 343–352 (1995)] was prepared by polymerase chain reaction (PCR) using as template a clone of the gene obtained from Dr. Toshihiro Toguri, Kirin Brewery Co., Ltd. The specific primers that were used introduced a Kpn I restriction site at the 3' end of the gene (crtW-L28: GCCAGTGCCAAGG-TACCTCTGTCATGCC; SEQ ID NO: 1) and a Nde I site at the 5' end (crtW-U28: CCGGGGATCCTCTACATATG-CACGTCGC; SEQ ID NO: 2). After digestion with Kpn I and Nde I, the crtW gene was ligated into the plasmid pBHX533 (FIG. 2) containing the nopaline synthase polyadenylation signal. The resulting vector was designated pBHX539 (FIG. 3).

Figure 4:
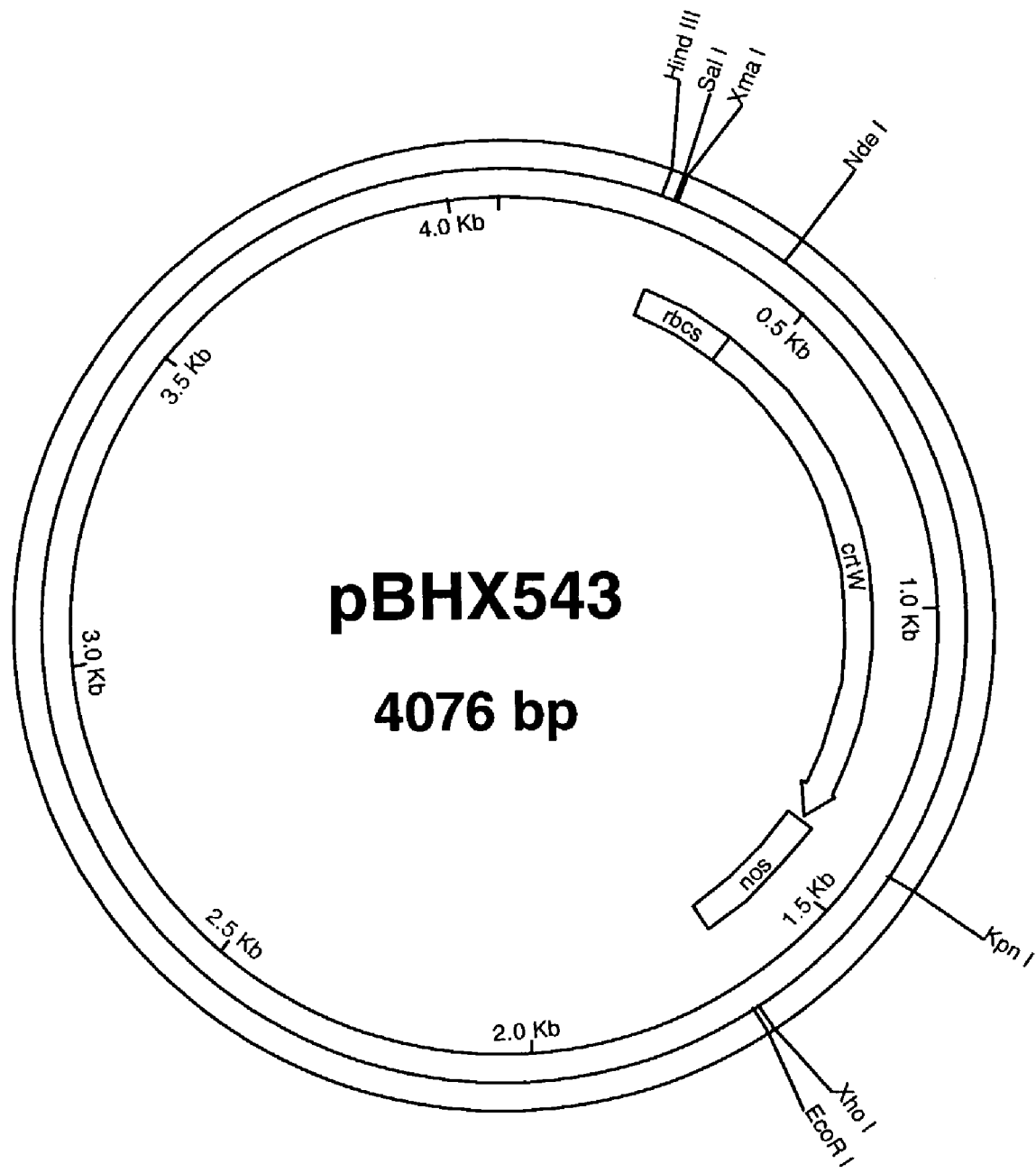
FIG. 4 schematically shows plasmid pBHX543 that contains an approximately 4076 base pair (bp) DNA segment that includes genes encoding the RUBISCO (RBCS)/ketolase (*Haematococcus pluvialis* crtW) chimeric polypeptide, as well as the 3' termination sequence from *Agrobacterium* Ti-DNA that encodes nopaline synthase (nos), and several important restriction enzyme sites and their position numbers.

The transit peptide from the *Nicotiana tabacum* ribulose bisphosphate carboxylase small subunit (RUBISCO; rbcs) [See Mazur et al., *Nucleic Acids Res.*, 13(7):2373–2386 (1985)] was prepared by PCR with primers that introduced an Xma I site at the 5' end (rbcsU30: CTCGTCGACCCGG-GATGGCTTCCTCAGTTC; SEQ ID NO: 3) and an Nde I site at the 3' end (rbcsL30: CCCATATGTTGCACTCTTC-CGCCGTTGCTG; SEQ ID NO: 4). The transit peptide sequence was ligated into pBHX539 between the Nde I and Xma I restriction sites. The resulting plasmid was designated pBHX543 (FIG. 4).

Figure 5:
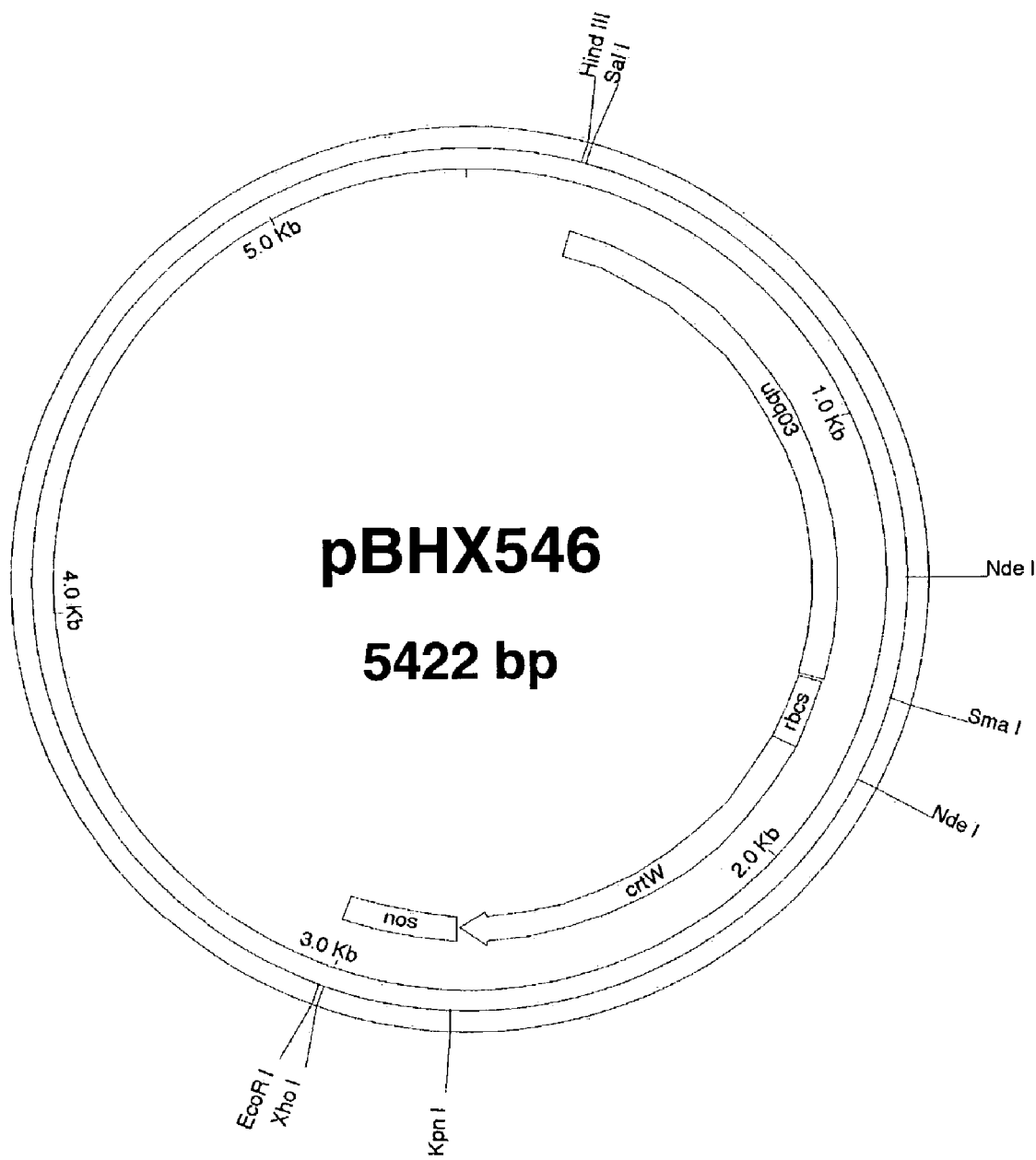
FIG. 5 schematically shows plasmid pBHX546 that contains an approximately 5422 base pair (bp) DNA segment that includes genes encoding the RUBISCO (RBCS)/ketolase (*Haematococcus pluvialis* crtW) chimeric polypeptide, as well as the ubiquitin 3 promoter (UBQ3) from *Arabidopsis* thaliana, the 3' termination sequence from *Agrobacte-*

The ubiquitin 3 (UBQ3) gene promoter from *Arabidopsis thaliana* was prepared by PCR with primers that introduced a Hind III site and a Sal I site at the 5' end (UBQ3U37: ACAAGCTTTCAGAGTCGACTTCG-GATTTGGAGCCAAG; SEQ ID 5) and an Xma I site at the 3' end (UBQ3L28: TCATCCCCGGGATGTGAAA-GAGAGAGTC; SEQ ID 6). The UBQ3 PCR product was ligated into pBHX 543 between the Hind III and Xma I restriction sites. The resulting plasmid was designated pBHX546 (FIG. 5).

Plasmid pBHX544

An approximately 2.4 kb segment containing the entire LIS1::rbcs::crtW::nos expression cassette was removed from pBHX657 (FIG. 10; see Example 2) by digestion with Hind III and EcoR I. This fragment was ligated into pUC19 between the Hind III and EcoR I sites. The resulting plasmid was designated pBHX544 (FIG. 6). This plasmid contains a complete cassette for the expression of the *Haematococcus pluvialis* crtw gene under the control of the LIS1 promoter.

B. Promoter from *A. thaliana*

Plasmid pBHX560

The upstream (promoter) region of the ubiquitin 11 (UBQ11) gene from *Arabidopsis thaliana* [See Callis et al., *Genetics*, 139(2):921–939 (1995); and Sun et al., *Plant J.*, 11(5):1017–1027 (1997)] was prepared by PCR using primers that added a Hind III site to the 5' end (UBQ11U30: CAAAGCTTCAGACTAGTCGACTTGCCTCAA; SEQ ID NO: 7) and an Xma I site at the 3' end (UBQ11L30: CAATTCGATGGGGCCCGGGATCTTGATCAC; SEQ ID NO: 8). The plasmid pBHX544 was digested with Hind III and Xma I to remove the LIS1 promoter and the UBQ11 promoter was ligated into these sites. The resulting plasmid contains a complete cassette for the expression of *Haematococcus pluvialis* crtW under the control of the UBQ11 promoter and was designated pBHX560 (FIG. 7).

C. β-Carotene Ketolase from *A. aurantiacum*

Plasmid pBHX562

The crtW gene from *Agrobacterium aurantiacum* [See Misawa et al., *Biochem. Biophys. Res. Commun.*, 209(3) :867–876 (1995); Misawa et al., *J. Bacteriol.*, 177(22): 6575–6584 (1995)] was prepared by PCR using a clone of the gene (obtained from Dr. Toshihiro Toguri, Kirin Brewery Co., Ltd.) as template. As with the *Haematococcus pluvialis* gene, the specific primers that were used introduced a Kpn I restriction site at the 3' end of the gene (Ag-crtWL24: CCAGTGCCAAGCTGGTACCGTCAT; SEQ ID NO: 9) and an Nde I site at the 5' end (Ag-crtWU26: GGGGATC-CTCTACATATGAGCGCACA; SEQ ID NO: 10). The plasmid pBHX544 was digested with Kpn I and Nde I to remove the *H. pluvialis* crtW gene and the *A. aurantiacum* gene was ligated into those sites. The resulting plasmid contains a complete cassette for the expression of the *Agrobacterium aurantiacum* crtW gene under the control of the LIS1 promoter and was designated pBHX562 (FIG. 8).

Plasmid pBHX564

In a similar procedure, the plasmid pBHX560 was digested with Kpn I and Nde I to remove the *H. pluvialis* crtw gene and the *A. aurantiacum* gene was ligated into those sites. The resulting plasmid contains a complete cassette for the expression of the *Agrobacterium aurantiacum* crtW gene under the control of the UBQ11 promoter, and was designated pBHX564 (FIG. 9).

Plasmid pBHX650

A general cloning vector for biolistic (transformation by bombardment) transformation was constructed by modifying the commercial vector pUC18.

Plasmid pBHX598 (above) was digested with Kpn I and treated with T4 DNA polymerase to create a blunt end. The plasmid was then digested with Hind III to release the DNA fragment containing the UBQ3 promoter and the nptII coding sequence. That fragment was ligated into the plasmid pUC18 that had been digested with Nde I and treated with T4 DNA polymerase to create a blunt end, followed by digestion with Hind III. The resultant plasmid was designated pBHX650 (FIG. 22).

D. Astaxanthin in Production *E. coli* pBHX611

A *Haematococcus pluvialis* β-carotene ketolase (crtW) plasmid for gene expression in *E. coli* was constructed. Plasmid pBHX543 (see Example 1) was digested with Kpn I and treated with T4 DNA polymerase to create a blunt end. The plasmid was then digested with Nde I to release the DNA fragment containing the crtW gene. That fragment was ligated into the commercial plasmid pET15b (Novagen, Madison, Wis.) that had been digested with BamH I and treated with T4 DNA polymerase to create a blunt end, followed by digestion with Nde I. The resultant plasmid was designated pBHX611.

Plasmid pBHX611 was transformed into an *E. coli* strain producing zeaxanthin [pAC-ZEAX; Lotan et al., *FEBS Letters*, 364:125–128 (1995)] and an *E. coli* strain producing β-carotene [pAC-BETA; Cunningham et al., *Plant Cell* 8:1613–1626 (1996)). HPLC analysis of the transformed PAC-BETA strain revealed 70.7% canthaxanthin, 9.9% β-carotene and additional, unidentified, putative keto-carotenoids. Analysis of the transformed pAC-ZEAX strain revealed 70.8% astaxanthin, 11.8% zeaxanthin and 3.3% β-carotene. These results are contradictory to the results reported in the above Lotan et al. article wherein a similar study was said to produce no astaxanthin and a conclusion that zeaxanthin is not a substrate for the encoded ketolase.

EXAMPLE 2

Binary Vectors

Plasmid pBHX103

A plasmid containing the 5'-flanking region of the Clarkia breweri LIS1 gene was obtained from Dr. Eran Pichersky of the University of Michigan. An about 1 kb fragment containing the LIS1 5'-flanking region was synthesized by PCR using the primers: BHX30: CCAAGCTTATCTAATAATG-TATCAAAATC (SEQ ID NO: 11) and BHX36: CAGC-CCGGGATGGTTGTCTTGTTTAAGGTGG (SEQ ID NO: 12). These primers were designed to anneal to the 5' flanking region at one end and within the 5' untranslated leader region at the 3' end. The PCR product was digested with the restriction enzymes, Hind III and Sma I, which cleave at the 5' and 3' ends of the fragment, respectively. The digested fragment was gel-purified and subsequently inserted into a Hind III- and Sma I-digested plasmid containing a multi-cloning site region (MCS) followed by the nos polyA signal-containing region to create a LIS1::MCS::nos transgene (designated plasmid pBHX103).

Plasmid pBHX107

A 1.5 kb Hinc II fragment from plasmid pATC921 (U.S. Pat. No. 5,618,988; containing the crtB gene with a rbcs transit peptide fused to the N-terminus of the crtB protein-coding region) was inserted in the sense orientation into the Sma I site located between the LIS1 promoter and the nos fragments of plasmid pBHX103 to create plasmid pBHX107.

Plasmid pBHX112

Plasmid pBHX107 was digested with Hind III and EcoR I to liberate a fragment containing the LIS1::rbcs::crtB::nos transgene. This fragment was then ligated into a T-DNA binary vector previously digested with Hind III and EcoR I to create plasmid pBHX112.

Plasmid pBHX113

A Hind III—EcoR I fragment consisting of the promoter-containing region of the *Clarkia breweri* LIS1 gene was prepared by PCR with primers that introduced a Hind III site at the 5' end (LIS1U29: CCAAGCTTATCTAATAATGTAT-CAAAATC; SEQ ID NO: 13) and a Sma I site at the 3' end (LIS1L31: CAGCCCGGGATGGTTGTCTTGTTTAAG-GTGG; SEQ ID NO: 14), as discussed before. The LIS1 PCR product fused to the GFP gene (the sm-RSGFP version contained within plasmid pCD3–327 that is available from the Arabidopsis Biological Resource Center in Columbus, Ohio) and nos polyA signal-containing region was isolated. This fragment was then ligated into a T-DNA binary commercial vector pBI101 (See Jefferson et al., *EMBO J.*, 6 (13):3901–3907 (1987)] previously digested with Hind III and EcoR I to create pBHX113.

Plasmid pBHX567

The plasmid pBHX546 was digested with restriction enzymes Sma I and EcoR I to liberate the DNA fragment containing the RUBISCO transit peptide, crtW gene and nos polyadenylation signal. Plasmid pBHX113 was digested with Sma I and EcoR I and treated with calf intestinal alkaline phosphatase (CIP), removing the GFP gene sequence and the nos polyadenylation signal. The DNA fragment from pBHX546 was inserted into the digested binary vector pBHX113 by ligation to create the plasmid pBHX567 (FIG. 10). This binary plant expression vector contains the *H. pluvialis* β-carotene ketolase (crtW) gene driven by the linalool synthase 1 (LIS1) promoter.

Plasmid pBHX522

A general binary cloning vector was constructed by modifying the commercial vector pBI101 [See Jefferson et al., *EMBO J.*, 6(13):3901–3907 (1987)]. The neomycin phosphotransferase II (nptII) selectable marker gene was prepared by PCR using primers that added a Hind III and an Mfe I site to the 5' end (nptU38: GCACAAGCTTTG-GATCGCAATTGATGATTGAACAAGAT; SEQ ID NO: 15) and a Kpn I site at the 3' end (nptL32: CCCAGGTAC-CCGCTCAGAAGAACTCGTCAAGA; SEQ ID NO: 16). This PCR product was ligated into the vector pBHX533 (FIG. 2) that had been digested with Hind III and Kpn I. The resulting plasmid was designated pBHX503 (FIG. 11). The UBQ11 promoter [See Norris et al., *Plant Mol. Biol.*, 21:895–906 (1993)] from pSAN237 was digested with Hind III and EcoR I and ligated into plasmid pBHX503 digested with Hind III and Mfe I. The resulting plasmid was designated pBHX510 (FIG. 12).

Plasmid pBHX510 was digested with EcoR I and treated with Klenow DNA polymerase plus dNTPs to create a blunt end. The plasmid was then digested with Hind III to release the DNA fragment containing the UBQ11 promoter, nptII gene and nopaline synthase polyadenylation signal (nos). That fragment was ligated into the plasmid pBI101 (above) that had been digested with EcoR I and Pme I to remove the antibiotic resistance cassette. The resultant plasmid was designated pBHX522 (FIG. 13).

The vector pBHX522 was digested with Hind III and EcoR I to remove the β-glucuronidase (GUS) coding region and nopaline synthase polyadenylation signal. The crtW expression cassettes from each of the non-binary vectors described above were removed by digestion with Hind III and EcoR I, and ligated into the digested plasmid pBHX522.

The binary version of plasmid pBHX544 (LIS1/*H. pluvialis* crtw) was designated plasmid pBHX561 (FIG. 14). The binary version of plasmid pBHX560 (UBQ11/*H. pluvialis* crtW) was designated plasmid pBHX565 (FIG. 15). The binary version of plasmid pBHX562 (LIS1/*A. aurantiacum* crtw) was designated plasmid pBHX563 (FIG. 16). The binary version of plasmid pBHX564 ( UBQ11/*A. aurantiacum* crtW) was designated plasmid pBHX566 (FIG. 17). A second LIS1/*H. pluvialis* crtW binary vector was constructed in a manor identical to pBHX567 and was designated as pBHX586 (FIG. 18).

Plasmid pBHX689

The binary vector pBI101 containing the carotenoid expression cassette LIS1::rbcs::crtI::nos was digested with Hind III and EcoR I to isolate the expression cassette. The vector pUC19 was digested with Hind III and EcoR I and was ligated with the carotenoid expression cassette. The resulting plasmid was designated plasmid pBHX612 (FIG. 26). Plasmid pBHX612 was digested with Sma I and Kpn I to remove the crtI coding sequence. The vector pUC19 containing the partial carotenoid cassette rbcs::crtB::nos was digested with Sma I and Kpn I to isolate the crtB coding sequence which was then ligated into the digested plasmid pBHX612. The resulting plasmid was designated plasmid pBHX663.

The binary vector pBI101 containing the carotenoid expression cassette UBQ3::rbcs::crtI::nos was digested with Sal I and EcoR I to isolate the expression cassette. The plasmid pBHX663 was linearized by digestion with Xho I and EcoR I, followed by ligation with the isolated crtI expression cassette. The resulting vector was designated pBHX671.

The dual carotenoid cassette was isolated from vector pBHX671 by digestion with Hind III and EcoR I and then ligated into the general plant transformation vector pBHX650 digested with the same two enzymes. The resulting plasmid was designated plasmid pBHX689 (FIG. 19).

Plasmid pBHX607

A general binary cloning vector was constructed by modifying the commercial vector pBI101 [See Jefferson et al., *EMBO J.*, 6(13):3901–3907 (1987)]. The neomycin phosphotransferase II (nptII) selectable marker gene was prepared by PCR using primers that added a Hind III and an Mfe I site to the 5' end (nptU38: GCACAAGCTTTG-GATCGCAATTGATGATTGAACAAGAT; SEQ ID NO: 15) and a Kpn I site at the 3' end (nptL32: CCCAGGTAC-CCGCTCAGAAGAACTCGTCAAGA; SEQ ID NO: 16). This PCR product was ligated into the vector pBHX533 (FIG. 2) that had been digested with Hind III and Kpn I. The resulting plasmid was designated pBHX520. The UBQ3 promoter [See Norris et al., *Plant Mol. Biol.*, 21:895–906 (1993)] from pSAN155 was digested with Hind III and EcoR I and ligated into plasmid pBHX520 digested with Hind III and Mfe I. The resulting plasmid was designated pBHX598.

Plasmid pBHX598 was digested with Kpn I and treated with T4 DNA polymerase to create a blunt end. The plasmid was then digested with Hind III to release the DNA fragment containing the UBQ3 promoter, and the nptII coding sequence. That fragment was ligated into the plasmid pBI101 (above) that had been digested with EcoR I and Pme I to remove the antibiotic resistance cassette. The resultant plasmid was designated pBHX607 (FIG. 23).

Plasmid pBHX658

A general binary cloning vector was constructed by modifying the commercial vector pBI101 [See Jefferson et al., *EMBO J.*, 6 (13) :3901–3907 (1987)]. The neomycin phosphotransferase II (nptII) selectable marker gene was prepared by PCR using primers that added a Hind III and an Mfe I site to the 5' end (nptU38: GCACAAGCTTTG-GATCGCAATTGATGATTGAACAAGAT; SEQ ID NO: 15) and a Kpn I site at the 3' end (nptL32: CCCAGGTAC-CCGCTCAGAAGAACTCGTCAAGA; SEQ ID NO: 16). This PCR product was ligated into the vector pBHX533 (FIG. 2) that had been digested with Hind III and Kpn I. The resulting plasmid was designated pBHX520 (FIG. XX). The UBQ3 promoter [See Norris et al., *Plant Mol. Biol.*, 21:895–906 (1993)] from pSAN155 was digested with Hind III and EcoR I and ligated into plasmid pBHX520 digested with Hind III and Mfe I. The resulting plasmid was designated pBHX598.

Plasmid pBHX598 was digested with Kpn I and treated with T4 DNA polymerase to create a blunt end. The plasmid was then digested with Hind III to release the DNA fragment containing the UBQ3 promoter and the nptII coding sequence. That fragment was ligated into the plasmid pBI101 (above) that had been digested with Dra III and treated with T4 DNA polymerase to create a blunt end, followed by digestion with Hind III to remove the antibiotic resistance cassette. The resultant plasmid was designated pBHX654.

The multi-cloning site from pUC19 was prepared by PCR using primers that added a Pme III site (pUC19mcsL24 CACGTTTAAACTACCGCACAGATG; SEQ ID NO: 17) and retained the Hind III site (pUC19mcsU20 GGCCG-CATACAGGCTGTCAG; SEQ ID NO: 18). This PCR product was ligated into the vector pBHX654 that had been digested with Hind III and Pme I to remove the existing npt II selectable marker. The resulting plasmid was designated pBHX658 (FIG. 24).

Plasmid pBHX691

The binary vector pBI101 containing the carotenoid expression cassette LIS1::rbcs::crtI: :nos was digested with Sma I and Kpn I to remove the crtI coding sequence. The vector pUC19 containing the partial carotenoid cassette rbcs::crtW::nos was digested with Sma I and Kpn I to isolate the crtW coding sequence, which was then ligated into the digested plasmid pBI101 vector. The resulting plasmid was designated plasmid pBHX586. The carotenoid expression cassette was removed from plasmid pBHX586 by digestion with Hind III and EcoR I and then ligated into the binary vector pBHX607 that had also been digested with Hind III and EcoR I. The resulting vector was designated pBHX665.

The *E. uredovora* crtZ gene was prepared by PCR using primers that added an Nde I site to the 5' end (crtZU30 CGGGGATCCTCTACATATGACCAATTTCCT; SEQ ID NO: 19) and a Kpn I site at the 3' end (crtZL30 CGACG- GCCGGTACCAAGCTAGATCTGTCAC; SEQ ID NO: 20). The PCR product was digested with, Nde I and Kpn I, and ligated into the pUC19 vector containing the carotenoid cassette UBQ3::rbcs::crtI::nos that had been digested with the same enzymes to remove the crtI gene. The resulting vector was designated plasmid pBHX667.

The vector pBHX667 was linearized by digestion with Hind III and Sal I. The carotenoid expression cassette was removed from plasmid pBHX665 by digestion with Hind III and Xho I, and then ligated into plasmid pBHX667 to form a dual carotenoid expression cassette. The resulting dual carotenoid expression vector was designated plasmid pBHX683.

The dual carotenoid expression cassette from plasmid pBHX683 was removed by digestion with Hind III and EcoR I, and ligated into the plant expression vector pBHX650 digested with the same two enzymes. The resulting plasmid was designated plasmid pBHX691 (FIG. 20).

Plasmid pBHX701

The *Adonis aestivalis* ketolase genes were prepared by PCR of *A. aestivalis* genomic DNA using primers that added an Nde I site to the 5' end (ketoU28 GAAACCTCATATG-GCAGCAGCAATTTCA; SEQ ID NO: 21) and a Kpn I site at the 3' end (ketoL32 CACGGTACCTTCAGGTAGATG-GTTGCGTTCGT; SEQ ID NO: 22XX). The undigested PCR product was ligated into the commercial vector PGEM-T Easy™. Screening identified two clones containing the Adonis ketolase 1, AdK1, coding sequence (plasmid pBHX604) and the Adonis ketolase 2 coding sequence, AdK6 (plasmid pBHX603)

The plasmid pBHX612 was digested with Not I and Hind III and ligated to an annealed pair of oligonucleotides (LisAd 1 GGCCGCAAGCTTGAGGAGGTCGAC; SEQ ID NO: 23, and LisAd 2 AGCTGTCGACCTCCT-CAAGCTTGC; SEQ ID NO: 24). This restored the Not I and Hind III sites and added a Sal I site downstream from the Hind III site. The resulting vector was designated plasmid pBHX669.

Plasmid pBHX603 was digested with EcoR I and treated with Klenow DNA polymerase to create blunt ends. The plasmid was then digested with Kpn I and ligated into vector pBHX669 digested with Sma I and Kpn I. The resulting plasmid, containing the Adonis ketolase 2 gene, AdK6, driven by the LIS1 promoter and terminated with the nopaline synthase polyadenylation sequence, was designated pBHX685.

Plasmid pBHX685 was digested with Hind III and EcoR I to isolate the ketolase expression cassette that was ligated into the binary expression vector pBHX607 that had been digested with the same two enzymes. The resulting expression plasmid was designated plasmid pBHX701 (FIG. 21).

Plasmid pBHX749

Plasmid pBHX604 was digested with EcoR I and treated with Klenow DNA polymerase to create blunt ends. The plasmid was then partially digested with Kpn I and ligated into plasmid pBHX669 digested with Sma I and Kpn I. The resulting plasmid, containing the Adonis ketolase 1, AdK1, gene driven by the LIS1 promoter and terminated with the nopaline synthase polyadenylation sequence, was designated plasmid pBHX687.

Plasmid pBHX685 (above) was digested with Hind III and EcoR I to isolate the ketolase expression cassette that was then ligated into the biolistic expression vector pBHX650 that had been digested with the same two enzymes. The resulting ketolase 2 expression plasmid was designated plasmid pBHX743.

The vector pBHX743 was linearized by digestion with EcoR I and Xho I. The ketolase 1 expression cassette was removed from plasmid pBHX687 (above) by digestion with EcoR I and Sal I, and then ligated into vector pBHX743. The resulting dual ketolase expression vector was designated pBHX747.

Plasmid pBHX747 was digested with Hind III and EcoR I to isolate the dual ketolase expression cassette that was then ligated into the binary expression vector pBHX658 that had been digested with the same two enzymes. The resulting expression plasmid was designated pBHX749 (FIG. 25).

EXAMPLE 3

EMS Treatment of *Tagetes erecta* 'Scarletade'

Seeds of *Tagetes erecta* xanthophyll marigold denominated 'Scarletade' (commercially available from PanAmerican Seed Co. 622 Town Road, West Chicago, Ill. 60185) were treated with ethyl methanesulfonate (EMS, commercially available from Sigma Chemical Co., St. Louis, Mo. 63178). Approximately 2,500 seeds were added to 400 ml of 0.4% (v/v) or 0.8% (v/v) EMS and were stirred gently for eight hours at ambient temperature. During a four-hour period following the EMS treatment, the seeds were washed sixteen times, each wash using continuous stirring with 400 ml distilled water. The treated seeds, identified as $M_1$ seeds, were then sown in trays containing soilless potting mix.

After several weeks, the seedlings were transplanted into pots(containing soilless potting mix and maintained in the greenhouse. Flowers produced by those plants were naturally self-pollinated. The resulting seeds, identified as $M_2$ seeds, were harvested from approximately 2,300 plants. Of these 2,300 plants, approximately 1,500 were grown from seeds treated with 0.4% EMS and approximately 800 were grown from seeds treated with 0.8% EMS. To facilitate identification of mutant plants, the $M_2$ seeds from each of 50 $M_1$ plants were combined into one lot, resulting in a total of 47 seed lots. During the summer of the year 2000, 500 seeds from each of the 47 lots were sown and the resulting plants were field-grown at PanAmerican Seed Co. in Santa Paula, Calif. 93060.

EXAMPLE 4

HPLC Screening of EMS-treated *Tagetes erecta* 'Scarletade'

EMS-treated 'Scarletade' plants were field-grown at PanAmerican Seed Co. in Santa Paula, Calif. 93060, and were screened by HPLC for altered zeaxanthin ratio. Flowers approximately 98% fully opened were selected for analysis. From each flower, one petal was removed one-third of the distance from the flower center and placed in a 3.5"×0.75" glass vial containing approximately 5 grams of glass beads. Vials were packaged with dry ice until stored at −80° C.

For analysis, solvent delivery and aliquot removal were accomplished with a robotic system comprising a single injector valve Gilson 232XL and a 402 2S1V diluter [Gilson, Inc. USA, 3000 W. Beltline Highway, Middleton, Wis.]. For saponification, 3 ml of 50% potassium hydroxide hydroethanolic solution (4 water:1 ethanol) was added to each vial, followed by the addition of 3 ml of octanol. The saponification treatment was conducted at room temperature with vials maintained on an IKA HS 501 horizontal shaker [Labworld-online, Inc., Wilmington, N.C.] for fifteen hours at 250 movements/minute, followed by a stationary phase of approximately one hour.

Following saponification, the supernatant was diluted with 0.9 ml of methanol. The addition of methanol was conducted under pressure to ensure sample homogeneity. Using a 0.25 ml syringe, a 0.1 ml aliquot was removed and transferred to HPLC vials for analysis.

For HPLC analysis, a Hewlett Packard 1100 HPLC, complete with a quaternary pump, vacuum degassing system, six-way injection valve, temperature regulated autosampler, column oven and Photodiode Array detector was used [Agilent Technologies available through Ultra Scientific Inc., 250 Smith Street, North Kingstown, R.I.]. The column was a Waters YMC30, 5-micron, 4.6×250 mm with a guard column of the same material [Waters, 34 Maple Street, Milford, Mass.]. The solvents for the mobile phase were 81 methanol: 4 water: 15 tetrahydrofuran (THF) stabilized with 0.2% BHT (2,6-di-tert-butyl-4-methylphenol). Injections were 20 µl. Separation was isocratic at 30° C. with a flow rate of 1.7 ml/minute. The peak responses were measured by absorbance at 447 nm.

Using this protocol, the results from the first 2,546 samples were statistically analyzed to establish average values for lutein and zeaxanthin content. Because this was a semi-quantitative analytical screen, peak area values were used. To identify a mutant having a higher than average lutein and/or zeaxanthin concentration, a value of three standard deviations greater than the average was calculated. The calculated peak area means, standard deviations and zeaxanthin ratios are shown in Table 1, below.

TABLE 1

Lutein and Zeaxanthin Confidence Interval Calculations

| Statistic | Peak Area Lutein | Peak Area Zeaxanthin | Ratio (%) |
|---|---|---|---|
| Mean | 775.0 | 41.6 | 5.03 |
| Standard deviation (sd) | 263.2 | 16.4 | 0.71 |
| Mean + 3 sd | 1564.6 | 90.9 | 7.16 |

Based on the above values, samples were selected having lutein peak areas greater than 1565 and/or zeaxanthin peak areas greater than 91. Samples were also selected only for high lutein peak area, and for zeaxanthin ratios greater than 10 percent. A total of 88 mutants were identified from 21,754 assayed samples using these selection parameters. The total number of mutants resulting from each EMS seed treatment is shown in Table 2, below.

TABLE 2

Correlation of 'Scarletade' Mutants to EMS Treatment

| Selection Parameter | 0.4% EMS Treatment | 0.8% EMS Treatment | Total Plants |
|---|---|---|---|
| Zeaxanthin Ratio > 10% | 10 | 13 | 23 |
| Lutein > 1566 and Zeaxanthin > 91 | 18 | 10 | 28 |
| Lutein > 1566 and Zeaxanthin < 91 | 20 | 7 | 27 |
| Lutein < 1566 and Zeaxanthin > 91 | 7 | 3 | 10 |

More specific results of those assays as to relative levels of lutein and zeaxanthin are shown in Table 3, below.

TABLE 3

Identified 'Scarletade' Mutants

| Plant Identifier | Lutein Area | Zeaxanthin Area | Percent Zeaxanthin | Percent EMS Used |
|---|---|---|---|---|
| 124-257 | 2.115 | 55.635 | 96.34 | 0.4 |
| 119-494 | 9.254 | 131.036 | 93.40 | 0.8 |
| 112-263 | 8.095 | 35.273 | 81.33 | 0.4 |
| 118-036 | 11.441 | 31.691 | 73.47 | 0.8 |
| 088-452 | 2.94 | 6.689 | 69.47 | 0.4 |
| 118-035 | 11.289 | 23.951 | 67.97 | 0.8 |
| 114-334 | 58.24 | 97.968 | 62.72 | 0.4 |
| 117-185 | 39.002 | 44.027 | 53.03 | 0.8 |
| 108-108 | 13.424 | 10.155 | 43.07 | 0.4 |
| 088-425 | 8.959 | 4.394 | 32.91 | 0.4 |
| 094-238 | 7.285 | 3.063 | 29.60 | 0.4 |
| 110-308 | 46.753 | 14.248 | 23.36 | 0.4 |
| 132-346 | 31.036 | 8.856 | 22.20 | 0.8 |
| 100-334 | 282.987 | 54.298 | 16.10 | 0.8 |
| 101-331 | 246.402 | 46.467 | 15.87 | 0.8 |
| 100-198 | 119.381 | 21.449 | 15.23 | 0.8 |
| 101-190 | 139.027 | 23.125 | 14.26 | 0.8 |
| 114-315 | 351.524 | 56.898 | 13.93 | 0.4 |
| 100-470 | 189.703 | 27.743 | 12.76 | 0.8 |
| 117-348 | 369.903 | 43.315 | 10.48 | 0.8 |
| 132-266 | 374.096 | 43.8 | 10.48 | 0.8 |
| 123-310 | 60.743 | 6.818 | 10.09 | 0.4 |
| 116-106 | 453.538 | 50.287 | 9.98 | 0.8 |

About 21,700 plants exhibited typical zeaxanthin ratios of about 4 to about 7 percent (about 1:25 to about 1:15). The above data illustrate the relative rarity of the mutations contemplated, as well as the almost equal number of plants that exhibit reduced zeaxanthin levels. The data also do not show a preference for the use of one level of mutagen versus the other used here.

EXAMPLE 5

EMS Treatment of *Tagetes erecta* 13819

Seeds of *Tagetes erecta* xanthophyll marigold named 13819(a breeding selection of PanAmerican Seed Co. 622 Town Road, West Chicago, Ill. 60185) were treated with ethyl methanesulfonate (EMS, commercially available from Sigma Chemical Co. St. Louis, Mo. 63178). Approximately, 7,000 seeds were added to 600 ml of 0.2% (v/v) or 0.4% (v/v) EMS and stirred gently for eight hours at ambient temperature. During a four-hour period following the EMS treatment, the seeds were washed sixteen times, each wash using continuous stirring with 600 ml distilled water.

The treated seeds, identified as $M_1$ seeds, were then sown in trays containing soilless potting mix. After three to four weeks, the seedlings were transplanted into the field. Flowers produced by these plants were bagged to prevent cross-pollination, and were permitted to spontaneously self-pollinate. The resulting seeds, identified as $M_2$ seeds, were harvested from approximately 2,391 plants. Of these plants, approximately 951 were grown from seeds treated with 0.2% EMS and approximately 1,440 were grown from seeds treated with 0.4% EMS.

To facilitate identification of mutant plants, the $M_2$ seeds from each of 50 plants were combined into one lot. This grouping resulted in a total of 48 seed lots. From late October through mid-November of the year 2000, 1000 seeds from each of 15 lots of the 0.4% EMS treatment were sown and 700 plants of each lot were greenhouse-grown at Seaview Nursery in El Rio, Calif. 93060. In addition, 1,500 seeds from all of the 48 lots were sown in late October of the year 2000, and 765 plants from each of the lots were field-grown at Semillas Pan American Chile LTDA, in Pichidegua, Chile.

EXAMPLE 6

HPLC Screening of EMS-treated *Tagetes erecta* 13819

EMS-treated 13819 $M_2$ plants were greenhouse-grown at Seaview Nursery in El Rio, Calif. 93060 and field-grown at Semillas PanAmerican Chile LTDA, in Pichidegua, Chile, and were screened for altered zeaxanthin ratio. Flowers approximately 98% fully opened were selected for analysis. From these flowers, petals were removed one-third of the distance from the flower center. Approximately 100 mg of petal tissue was placed in plastic bags and stored frozen until analysis. Dry weight was determined for two petals that were placed in 3.5"×0.75" glass vials containing approximately 5 grams of glass beads.

For analysis, solvent delivery and aliquot removal were accomplished with a robotic system comprising a single injector valve Gilson 232XL and a 402 2S1V diluter. For saponification, 3 ml of 50% potassium hydroxide hydroethanolic solution (4 water: 1 ethanol) was added to each vial, followed by the addition of 3 ml octanol. The saponification treatment was conducted at room temperature with vials maintained on an IKA HS 501 horizontal shaker for fifteen hours at 250 movements per minute followed by a stationary phase of approximately one hour.

Following saponification, the supernatant was diluted with 0.9 ml of methanol. The addition of methanol was conducted under pressure to ensure sample homogeneity. Using a 0.25 ml syringe, a 0.1 ml aliquot was removed and transferred to HPLC vials for analysis.

For HPLC analysis, a Hewlett Packard 1100 complete with a quaternary pump, vacuum degassing system, six-way injection valve, temperature regulated autosampler, column oven and Photodiode Array detector was used. The column was a Waters YMC30, 5-micron, 4.6×250 mm with a guard column of the same material. Standards were obtained from DHI-Water & Environment, DK-2970 Horsholm, Denmark and Sigma Chemical Co., St. Louis, Mo. 63178. The solvents for the mobile phase were 81 methanol: 4 water: 15 tetrahydrofuran stabilized with 0.2% BHT. Injections were 20 µl. Separation was isocratic at 30° C. with a flow rate of 1.7 ml/minute. The peak responses were measured at 447 nm.

Using this protocol, the results from the first 507 samples were statistically analyzed to establish average values for lutein and zeaxanthin content. To identify a mutant having a higher or lower than average lutein and zeaxanthin concentration, a value of three standard deviations greater than or less than the average was calculated. The calculated means, standard deviations and zeaxanthin ratios are shown in Table 4, below.

TABLE 4

| | Lutein and Zeaxanthin Confidence Interval Calculations | | | |
|---|---|---|---|---|
| Statistic | Lutein mg/g Fresh Weight | Zeaxanthin mg/g Fresh Weight | Lutein + Zeaxanthin mg/g Fresh Weight | Ratio (%) |
| Mean | 0.64 | 0.04 | 0.68 | 5.98 |
| Standard deviation | 0.14 | 0.01 | 0.147 | 1.1 |

TABLE 4-continued

| | Lutein and Zeaxanthin Confidence Interval Calculations | | | |
|---|---|---|---|---|
| Statistic | Lutein mg/g Fresh Weight | Zeaxanthin mg/g Fresh Weight | Lutein + Zeaxanthin mg/g Fresh Weight | Ratio (%) |
| Mean + 3 sd | 1.06 | 0.07 | 1.12 | 9.28 |
| Mean − 3 sd | 0.22 | 0.007 | 0.24 | 2.68 |

Based on the above values, samples were selected having zeaxanthin ratios greater than 10 percent, combined lutein and zeaxanthin content greater than 1.12 mg/g fresh weight and combined lutein and zeaxanthin content less than 0.24 mg/g fresh weight. A total of 347 mutants were identified having a sum of lutein plus zeaxanthin greater than 1.12 mg/g, and 43 mutants having a zeaxanthin ratio greater than 10 percent were identified from 8192 samples using these selection parameters. The total number of mutants resulting from each EMS seed treatment is shown in Table 5, below.

TABLE 5

| Correlation of 13819 Mutants to EMS Treatment | | | |
|---|---|---|---|
| Selection Parameter | 0.2% EMS Treatment | 0.4% EMS Treatment | Total Plants |
| Zeaxanthin Ratio > 10% | 2 | 41 | 43 |
| Lutein + Zeaxanthin > 1.12 mg/g dry weight | 6 | 341 | 347 |
| Lutein + Zeaxanthin < 0.24 mg/g dry weight | 2 | 175 | 177 |

Of the mutants having a zeaxanthin ratio greater than about 10 percent zeaxanthin, about 47 percent had between 10 and under 13 percent, whereas 53 percent exhibited 13 percent or greater.

EXAMPLE 7

Carotenoid Composition in Petals of Select Marigolds

Carotenoid compositions were determined for 'Scarletade' wild-type and mutant samples selected from those identified in the screening procedure described in Example 4. Petal samples were stored in a −80° C. freezer until mutants were identified. Samples were lyophilized, and the dried tissue was stored under argon at −80° C. until ready for analysis.

Extraction procedures were performed under red light. Dried petals were ground to pass through a No. 40 sieve mesh size. A ground sample was accurately weighed and transferred into a 100 ml red volumetric flask. To the sample, 500 microliters (µl) of $H_2O$ were added, and the mixture was swirled for 1 minute. Thirty ml of extractant solvent (10 ml hexane+7 ml acetone+6 ml absolute alcohol+7 ml toluene) were added, and the flask was shaken at 160 rpm for 10 minutes.

For saponification, 2 ml of 40% methanolic KOH were added into the flask, which was then swirled for one minute. The flask was placed in a 56° C. $H_2O$ bath for 20 minutes. An air condenser was attached to prevent loss of solvent.

The sample was cooled in the dark for one hour with the condenser attached. After cooling, 30 ml of hexane were added, and the flask was shaken at 160 rpm for 10 minutes.

The shaken sample was diluted to volume (100 ml) with 10% sodium sulfate solution and shaken vigorously for one minute. The sample remained in the dark for at least 30 minutes. A 35 ml aliquot was removed from the approximately 50 ml upper phase, and transferred to a sample cup. An additional 30 ml of hexane were added into the flask that was then shaken at 160 rpm for 10 minutes. After approximately one hour, the upper phases were combined. For HPLC analysis, 10 ml aliquots were dried under nitrogen and stored under argon at −80° C.

HPLC equipment comprised an Alliance 2690 equipped with a refrigerated autosampler, column heater and a Waters Photodiode Array 996 detector (Waters Corp., 34 Maple Street Milford, Mass. 01757). Separation was obtained with a YMC30 column, 3 μm, 2.0×150 mm with a guard column of the same material. Standards were obtained from ICC Indofine Chemicals Somerville, N.J. 088876 and from DHI-Water & Environment, DK −2970 Horsholm, Denmark.

The dried mutant samples were resuspended in tetrahydrofuran and methanol to a total volume of 200 μl and filtered, whereas the control was not additionally concentrated. Carotenoids were separated using a gradient method. Initial gradient conditions were 90% methanol: 5% water: 5% methyl tert-butyl ether at a flow rate of 0.4 milliliters per minute (ml/min). From zero to 15 minutes, the mobile phase was changed from the initial conditions to 80 methanol: 5 water: 15 methyl tert-butyl ether, and from 15 to 60 minutes to 20 methanol: 5 water: 75 methyl tert-butyl ether. For the following 10 minutes, the mobile phase was returned to the initial conditions and the column equilibrated for an additional 10 minutes. The column temperature was maintained at 27° C. and the flow rate was 0.4 ml/minute. Injections were 10 μl. The majority of peak responses were measured at 450 nm and additional areas added from 286, 348, 400 and 472 nm extracted channels.

Values for carotenoid profiles of selected mutants are indicated in Tables 6a, 6b and 6c, below, using peak area as percent of the total area. Indicated compound identifications are based on spectra extracted and maximal absorbance in ethanol (lambda maxima; ETOH) obtained for major peaks in each chromatogram, some of which were verified by retention times of known standards. Values combine suspected isomers of the same compounds. Some compounds may contain minor impurities. Included in the Table are values for yellow colored American marigolds (yellow marigold) noted in Quackenbush et al., *J. Assoc. Off. Anal. Chem.*, 55 (3):617–621 (1972). Single entries are used in Tables 6a–6c for neoxanthin/violaxanthin and chrysanthemaxanthin/flavoxanthin compound pairs that could not be separated by the procedure used here.

TABLE 6a

Relative Percent Distribution of Carotenoids In Petals of *Tagetes erecta* and Mutants

| Carotenoid | Wavelength in EtOH (nm) | Marigold Selections | | | | | | | | | |
|---|---|---|---|---|---|---|---|---|---|---|---|
| | | Yellow Marigold | 'Scarletade' | 13819 | 117-185 | 124-257 | 119-494 | 112-263 | 118-035 | 088-425 | 325-444 |
| Phytoene | 276, 286, 297 | 2.4 | 0.3 | 0.3 | 6.8 | 7.0 | 1.0 | 11.0 | 12.3 | 34.3 | 30.9 |
| Phytofluene (isomers) | 331, 348, 367 | 2.6 | 0.5 | 0.4 | 4.0 | 4.2 | 0.9 | 7.5 | 7.4 | 17.8 | 13.3 |
| ζ-Carotene (cis/trans isomers) | 377, 399, 425 | nf* | <0.1 | <0.1 | 5.6 | 5.3 | 1.3 | 6.9 | 6.8 | 18.2 | 17.1 |
| Neurosporene | 416, 440, 470 | nr** | <0.1 | <0.1 | 0.1 | 0.2 | <0.1 | <0.1 | <0.1 | 3.5 | 3.5 |
| Lycopene | 447, 472, 504 | nr | <0.1 | <0.1 | 0.5 | 1.3 | <0.1 | <0.1 | <0.1 | 1.0 | 2.8 |
| α-Carotene | 423, 444, 473 | 0.1 | <0.1 | <0.1 | <0.1 | <0.1 | <0.1 | <0.1 | <0.1 | 0.8 | 1.2 |
| β-Carotene | 425, 451, 478 | 0.5 | <0.1 | <0.1 | 4.4 | 6.8 | 2.3 | 0.6 | 0.3 | 2.3 | 4.8 |
| Neoxanthin | 415, 439, 467 | 0.8 | 1.5 | 4.1 | 13.3 | 12.8 | 16.7 | 4.3 | 3.5 | 0.7 | 1.1 |
| Violaxanthin | 419, 440, 470 | nr | | | | | | | | | |
| Antheraxanthin | 422, 444, 472 | 0.1 | 3.1 | 5.5 | 12.5 | 14.4 | 19.2 | 4.1 | 4.5 | 0.9 | 1.5 |
| Lutein | 420, 445, 475 | 72.3 | 84.9 | 81.7 | 13.3 | 1.3 | <0.1 | 0.6 | 7.1 | 2.0 | 4.9 |
| Zeaxanthin | 428, 450, 478 | 16.4 | 4.7 | 5.9 | 21.3 | 30.6 | 35.7 | 16.5 | 18.2 | 2.0 | 4.0 |
| α-Cryptoxanthin | 421, 446, 475 | 0.8 | <0.1 | <0.1 | <0.1 | <0.1 | <0.1 | 32.2 | 26.9 | <0.1 | 0.2 |
| β-Cryptoxanthin | 428, 450, 478 | 0.5 | <0.1 | <0.1 | 0.5 | 0.6 | 0.8 | 0.2 | 0.4 | 1.9 | 1.8 |
| β-Zeacarotene | 406, 428, 454 | 0.5 | | | | not identified | | | | | |
| Chrysanthemaxanthin | 400, 421, 448 | 0.8 | <0.1 | <0.1 | 2.3 | 1.5 | 4.5 | 0.8 | 0.5 | 0.2 | 0.2 |
| Flavoxanthin | 400, 421, 448 | 1.3 | | | | | | | | | |

TABLE 6a-continued

Relative Percent Distribution of Carotenoids
In Petals of *Tagetes erecta* and Mutants

| Carotenoid | Wave-length in EtOH (nm) | Marigold Selections | | | | | | | | | |
|---|---|---|---|---|---|---|---|---|---|---|---|
| | | Yellow Marigold | 'Scarletade' | 13819 | 117-185 | 124-257 | 119-494 | 112-263 | 118-035 | 088-425 | 325-444 |
| Auroxanthin | 380, 401, 426 | 0.1 | not identified | | | | | | | | |
| Other compounds that show absorbance at 450 nm | | 0.8 | 5.0 | 2.1 | 15.3 | 14.0 | 17.6 | 15.1 | 12.0 | 14.3 | 12.7 |

*nf = not found
**nr = not reported

TABLE 6b

Relative Percent Distribution of Carotenoids In
Petals of *Tagetes erecta* and Mutants

| Carotenoid | Wave-length in EtOH (nm) | Marigold Selections | | | | | | | |
|---|---|---|---|---|---|---|---|---|---|
| | | Yellow Marigold | 'Scarletade' | 13819 | 100-198 | 100-334 | 100-470 | 101-190 | 114-315 |
| Phytoene (isomers) | 276, 286, 297 | 2.4 | 0.3 | 0.3 | 4.8 | 3.9 | 6.1 | 3.4 | 5.2 |
| Phytofluene (isomers) | 331, 348, 367 | 2.6 | 0.5 | 0.4 | 3.2 | 3.2 | 3.8 | 3.2 | 3.3 |
| ζ-Carotene (cis/trans isomers) | 377, 399, 425 | nf* | <0.1 | <0.1 | 4.8 | 4.0 | 4.4 | 3.6 | 3.2 |
| Neurosporene | 416, 440, 470 | nr** | <0.1 | <0.1 | <0.1 | <0.1 | <0.1 | <0.1 | <0.1 |
| Lycopene | 447, 472, 504 | nr | <0.1 | <0.1 | <0.1 | <0.1 | <0.1 | <0.1 | <0.1 |
| α-Carotene | 423, 444, 473 | 0.1 | <0.1 | <0.1 | 0.3 | 0.4 | 0.2 | 0.4 | 0.2 |
| β-Carotene | 425, 451, 478 | 0.5 | <0.1 | <0.1 | 0.8 | 0.7 | 0.5 | 0.8 | 0.5 |
| Neoxanthin | 415, 439, 467 | 0.8 | 1.5 | 4.1 | <0.2 | 0.3 | <0.2 | <0.2 | <0.2 |
| Violaxanthin | 419, 440, 470 | nr | | | | | | | |
| Anthera-xanthin | 422, 444, 472 | 0.1 | 3.1 | 5.5 | <0.2 | <0.2 | <0.2 | <0.2 | <0.2 |
| Lutein | 420, 445, 475 | 72.3 | 84.9 | 81.7 | 68.0 | 70.7 | 67.5 | 71.1 | 71.6 |
| Zeaxanthin | 428, 450, 478 | 16.4 | 4.7 | 5.9 | 14.8 | 13.4 | 13.1 | 13.6 | 12.3 |
| α-Crypto-xanthin | 421, 446, 475 | 0.8 | <0.1 | <0.1 | 0.6 | 0.6 | 0.5 | 0.6 | 0.4 |
| δ-Carotene | 431, 456, 489 | nr | <0.1 | <0.1 | 0.5 | 0.2 | 0.8 | 0.4 | 0.5 |
| β-Crypto-xanthin | 428, 450, 478 | 0.5 | <0.1 | <0.1 | <0.2 | <0.2 | <0.2 | <0.2 | <0.2 |
| β-Zeacarotene | 406, 428, 454 | 0.5 | not identified | | | | | | |
| Chrysanthema-xanthin | 400, 421, 448 | 0.8 | <0.1 | <0.1 | <0.2 | <0.2 | <0.2 | <0.2 | <0.2 |
| Flavoxanthin | 400, 421, 448 | 1.3 | | | | | | | |
| Auroxanthin | 380, 401, 426 | 0.1 | not identified | | | | | | |
| Other compounds that show absorbance at 450 nm | | 0.8 | 5.0 | 2.1 | 2.1 | 2.6 | 2.9 | 2.8 | 2.7 |

*nf = not found
**nr = not reported

TABLE 6c

Relative Percent Distribution of Carotenoids In Petals of *Tagetes erecta* and Mutants

| Carotenoid | Wavelength in EtOH (nm) | Marigold Selections | | | | | | |
|---|---|---|---|---|---|---|---|---|
| | | Yellow Marigold | 'Scarletade' | 13819 | 126-415 | 098-240 | 098-394 | 115-004 |
| Phytoene (isomers) | 276, 286, 297 | 2.4 | 0.3 | 0.3 | 11.8 | 10.0 | 8.6 | 13.0 |
| Phytofluene (isomers) | 331, 348, 367 | 2.6 | 0.5 | 0.4 | 9.1 | 5.8 | 5.4 | 9.6 |
| ζ-Carotene (cis/trans isomers) | 377, 399, 425 | nf* | <0.1 | <0.1 | 5.0 | 3.6 | 3.5 | 10.3 |
| Neurosporene | 416, 440, 470 | nr** | <0.1 | <0.1 | <0.1 | <0.1 | <0.1 | <0.1 |
| Lycopene | 447, 472, 504 | nr | <0.1 | <0.1 | <0.1 | <0.1 | <0.1 | <0.1 |
| α-Carotene | 423, 444, 473 | nr | <0.1 | <0.1 | 0.5 | 0.4 | 0.4 | 0.6 |
| β-Carotene | 425, 451, 478 | 0.5 | <0.1 | <0.1 | 0.1 | 0.1 | 0.1 | <0.1 |
| Neoxanthin | 415, 439, 467 | 0.8 | 1.5 | 4.1 | 0.3 | 0.4 | 0.4 | <0.1 |
| Violaxanthin | 419, 440, 470 | nr | | | | | | |
| Antheraxanthin | 422, 444, 472 | 0.1 | 3.1 | 5.5 | 1.7 | 1.9 | 2.2 | 1.9 |
| Lutein | 420, 445, 475 | 72.3 | 84.9 | 81.7 | 61.7 | 70.1 | 71.0 | 52.3 |
| Zeaxanthin | 428, 450, 478 | 16.4 | 4.7 | 5.9 | 2.5 | 2.8 | 3.4 | 1.8 |
| α-Cryptoxanthin | 421, 446, 475 | 0.8 | <0.1 | <0.1 | 0.7 | 0.6 | 0.4 | 0.2 |
| δ-Carotene | 431, 456, 489 | nr | <0.1 | <0.1 | 1.6 | 0.4 | 0.3 | 5.2 |
| β-Cryptoxanthin | 428, 450, 478 | 0.1 | <0.1 | <0.1 | <0.1 | <0.1 | <0.1 | <0.1 |
| β-Zeacarotene | 406, 428, 454 | 0.5 | | | not identified | | | |
| Chrysanthemaxanthin | 400, 421, 448 | 0.8 | <0.1 | <0.1 | <0.1 | 0.1 | 0.1 | <0.1 |
| Flavoxanthin | 400, 421, 448 | 1.4 | | | | | | |
| Auroxanthin | 380, 401, 426 | 0.1 | | | not identified | | | |
| Other compounds that show absorbance at 450 nm | | 0.8 | 5.0 | 2.1 | 4.9 | 3.7 | 4.19 | 4.8 |

*nf = not found
**nr = not reported

EXAMPLE 8

Carotenoid Composition In Leaves of Select Marigolds

Leaves of several marigold plants were assayed for the relative concentration of colored carotenoids present. Leaves from 'Scarletade' and 13819 were used as controls for comparison to leaves from mutant plants. Assays were conducted as in Example 5 and are shown in Tables 7a and 7b, below, where single entries are used for neoxanthin/violaxanthin and chrysanthemaxanthin/flavoxanthin compound pairs that could not be separated. Data in Tables 7a and 7b were collected from different groups of plants grown under different conditions.

TABLE 7a

Relative Percent Distribution of Carotenoids in Leaves of *Tagetes erecta* and Mutants

| Carotenoid | Wavelength in EtOH (nm) | Marigold Selections | | | | | |
|---|---|---|---|---|---|---|---|
| | | 'Scarletade' | 13819 | 124-257 | 119-494 | 117-185 | 086-013 |
| Phytoene | 276, 286, 297 | 0.1 | 0.4 | 0.5 | 0.2 | 0.2 | 0.5 |

TABLE 7a-continued

Relative Percent Distribution of Carotenoids in Leaves of *Tagetes erecta* and Mutants

| Carotenoid | Wavelength in EtOH (nm) | Marigold Selections | | | | | |
|---|---|---|---|---|---|---|---|
| | | 'Scarletade' | 13819 | 124-257 | 119-494 | 117-185 | 086-013 |
| Neoxanthin | 415, 439, 467 | 9.2 | 17.6 | 36.3 | 22.7 | 26.8 | 11.6 |
| Violaxanthin | 419, 440, 470 | | | | | | |
| Antheraxanthin | 422, 444, 472 | 2.8 | 4.3 | 8.4 | 7.7 | 9.1 | 2.9 |
| Lutein | 420, 445, 475 | 44.3 | 37.8 | 0.5 | <0.1 | 1.6 | 34.0 |
| Zeaxanthin | 428, 450, 478 | 6.6 | 3.8 | 4.6 | 27.5 | 10.6 | 4.1 |
| β-Carotene | 425, 451, 478 | 22.6 | 26.5 | 34.1 | 25.0 | 32.7 | 35.8 |
| αCarotene | 423, 444, 473 | 0.5 | 0.3 | <0.1 | <0.1 | <0.1 | 0.2 |
| Chrysanthemaxanthin | 400, 421, 448 | 1.1 | 1.0 | 0.9 | 4.1 | 3.2 | 0.5 |
| Flavoxanthin | 400, 421, 448 | | | | | | |
| Other compounds that show absorbance at 450 nm | | 12.8 | 8.3 | 14.7 | 12.7 | 15.8 | 10.4 |

TABLE 7b

Relative Percent Distribution of Carotenoids in Leaves of *Tagetes erecta* and Mutants

| Carotenoid | Wavelength in EtOH (nm) | Marigold Selections | | | | | |
|---|---|---|---|---|---|---|---|
| | | 'Scarletade' | 100-198 | 100-334 | 100-470 | 101-190 | 114-315 |
| Phytoene | 276, 286, 297 | Inadequate Peak Separation | | | | | |
| Neoxanthin | 415, 439, 467 | 20.4 | <0.1 | 0.3 | <0.1 | 3.1 | <0.1 |
| Violaxanthin | 419, 440, 470 | | | | | | |
| Antheraxanthin | 422, 444, 472 | 1.6 | 1.7 | 1.8 | 1.6 | 5.4 | 1.1 |
| Lutein | 420, 445, 475 | 48.3 | 24.7 | 27.6 | 28.8 | 27.7 | 24.3 |
| Zeaxanthin | 428, 450, 478 | 0.4 | 46.3 | 43.1 | 44.0 | 32.3 | 48.2 |
| β-Carotene | 425, 451, 478 | 15.9 | 14.5 | 17.3 | 14.5 | 19.6 | 13.8 |
| α-Carotene | 423, 444, 473 | <0.1 | <0.1 | <0.1 | <0.1 | <0.1 | <0.1 |
| Chrysanthemaxanthin | 400, 421, 448 | 1.0 | <0.1 | <0.1 | <0.1 | <0.1 | <0.1 |
| Flavoxanthin | 400, 421, 448 | | | | | | |
| β-Cryptoxanthin | 428, 450, 478 | 0.3 | 0.3 | 0.3 | 0.6 | 0.3 | 0.9 |
| Other compounds that show absorbance at 450 nm | | 12.1 | 12.4 | 9.5 | 10.5 | 11.5 | 11.7 |

EXAMPLE 9

Preparation of Marigolds with Little Lutein and High Zeaxanthin, Phytoene, Lycopene or β-Carotene Levels Through Breeding of Mutants Marigold mutant selection 124-257 that exhibits an increased zeaxanthin to lutein ratio compared to wild type was selfed and the resulting seed was maintained. Plants from the selfing of marigold selection 124-257 were used as male parents in a cross with female parent PanAmerican Seed breeding line F9 Ap(85368-4). From this cross, $F_1$ plants were produced and selfed to yield an $F_2$ population.

Fifteen seedlings from the $F_2$ cross were analyzed for the absence of lutein using thin layer chromatography (TLC). Approximately 50 mg of fresh leaf tissue from each seedling was weighed into a 100×13 mm screw top tube containing five glass beads. Sealed vials were stored at −20° C.

For analysis, 500 μl of extractant solvent (10 ml hexane+7 ml acetone+6 ml absolute alcohol+7 ml toluene) were added, and the sealed tubes were vortexed for a minimum of 45 minutes. After vortexing, the solution was transferred to a 4 ml amber vial and evaporated under nitrogen. Samples were resuspended in 125 μl of the above-described extraction solvent and 10 μl were spotted on 19 channel silica gel plates. Plates were dried for approximately 10 minutes then developed for 25 minutes in a two channel 25 cm developing tank containing 100 ml of a 2:1 ethyl acetate: hexane solution. Upon removal, samples were evaluated for the absence of lutein.

From this screen, $F_2$ marigold selection 14649-3 was identified. This selection was used as the female parent in crosses with mutants 101-190 and 100-198, which exhibit an increased zeaxanthin to lutein ratio in addition to having reduced epoxycarotenoid (e.g., neoxanthin and violaxanthin) production compared to wild type.

Marigold mutant selection 100-198 was selfed and the resulting seed was maintained. Plants from the selfing of marigold selection 100-198 were used as the male parent in a cross with the female parent selection 14649-3 described above. From this cross, $F_1$ seeds were collected, and of these 30 seeds were planted. Eleven of the resulting plants were selfed. From this cross, $F_2$ seeds were collected, and 400 of those seeds were planted and grown.

TLC analysis, as described above, was used to analyze leaves of 151 seedlings. Thirty-two plants were identified based on reduced epoxycarotenoid production typical of mutant selection 100-198. The remaining TLC extract was analyzed using high performance liquid chromatography (HPLC), performed using a modified Example 5 protocol. Modifications include the following: dried samples were resuspended into methyl tert-butyl ether and methanol, all gradient conditions used water increased to 6% with a corresponding 1% decrease in methanol, and column temperature was maintained at 25° C.

Analysis confirmed that seven of the 32 plants exhibited an increased zeaxanthin to lutein ratio typical of mutant selection 124-257. Petal and leaf samples of the seven selections were extracted and analyzed according to the protocol in Example 5 with modifications noted above. The results for petals are shown in Table 8a, below, and results for leaves are shown in Table 9a thereafter. In addition, non-saponified petal samples were analyzed to determine the percentage, if any, of non-esterified zeaxanthin. Those data are presented in Table 10.

Marigold mutant selection 101-190 was selfed and the resulting seed was maintained. Marigold selection 101-190 was used as the male parent in a cross with the female parent selection 14649-3 described above. From this cross, $F_1$ seeds were collected and of those seeds, 30 were planted. Six of the resulting plants were selfed. From this latter cross, $F_2$ seeds were collected, planted and grown.

It was determined that the current TLC analysis method was inconclusive for this population. Therefore, approximately 30 plants were selected for HPLC analysis based on having an orange-colored sepal phenotype.

Samples were extracted as for TLC; however, HPLC analysis was conducted. Ten of the 30 selections were found to have reduced epoxy-carotenoid production typical of mutant selection 101-190 in addition to having an increased zeaxanthin to lutein ratio typical of selection 124-257.

Petal and leaf samples of the ten selections were extracted and analyzed according to the protocol in Example 5 with modifications noted above. The results for petals are shown in Tables 8b and 8c, and results for leaves are shown in Tables 9b and 9c. In addition, non-saponified petal samples were analyzed to determine the percentage of non-esterified zeaxanthin. Those data are presented in Table 10.

TABLE 8a

Relative Percent Distribution of Carotenoids
In Petals of *Tagetes erecta* and Mutant Crosses

| Carotenoid | Wavelength in EtOH (nm) | Marigold Selections | | | | | | | | | |
|---|---|---|---|---|---|---|---|---|---|---|---|
| | | 'Scarletade' | 124-257 | 100-198 | 27772-029 | 27772-036 | 27772-100 | 27772-109 | 27772-123 | 27772-130 | 27772-134 |
| Phytoene (isomers) | 276, 286, 297 | 0.5 | 3.9 | 4.5 | 4.9 | 9.2 | 7.0 | 5.1 | 5.6 | 5.7 | 11.7 |
| Phytofluene (isomers) | 331, 348, 367 | 0.7 | 3.6 | 4.4 | 4.6 | 7.2 | 5.7 | 4.6 | 5.3 | 5.0 | 8.2 |
| ζ-Carotene (cis/trans isomers) | 377, 399, 425 | <0.2 | 3.3 | 4.1 | 4.8 | 10.6 | 5.2 | 4.5 | 5.0 | 4.4 | 7.4 |
| Neurosporene | 416, 440, 470 | <0.2 | <0.2 | <0.2 | 0.2 | 0.4 | 0.3 | <0.2 | 0.2 | 0.3 | 0.4 |
| Lycopene | 447, 472, 504 | <0.2 | 0.5 | <0.2 | 0.3 | 1.4 | 0.9 | <0.2 | 0.6 | 0.3 | 0.9 |
| α-Carotene | 423, 444, 473 | <0.2 | <0.2 | 0.4 | <0.2 | <0.2 | <0.2 | <0.2 | <0.2 | <0.2 | <0.2 |
| β-Carotene | 425, 451, 478 | <0.2 | 7.4 | 1.3 | 6.3 | 6.1 | 4.9 | 4.5 | 4.2 | 5.0 | 4.8 |
| Neoxanthin | 415, 439, 467 | 0.5 | 3.4 | <0.2 | <0.2 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 | 0.2 | <0.2 |
| Anthera-xanthin | 422, 444, 472 | 1.6 | 17.5 | 0.6 | 0.5 | 0.4 | 0.6 | 0.5 | 0.5 | 0.7 | 0.3 |
| Lutein | 420, 445, 475 | 91.0 | 2.3 | 68.1 | 0.5 | 0.5 | 0.5 | 0.4 | 0.4 | 0.6 | 0.4 |
| Zeaxanthin | 428, 450, 478 | 3.3 | 29.8 | 14.3 | 73.8 | 60.0 | 70.3 | 76.5 | 74.3 | 72.4 | 62.0 |

TABLE 8a-continued

Relative Percent Distribution of Carotenoids
In Petals of *Tagetes erecta* and Mutant Crosses

| Carotenoid | Wavelength in EtOH (nm) | 'Scarletade' | 124-257 | 100-198 | 27772-029 | 27772-036 | 27772-100 | 27772-109 | 27772-123 | 27772-130 | 27772-134 |
|---|---|---|---|---|---|---|---|---|---|---|---|
| α-Cryptoxanthin | 421, 446, 475 | <0.2 | <0.2 | <0.2 | <0.2 | <0.2 | <0.2 | <0.2 | <0.2 | <0.2 | <0.2 |
| δ-Carotene | 431, 456, 489 | <0.2 | <0.2 | 0.7 | <0.2 | <0.2 | <0.2 | <0.2 | <0.2 | 0.3 | <0.2 |
| β-Cryptoxanthin | 428, 450, 478 | <0.2 | 1.0 | <0.2 | 1.1 | 1.0 | 1.1 | 1.4 | 1.1 | 1.1 | 1.1 |
| β-Zeacarotene | 406, 428, 454 | | | | | not identified | | | | | |
| Chrysanthemaxanthin | 400, 421, 448 | <0.2 | 1.7 | <0.2 | <0.2 | <0.2 | <0.2 | <0.2 | <0.2 | <0.2 | <0.2 |
| Flavoxanthin | 400, 421, 448 | | | | | | | | | | |
| Auroxanthin | 380, 401, 426 | | | | | not identified | | | | | |
| Other compounds that show absorbance at 450 nm | | 1.7 | 12.9 | 1.6 | 2.8 | 3.2 | 3.5 | 2.4 | 2.7 | 4.2 | 2.8 |

TABLE 8b

Relative Percent Distribution of Carotenoids
In Petals of *Tagetes erecta* and Mutant Crosses

| Carotenoid | Wavelength in EtOH (nm) | 'Scarletade' | 124-257 | 101-190 | 27773-006 | 27773-030 | 27773-087 | 27773-107 | 27773-128 |
|---|---|---|---|---|---|---|---|---|---|
| Phytoene (isomers) | 276, 286, 297 | 0.5 | 3.9 | 3.9 | 3.2 | 5.9 | 6.8 | 8.3 | 4.9 |
| Phytofluene (isomers) | 331, 348, 367 | 0.7 | 3.6 | 4.6 | 3.8 | 5.8 | 7.2 | 7.3 | 4.9 |
| ζ-Carotene (cis/trans isomers) | 377, 399, 425 | <0.2 | 3.3 | 5.1 | 4.4 | 5.0 | 10.4 | 8.6 | 5.0 |
| Neurosporene | 416, 440, 470 | <0.2 | <0.2 | <0.2 | <0.2 | 0.2 | <0.2 | <0.2 | <0.2 |
| Lycopene | 447, 472, 504 | <0.2 | 0.5 | <0.2 | 0.2 | 0.4 | 0.8 | <0.2 | 0.4 |
| α-Carotene | 423, 444, 473 | <0.2 | <0.2 | 0.3 | <0.2 | <0.2 | <0.2 | <0.2 | <0.2 |
| β-Carotene | 425, 451, 478 | <0.2 | 7.4 | 1.6 | 9.8 | 8.9 | 11.7 | 8.0 | 7.1 |
| Neoxanthin | 415, 439, 467 | 0.5 | 3.4 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 |
| Antheraxanthin | 422, 444, 472 | 1.6 | 17.5 | 0.6 | 1.9 | 1.8 | 0.9 | 0.8 | 2.1 |
| Lutein | 420, 445, 475 | 91.0 | 2.3 | 63.8 | 0.8 | 0.6 | 0.9 | 0.7 | 0.6 |
| Zeaxanthin | 428, 450, 478 | 3.3 | 29.8 | 16.8 | 69.4 | 67.9 | 58.5 | 62.4 | 70.3 |
| α-Cryptoxanthin | 421, 446, 475 | <0.2 | <0.2 | <0.2 | <0.2 | <0.2 | <0.2 | <0.2 | <0.2 |
| δ-Carotene | 431, 456, 489 | <0.2 | <0.2 | 0.2 | 0.9 | <0.2 | 0.2 | 0.4 | <0.2 |
| β-Cryptoxanthin | 428, 450, 478 | <0.2 | 1.0 | 0.2 | 1.1 | 1.2 | 1.1 | 1.5 | 1.3 |
| β-Zeacarotene | 406, 428, 454 | | | | | not identified | | | |
| Chrysanthemaxanthin | 400, 421, 448 | <0.2 | 1.7 | <0.2 | <0.2 | <0.2 | <0.2 | <0.2 | <0.2 |
| Flavoxanthin | 400, 421, 448 | | | | | | | | |
| Auroxanthin | 380, 401, 426 | | | | | not identified | | | |

TABLE 8b-continued

Relative Percent Distribution of Carotenoids In Petals of *Tagetes erecta* and Mutant Crosses

| Carotenoid | Wavelength in EtOH (nm) | Marigold Selections | | | | | | | |
|---|---|---|---|---|---|---|---|---|---|
| | | 'Scarletade' | 124-257 | 101-190 | 27773-006 | 27773-030 | 27773-087 | 27773-107 | 27773-128 |
| Other compounds that show absorbance at 450 nm | | 1.7 | 12.9 | 2.8 | 4.1 | 2.2 | 1.5 | 1.7 | 3.2 |

TABLE 8c

Relative Percent Distribution of Carotenoids in Petals of *Tagetes erecta* and Mutant Crosses

| Carotenoid | Wavelength in EtOH (nm) | Marigold Selections | | | | | | | |
|---|---|---|---|---|---|---|---|---|---|
| | | 'Scarletade' | 124-257 | 101-190 | 27774-008 | 27774-050 | 27774-064 | 27774-076 | 27774-123 |
| Phytoene (isomers) | 276, 286, 297 | 0.5 | 3.9 | 3.9 | 4.4 | 5.2 | 7.0 | 8.8 | 5.6 |
| Phytofluene (isomers) | 331, 348, 367 | 0.7 | 3.6 | 4.6 | 4.6 | 5.7 | 6.0 | 8.8 | 5.5 |
| ζ-Carotene (cis/trans isomers) | 377, 399, 425 | <0.2 | 3.3 | 5.1 | 4.2 | 8.5 | 6.0 | 9.8 | 5.9 |
| Neurosporene | 416, 440, 470 | <0.2 | <0.2 | <0.2 | 0.2 | <0.2 | 0.3 | 0.3 | <0.2 |
| Lycopene | 447, 472, 504 | <0.2 | 0.5 | <0.2 | 0.4 | 0.6 | 0.4 | 1.5 | 0.2 |
| α-Carotene | 423, 444, 473 | <0.2 | <0.2 | 0.3 | <0.2 | <0.2 | <0.2 | <0.2 | <0.2 |
| β-Carotene | 425, 451, 478 | <0.2 | 7.4 | 1.6 | 7.0 | 9.5 | 5.8 | 9.9 | 10.1 |
| Neoxanthin | 415, 439, 467 | 0.5 | 3.4 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 |
| Antheraxanthin | 422, 444, 472 | 1.6 | 17.5 | 0.6 | 2.5 | <0.2 | 1.5 | 1.9 | 2.5 |
| Lutein | 420, 445, 475 | 91.0 | 2.3 | 63.8 | 0.8 | 0.8 | 0.7 | 0.6 | 0.8 |
| Zeaxanthin | 428, 450, 478 | 3.3 | 29.8 | 16.8 | 71.2 | 66.9 | 67.8 | 54.3 | 64.3 |
| α-Cryptoxanthin | 421, 446, 475 | <0.2 | <0.2 | <0.2 | <0.2 | <0.2 | <0.2 | <0.2 | <0.2 |
| δ-Carotene | 431, 456, 489 | <0.2 | <0.2 | 0.2 | <0.2 | <0.2 | <0.2 | <0.2 | <0.2 |
| β-Cryptoxanthin | 428, 450, 478 | <0.2 | 1.0 | 0.2 | 1.1 | 1.0 | 1.6 | 1.3 | 1.3 |
| β-Zeacarotene | 406, 428, 454 | | | | not identified | | | | |
| Chrysanthemaxanthin | 400, 421, 448 | <0.2 | 1.7 | <0.2 | <0.2 | <0.2 | <0.2 | <0.2 | <0.2 |
| Flavoxanthin | 400, 421, 448 | | | | | | | | |
| Auroxanthin | 380, 401, 426 | | | | not identified | | | | |
| Other compounds that show absorbance at 450 nm | | 1.7 | 12.9 | 2.8 | 3.6 | 1.3 | 2.9 | 2.4 | 3.4 |

TABLE 9a

Relative Percent Distribution of Carotenoids in
Leaves of *Tagetes erecta* and Mutant Crosses

| Carotenoid | Wave-length in EtOH (nm) | Marigold Selections | | | | | | | | | |
|---|---|---|---|---|---|---|---|---|---|---|---|
| | | 'Scarletade' | 124-257 | 100-198 | 27772-029 | 27772-036 | 27772-100 | 27772-109 | 27772-123 | 27772-130 | 27772-134 |
| Phytoene | 276, 286, 297 | Inadequate Peak Separation | | | | | | | | | |
| Neoxanthin | 415, 439, 467 | 9.4 | 9.6 | 0.3 | <0.2 | <0.2 | <0.2 | <0.2 | <0.2 | <0.2 | <0.2 |
| Violaxanthin | 419, 440, 470 | 7.1 | 26.3 | 0.4 | <0.2 | <0.2 | <0.2 | <0.2 | <0.2 | <0.2 | <0.2 |
| Antheraxanthin | 422, 444, 472 | 1.1 | 7.7 | 2.6 | 1.7 | 1.8 | 3.1 | 3.4 | 2.5 | 2.2 | 1.5 |
| Lutein | 420, 445, 475 | 44.7 | 0.4 | 34.8 | <0.2 | <0.2 | <0.2 | <0.2 | <0.2 | <0.2 | <0.2 |
| Zeaxanthin | 428, 450, 478 | 0.3 | 4.8 | 29.6 | 59.1 | 59.9 | 59.0 | 61.4 | 60.4 | 61.1 | 67.0 |
| β-Carotene | 425, 451, 478 | 26.9 | 37.9 | 22.1 | 29.0 | 28.4 | 28.5 | 28.0 | 29.6 | 28.2 | 24.3 |
| α-Carotene | 423, 444, 473 | 0.8 | <0.2 | 0.3 | <0.2 | <0.2 | <0.2 | <0.2 | 1.1 | <0.2 | <0.2 |
| Chrysanthema-xanthin | 400, 421, 448 | 0.7 | 1.5 | <0.2 | <0.2 | 0.6 | 0.4 | <0.2 | <0.2 | <0.2 | <0.2 |
| Flavoxanthin | 400, 421, 448 | | | | | | | | | | |
| β-Crypto-xanthin | 428, 450, 478 | 0.2 | 0.3 | 0.5 | <0.2 | 0.6 | <0.2 | 0.5 | <0.2 | <0.2 | 0.4 |
| Other compounds that show absorbance at 450 nm | | 8.8 | 11.5 | 9.4 | 10.2 | 8.7 | 9.0 | 6.8 | 6.4 | 8.6 | 6.9 |

TABLE 9b

Relative Percent Distribution of Carotenoids in
Leaves of *Tagetes erecta* and Mutant Crosses

| Carotenoid | Wave-length in EtOH (nm) | Marigold Selections | | | | | | | |
|---|---|---|---|---|---|---|---|---|---|
| | | 'Scarletade' | 124-257 | 101-190 | 27773-006 | 27773-030 | 27773-087 | 27773-107 | 27773-128 |
| Phytoene | 276, 286, 297 | Inadequate Peak Separation | | | | | | | |
| Neoxanthin | 415, 439, 467 | 9.4 | 9.6 | 7.6 | 6.2 | 5.0 | 4.6 | 3.7 | 6.9 |
| Violaxanthin | 419, 440, 470 | 7.1 | 26.3 | 3.9 | 2.9 | 1.8 | 1.7 | 0.9 | 4.7 |
| Antheraxanthin | 422, 444, 472 | 1.1 | 7.7 | 7.9 | 8.7 | 8.1 | 6.6 | 6.6 | 13.9 |
| Lutein | 420, 445, 475 | 44.7 | 0.4 | 37.6 | 0.9 | 0.4 | <0.2 | 0.4 | 0.7 |
| Zeaxanthin | 428, 450, 478 | 0.3 | 4.8 | 9.2 | 43.2 | 44.9 | 47.8 | 48.5 | 30.3 |
| β-Carotene | 425, 451, 478 | 26.9 | 37.9 | 25.2 | 30.9 | 32.3 | 31.8 | 31.6 | 32.2 |
| α-Carotene | 423, 444, 473 | 0.8 | <0.2 | 0.5 | <0.2 | <0.2 | <0.2 | <0.2 | <0.2 |
| Chrysanthema-xanthin | 400, 421, 448 | 0.7 | 1.5 | <0.2 | <0.2 | <0.2 | <0.2 | <0.2 | 0.5 |
| Flavoxanthin | 400, 421, 448 | | | | | | | | |
| β-Crypto-xanthin | 428, 450, 478 | 0.2 | 0.3 | <0.2 | <0.2 | <0.2 | <0.2 | <0.2 | 0.7 |
| Other compounds that show absorbance at 450 nm | | 8.8 | 11.5 | 8.1 | 7.3 | 7.6 | 7.5 | 8.3 | 10.2 |

TABLE 9c

Relative Percent Distribution of Carotenoids in Leaves of *Tagetes erecta* and Mutant Crosses

| Carotenoid | Wavelength in EtOH (nm) | Marigold Selections | | | | | | | |
|---|---|---|---|---|---|---|---|---|---|
| | | 'Scarletade' | 124-257 | 101-190 | 27774-008 | 27774-050 | 27774-064 | 27774-076 | 27774-123 |
| Phytoene | 276, 286, 297 | Inadequate Peak Separation | | | | | | | |
| Neoxanthin | 415, 439, 467 | 9.4 | 9.6 | 7.6 | 4.7 | 5.7 | 4.7 | 5.2 | 6.2 |
| Violaxanthin | 419, 440, 470 | 7.1 | 26.3 | 3.9 | 1.4 | 2.9 | 1.6 | 1.7 | 3.3 |
| Antheraxanthin | 422, 444, 472 | 1.1 | 7.7 | 7.9 | 7.4 | 11.4 | 7.2 | 7.8 | 11.7 |
| Lutein | 420, 445, 475 | 44.7 | 0.4 | 37.6 | 1.2 | 0.5 | 0.5 | 0.4 | 0.8 |
| Zeaxanthin | 428, 450, 478 | 0.3 | 4.8 | 9.2 | 48.2 | 41.5 | 49.0 | 48.3 | 40.5 |
| β-Carotene | 425, 451, 478 | 26.9 | 37.9 | 25.2 | 27.5 | 29.9 | 27.4 | 28.4 | 27.2 |
| α-Carotene | 423, 444, 473 | 0.8 | <0.2 | 0.5 | 1.1 | <0.2 | <0.2 | <0.2 | <0.2 |
| Chrysanthemaxanthin | 400, 421, 448 | 0.7 | 1.5 | <0.2 | 0.5 | 0.4 | 0.5 | <0.2 | 0.3 |
| Flavoxanthin | 400, 421, 448 | | | | | | | | |
| β-Cryptoxanthin | 428, 450, 478 | 0.2 | 0.3 | <0.2 | <0.2 | 0.5 | <0.2 | <0.2 | 0.5 |
| Other compounds that show absorbance at 450 nm | | 8.8 | 11.5 | 8.1 | 8.0 | 7.3 | 9.2 | 8.3 | 9.5 |

TABLE 10

Relative Percent Non-esterified Zeaxanthin In Petals of *Tagetes erecta* And Mutant Crosses

| Marigold Selection | % Non-esterified Zeaxanthin |
|---|---|
| 'Scarletade' | 0 |
| 124-257 | 1.1 |
| 100-198 | 2.2 |
| 101-190 | 1.6 |
| 27772-029 | 6.8 |
| 27772-036 | 5.8 |
| 27772-100 | 7.9 |
| 27772-109 | 13.0 |
| 27772-123 | 7.3 |
| 27772-130 | 6.4 |
| 27772-134 | 5.0 |
| 27773-006 | 8.1 |
| 27773-030 | 3.2 |
| 27773-087 | 13.6 |
| 27773-107 | 19.3 |
| 27773-128 | 7.4 |
| 27774-008 | 3.9 |
| 27774-050 | 9.1 |
| 27774-064 | 6.3 |
| 27774-076 | 4.5 |
| 27774-123 | 6.8 |

Mutant selection 119-494 (Table 6a), characterized as having an increased zeaxanthin to lutein ratio compared to wild type, was selfed and the resulting seed was maintained. Mutant selection 115-004 (Table 6c), characterized as having an increased phytoene to lutein ratio compared to wild type, was selfed and the resulting seed was maintained.

The selfed selection 115-004 was used as a female parent in a cross with male parent selfed 119-494. From this cross, $F_1$ plants were produced and selfed to yield an $F_2$ population. $F_2$ plants exhibiting increased lycopene isomer accumulation as compared to wild type *Tagetes erecta* were noted by their red color in a greenhouse planting. Analysis confirmed the lycopene accumulation as well as increased levels of phytoene and β-carotene. Samples were analyzed according to the HPLC protocol outlined above with the exception that a second hexane extraction was not performed. Data from six selections denominated 33457-1, 33458-1, 33459-1, 33456-2, 33458-2 and 33461-1 are reported in Table 11, below.

Additional lycopene, phytoene and β-carotene accumulators were subsequently noted. Selection 27774-105 was from the cross of female parent 14649-3 and male parent 101-190 (Table 8b) described previously in this Example. Petals were analyzed as described above and data are reported in Table 11.

Selection 23012-3 is an $F_3$ plant resulting from the cross of a large-double flower PanAmerican Seed breeding line 85394-2 as the female parent and 124-257 as the male parent. After selfing, an $F_2$ selection characterized as having reduced lutein level was identified by the TLC procedure and the resulting $F_3$ seed was sown in the field located at PanAmerican Seed Santa Paula, Calif. In this population selection 23012-3 was identified by its red colored petals. Petals were analyzed as described above and data are reported in Table 11.

TABLE 11

Relative Percent Distribution of Carotenoids
In Petals of *Tagetes erecta* And Mutants

| Carotenoid | Wavelength in EtOH (nm) | Marigold Selections | | | | | | | | | |
|---|---|---|---|---|---|---|---|---|---|---|---|
| | | 'Scarletade' | 124-257 | 33457-1 | 33458-1 | 33459-1 | 33456-2 | 33458-2 | 33461-1 | 23012-3 | 27774-105 |
| Phytoene (isomers) | 276, 286, 297 | 0.5 | 3.9 | 25.7 | 15.9 | 24.7 | 16.8 | 17.0 | 14.9 | 10.5 | 8.6 |
| Phytofluene (isomers) | 331, 348, 367 | 0.7 | 3.6 | 15.4 | 8.6 | 14.3 | 13.6 | 13.1 | 11.4 | 5.8 | 8.4 |
| ζ-Carotene (cis/trans isomers) | 377, 399, 425 | <0.2 | 3.3 | 10.0 | 5.4 | 10.4 | 10.2 | 10.6 | 8.4 | 6.3 | 4.0 |
| Neurosporene | 416, 440, 470 | <0.2 | <0.2 | <0.2 | <0.2 | <0.2 | <0.2 | <0.2 | <0.2 | <0.2 | <0.2 |
| Lycopene | 447, 472, 504 | <0.2 | 0.5 | 3.5 | 3.2 | 3.9 | 5.6 | 6.3 | 8.5 | 13.6 | 6.8 |
| α-Carotene | 423, 444, 473 | <0.2 | <0.2 | <0.2 | <0.2 | <0.2 | <0.2 | <0.2 | <0.2 | <0.2 | <0.2 |
| β-Carotene | 425, 451, 478 | <0.2 | 7.4 | 3.8 | 3.8 | 3.8 | 16.1 | 12.4 | 9.8 | 9.9 | 10.5 |
| Neoxanthin | 415, 439, 467 | 0.5 | 3.4 | 2.0 | 3.0 | 3.3 | 3.1 | 2.9 | 4.1 | 1.3 | 1.2 |
| Violaxanthin | 419, 440, 470 | 0.7 | 12.7 | 4.4 | 9.6 | 4.4 | 4.0 | 4.7 | 5.4 | 5.9 | 4.0 |
| Antheraxanthin | 422, 444, 472 | 1.6 | 17.5 | 6.7 | 13.7 | 5.7 | 5.6 | 6.2 | 6.7 | 10.4 | 11.3 |
| Lutein | 420, 445, 475 | 91.0 | 2.3 | <0.2 | <0.2 | <0.2 | <0.2 | <0.2 | <0.2 | 2.1 | 1.7 |
| Zeaxanthin | 428, 450, 478 | 3.3 | 29.8 | 14.9 | 23.0 | 10.2 | 11.9 | 12.8 | 18.0 | 18.5 | 32.0 |
| α-Cryptoxanthin | 421, 446, 475 | <0.2 | <0.2 | <0.2 | <0.2 | <0.2 | <0.2 | <0.2 | <0.2 | <0.2 | <0.2 |
| δ-Carotene | 431, 456, 489 | <0.2 | <0.2 | <0.2 | <0.2 | <0.2 | <0.2 | <0.2 | <0.2 | <0.2 | <0.2 |
| β-Cryptoxanthin | 428, 450, 478 | <0.2 | 1.0 | 0.5 | 0.7 | 0.4 | 0.5 | 0.5 | 0.5 | 0.6 | 1.1 |
| β-Zeacarotene | 406, 428, 454 | | | | | not identified | | | | | |
| Chrysanthemaxanthin | 400, 421, 448 | <0.2 | 1.7 | 1.1 | 1.9 | 1.0 | 0.8 | 0.9 | 0.7 | 1.7 | 1.0 |
| Flavoxanthin | 400, 421, 448 | | | | | | | | | | |
| Auroxanthin | 380, 401, 426 | | | | | not identified | | | | | |
| Other compounds that show absorbance at 450 nm | | 1.7 | 12.9 | 12.1 | 11.2 | 17.9 | 11.7 | 12.8 | 11.7 | 13.3 | 9.4 |

\* Certain peaks have not been characterized and a significant number of those listed above as well as other peaks may be lycopene isomers.

EXAMPLE 10

Alternate Methods for Creating Altered Carotenoid Profiles in *Tagetes erecta*

In addition to creating *Tagetes erecta* having altered carotenoid profiles through the use of chemical mutagenesis, alternative methods for providing an altered carotenoid profile can be utilized. Illustrative alternate methods include the use of ionizing radiation and gene silencing using recombinant DNA technology.

More specifically, ionizing radiation has been used to modify gene expression through deletion mutations. Gamma rays have been reported to modify flower color in ornamental species including *Dendranthema*, *Gladiolus* and *Zinnia* [See Datta et al., Zeitschrift fur Pflanzen., 120(1):91–92 (2001); Masakazu, et al., *J. Japanese Soc. For Hort. Sci.*, 70(1):126–128 (2001) and Venkatachalam et al., *Ind. Jour. Gen. & Plant Breed.*, 57(3):255–261 (1997)]. Fast neutrons have been effective in generating deletion mutations in plants. Thus, deletion mutants were obtained for 84% of targeted loci from a mutated Arabidopsis population of 51,840 plants [See Li et al., *The Plant Journal*, 27(3): 235–242(2001).], whereas Love et al., *Amer. Soc. Hort. Sci.*, 88:627–630 (1966) prepared foliage anthocyanin mutations in Coleus. More recently, flower color mutants of Dahlia were reported [See Abe et al., *In Vitro Cell. & Dev. Bio.* 38:93A (2002)].

Gene silencing can also be used to inactivate targeted genes in order to prepare desirable phenotypes such as altered flower pigmentation profiles. Such methods include gene silencing at the transcriptional as well as post-transcriptional level.

Recombinantly-induced, stably integrated transgenes as well as replicating DNA and RNA viruses can mediate silencing events. Transcriptional gene silencing results from the impairment of transcription initiation through promoter methylation and/or chromatin condensation. Homozygous progeny of transgenic petunia containing a transgene for brick-red pelargonidin flower pigmentation unexpectedly yielded a white derivative having a hypermethylated CaMV 35S promoter [See Meyer et al., *Plant Journal* 4(1):89–100 (1993)].

Post-transcriptional gene silencing, in which transcription occurs but RNA fails to accumulate, results from the degradation of mRNA when aberrant sense, antisense, or double-stranded forms of RNA are produced. In petunia, a recombinantly-introduced, transcribed sense transgene encoding for the enzyme chalcone synthase of the flavonoid biosynthetic pathway could down-regulate the expression of homologous endogenous gene and transgene RNA, a phenomenon termed co-suppression. Instead of the expected increased production of the encoded enzyme, 42 percent of the transgenic plants had flowers that were white and/or patterned with white [See Napoli et al., *Plant Cell*, 2(4): 279–289 (1990)].

Before the discovery of co-suppression, down-regulation of endogenous genes was achieved with antisense transgenes. A comparison of sense and antisense chalcone synthase transgenic Petunia identified 75% of the sense transgenics and 82% of the antisense transgenics as having altered flower pigmentation [See Jorgensen et al., *Plant Mol. Biol.*, 31(5):957–973 (1996)].

From double-stranded RNA, small interfering RNAs (siRNA) are processed, and these have been shown to be effective in silencing genes in plants [See Hamilton et al., *Science*, 286(5441):950–952 (1999)]. Intermediates of RNA degradation were identified in co-suppressed petunia plants [See Metzlaff et al., *Cell* 88(6):845–854 (1997)]. Transformation vectors that produced RNAs capable of duplex formation caused specific and heritable genetic interference of four flower- or meristem-related genes in *Arabidopsis thaliana* [See Chuang et al., *Proc. Natl. Acad. Sci.*, 97(9): 4985–4990 (2000)].

In addition, post-transcriptional gene silencing can be accomplished through vectors engineered to express ribozymes capable of cleaving RNA. One class termed 'small ribozymes' includes hairpin ribozyme and hammerhead ribozyme. Efficient gene silencing was also demonstrated in a wide range of plant species using constructs encoding self-complementary hairpin RNA. Intron-containing constructs generally resulted in 90 to 100% of independent transgenics showing gene silencing [See Wesley et al., *Plant Journal*, 27(6):581–590 (2001)]. A transgenic potato plant expressing a hammerhead ribozyme directed against the potato spindle tuber viroid RNA showed high resistance against its replication. This resistance was stably inherited to progeny [See Yang et al., *Proc. Natl. Acad. Sci.*, 94:4861–4865 (1997)].

In the present invention, suitable recombinantly-provided transgenes for gene silencing include expression vectors containing one or more sequence(s) of a *Tagetes* plant encoding enzyme(s) necessary for carotenoid production. Methods of introducing expression vectors into plant tissue include direct gene transfer method such as microprojectile-mediated delivery, DNA injection, electroporation, and the like [See Gruber et al., infra; Miki et al., in *Methods in Plant Molecular Biology and Biotechnology*, Glick et al. eds., CRC Press, Boca Raton, Fla., pages 67–88 (1993); Klein et al., *Biotechnology* 10:268 (1992)]. Expression vectors are also introduced into plant tissues via direct infection or co-cultivation of plant tissue with *Agrobacterium tumefaciens* [See Horsch et al., *Science* 227:1229 (1985)]. Descriptions of *Agrobacterium* vector systems and methods for *Agrobacterium*-mediated gene transfer are provided by Gruber et al., "Vectors for Plant Transformation," in *Methods in Plant Molecular Biology and Biotechnology*, Glick et al. (eds.), pages 89–119 (CRC Press, 1993), Miki et al., supra, and Moloney et al., *Plant Cell Reports* 8:238 (1989).

EXAMPLE 11

Petunias that Have Ketocarotenoids In Their Flower Petals

To determine if ketocarotenoids could be produced in petunia, PanAmerican Seed petunia breeding line 6923-1 was transformed with a LIS1::crtW::nos construct, pBHX586 (Example 2). Transgenic petunia plants were regenerated, and two lines, denominated 586-3401-1-1 and 586-2901-1-1, were evaluated using HPLC analysis. Petal tissue was lyophilized and extracted with the addition of a second hexane extraction according to the official method for extraction of carotenes and xanthophylls in dried plant material (See *Official Methods of Analysis* (1980) 13$^{th}$ Ed., AOAC, Arlington, Va., sec. 43.018–43.023). Tissue was not saponified during extraction.

HPLC equipment comprised a Waters Alliance 2690 equipped with a refrigerated autosampler, Cera 250 column heater/cooler, and a Waters Photodiode Array 996 detector (Waters Corp., Milford, Mass.). Separation was obtained with a YMC30 column, 3 μm, 2.0×150 mm with a guard column of the same material. Standards were obtained from ICC Indofine Chemicals (Somerville, N.J.), Sigma Chemicals (St. Louis, Mo.) and from DHI-Water & Environment (Horsholm, Denmark). Dried samples were resuspended in ethyl acetate and methanol; injections were 10 μl.

Carotenoids were separated using a gradient method. Initial conditions were 91% methanol: 4% water: 5% ethyl acetate (by volume). From zero to 15 minutes the mobile phase was changed from the initial conditions to 81% methanol: 4% water: 15% ethyl acetate, and from 15 to 60 minutes to 21% methanol: 4% water: 75% ethyl acetate. For the following 10 minutes, the mobile phase was returned to the initial conditions and the column equilibrated for an additional 10 minutes. The column temperature was maintained at 15° C. and the flow rate was 0.40 ml/minute throughout.

Values for altered carotenoid profiles of selected mutants are indicated using normalized peak area at 474 nm, and combine suspected isomers of the same compounds. Some compounds may contain minor impurities.

As shown in Table 12 below, transgenic petunia lines 586-3401-1-1 and 586-2901-1-1 contain the ketocarotenoids astaxanthin, adonirubin and canthaxanthin that are not present in control petunia petal tissue.

TABLE 12

Ketocarotenoids in Transgenic Petunia

| Carotenoid normalized peak area 474 nm | Petunia Selections | | |
|---|---|---|---|
| | 6923-1 | 586-2901-1-1 | 586-3401-1-1 |
| Antheraxanthin | 686 | 409 | 343 |
| Astaxanthin | 0 | 176 | 217 |
| Lutein | 7503 | 8954 | 5375 |
| Adonirubin | 0 | 954 | 1604 |
| Zeaxanthin | 2272 | 1708 | 1462 |
| Canthaxanthin | 0 | 2148 | 2926 |
| Beta-Carotene | 5276 | 7559 | 5037 |

Transgenic petunia lines 586-3401-1-1 and 586-2901-1-1 were each used as either the male or female parent for a total of six independent crosses. The other parent in the crosses was selected from an alternate breeding study that used a group of 'Mitchell' petunia lines [Ausubel et al., Plant Mol Biol Rep 1: 26–32 (1980)] transformed with the LIS1::rbcs::crtB::nos (pBHX112) construct. The crtB gene encodes for the enzyme phytoene synthase. In this study, 45 plants were selected for HPLC analysis. The petal tissue extraction procedure, HPLC equipment, and standards used were as noted above.

The dried samples were resuspended in methyl tert-butyl ether and methanol to a total volume of 200 microliters (μl) and filtered. Carotenoids were separated using a gradient method. Initial gradient conditions were 90% methanol: 5% water: 5% methyl tert-butyl ether at a flow rate of 0.4 milliliters per minute. From zero to 15 minutes the mobile phase was changed from the initial conditions to 80 methanol: 5 water: 15 methyl tert-butyl ether, and from 15 to 60 minutes to 20 methanol: 5 water: 75 methyl tert-butyl ether. For the following 10 minutes, the mobile phase was returned to the initial conditions and the column equilibrated for an additional 15 minutes. The column temperature was maintained at 27° C. Injections were 10 μL.

Data for the ten highest β-carotene accumulators are shown in Table 13 below. The carotenoid values are indicated using peak area as percent of the total area at 450 nm. Phytoene was identified based on spectral signature, and phytoene area was determined from a max plot. Data are expressed as normalized peak areas and numbers in parentheses represent the percent each carotenoid compound contributes to the total carotenoid peak areas. An increase in β-carotene levels of about 5- to about 10-fold as compared to the 'Mitchell' control was observed for these transgenic plants. The presence of phytoene was also observed in the transgenic plant petals, with phytoene being undetected in control petal tissue.

TABLE 13

Increased β-carotene in Petunia

| Petunia Selections | Normalized Peak Area | | | |
|---|---|---|---|---|
| | β-Carotene | Phytoene | Zeaxanthin | Lutein |
| 'Mitchell' Control * | 378 (9) | 0 (0) | 398 (10) | 1119 (27) |
| 112A-3200-1-29 | 3962 (48) | 385 (4) | 47 (1) | 1603 (20) |
| 112A-3200-1-31 | 3830 (46) | 2500 (18) | 0 (0) | 1765 (21) |
| 112A-3200-1-43 | 2749 (24) | 375 (2) | 337 (3) | 2939 (26) |
| 112A-3200-1-41 | 2492 (52) | 1536 (18) | 126 (3) | 1168 (24) |
| 112A-3200-1-53 | 2483 (36) | 2159 (17) | 158 (2) | 1557 (23) |
| 112A-3200-1-45 | 2350 (39) | 1331 (15) | 118 (2) | 1701 (28) |
| 112A-3200-1-25 | 2202 (39) | 453 (5) | 191 (3) | 1226 (21) |
| 112A-3200-1-10 | 2055 (25) | 606 (5) | 446 (5) | 2264 (27) |

TABLE 13-continued

Increased β-carotene in Petunia

| Petunia Selections | Normalized Peak Area | | | |
|---|---|---|---|---|
| | β-Carotene | Phytoene | Zeaxanthin | Lutein |
| 112A-3200-1-58 | 1931 (29) | 399 (4) | 304 (5) | 1693 (25) |
| 112A-3200-1-04 | 1797 (38) | 572 (7) | 260 (6) | 1167 (25) |

* Average of 3 injections

In the crtB breeding study, the transformants were crossed with PanAmerican Seed petunia breeding line 6923-1. The resulting plants were selfed, seeds were collected, sown and the resulting plants were grown to maturity and flower. From this population, plants designated 13021-1, 13023-1, 13040-1 and 13041-2 were used as the other parent in the crosses with either 586-3401-1-1 or 586-2901-1-1. From these crosses, seeds were collected, sown and the resulting plants were grown to flowering. From this segregating population, 27 plants were selected for HPLC analysis, based on flower color changes.

Petal tissue was lyophilized and extracted as noted above with the exception that the second hexane extraction was not performed. Carotenoids were separated using a gradient method. Initial conditions were 92% methanol: 3% water: 5% ethyl acetate (by volume). From zero to 13 minutes the mobile phase was held at the initial conditions, and from 13 to 45 minutes to 32% methanol: 3% water: 65% ethyl acetate and held from 45 to 50 minutes. For the following 10 minutes, the mobile phase was returned to the initial conditions and the column equilibrated for an additional 10 minutes. The column temperature was maintained at 15° C. and the flow rate was 0.40 ml/minute throughout.

The transformation source material for lines 586-3401-1-1 and 586-2901-1-1, PanAmerican Seed petunia breeding line 6923-1 was used as a control. In addition, one parent, line 586-3401-1-1, was included in the analysis. As shown in Table 14 below, several petunia lines in the segregating transgenic population contain astaxanthin, adonirubin, and canthaxanthin, which are not present in control petunia petal tissue.

A number of peaks not eluting at the retention times of known standards have UV-Visible spectra clearly indicating that they have one or more 4-keto-β-ionene rings. These have not been fully characterized, but may include 3-hydroxyechinenone, 3'-hydroxyechinenone, and mono- or diesters of astaxanthin, adonirubin, adonixanthin, 3-hydroxyechinenone, and 3'-hydroxyechinenone.

TABLE 14

Ketocarotenoids in Transgenic Petunia

| Petunia Selections | Carotenoid (normalized peak area) | | | | | | | |
|---|---|---|---|---|---|---|---|---|
| | Antheraxanthin | Astaxanthin | Lutein | Adonirubin | Zeaxanthin | Canthaxanthin | Beta-Carotene | Addition Ketocarotenoids |
| 586-3401-1-1** | 995 | 439 | 16962 | 3410 | 2139 | 6368 | 28396 | 5491 |
| 6923-1** | 1325 | 0 | 17915 | 0 | 3597 | 0 | 23107 | nf* |
| 11780-1 | 367 | 0 | 11206 | 0 | 845 | 0 | 34928 | nf |
| 11788-2 | 301 | 474 | 5104 | 2299 | 567 | 4109 | 1938 | 2559 |
| 11788-3 | 800 | 0 | 12350 | 0 | 1581 | 0 | 48262 | nf |
| 11789-1 | 1350 | 0 | 12961 | 0 | 1839 | 0 | 79792 | nf |
| 11789-2 | 1086 | 0 | 12567 | 0 | 1838 | 0 | 7490 | nf |
| 11790-2 | 504 | 1117 | 11527 | 4189 | 1031 | 5941 | 4750 | 9043 |

TABLE 14-continued

Ketocarotenoids in Transgenic Petunia

| Petunia Selections | Antheraxanthin | Astaxanthin | Lutein | Adonirubin | Zeaxanthin | Canthaxanthin | Beta-Carotene | Addition Ketocarotenoids |
|---|---|---|---|---|---|---|---|---|
| 11790-3a | 493 | 1548 | 8424 | 4211 | 1014 | 4762 | 4615 | 10396 |
| 11790-3b | 499 | 957 | 8744 | 3966 | 1115 | 8468 | 6110 | 12800 |
| 11791-1 | 1240 | 0 | 17534 | 0 | 2374 | 0 | 19042 | nf |
| 11791-2 | 833 | 0 | 14068 | 0 | 2021 | 0 | 11450 | nf |
| 11792-1 | 506 | 0 | 10866 | 0 | 967 | 0 | 27538 | nf |
| 11792-3 | 900 | 0 | 19885 | 0 | 1724 | 0 | 66884 | nf |
| 11793-1 | 401 | 1383 | 9018 | 7209 | 670 | 17441 | 33479 | 10755 |
| 11794-1 | 965 | 0 | 12590 | 0 | 1693 | 0 | 41003 | nf |
| 11795-1 | 1376 | 0 | 14720 | 0 | 2129 | 0 | 66331 | nf |
| 11795-3 | 901 | 514 | 10581 | 4218 | 1625 | 12385 | 6869 | 9691 |
| 11796-1 | 950 | 0 | 13755 | 0 | 1883 | 0 | 33373 | nf |
| 11796-2 | 1182 | 0 | 11371 | 0 | 2101 | 0 | 36772 | nf |
| 11797-1 | 678 | 338 | 10993 | 3819 | 1321 | 14536 | 36429 | 5982 |
| 11797-2 | 960 | 458 | 11890 | 3459 | 1729 | 8757 | 33121 | 6202 |
| 11798-1 | 798 | 253 | 12218 | 3050 | 1751 | 9074 | 23863 | 4211 |
| 11798-2 | 743 | 0 | 12671 | 0 | 2216 | 0 | 32206 | nf |
| 11798-4 | 519 | 476 | 8604 | 3786 | 1806 | 8193 | 5238 | 6823 |
| 11798-5 | 516 | 933 | 12397 | 5851 | 1161 | 20570 | 30630 | 8717 |
| 11798-7 | 475 | 205 | 8280 | 2015 | 1127 | 4529 | 3486 | 3834 |
| 11798-8 | 593 | 366 | 10298 | 2974 | 1878 | 7005 | 6084 | 5498 |
| 11799-2 | 640 | 0 | 10652 | 0 | 2310 | 0 | 6203 | nf |

*nf = not found
**Parental line control

PanAmerican Seed breeding line 2088-2 was transformed with a LIS1::AdK6::nos::-LIS1::AdK1::nos construct, pBHX749. From this transformation, one flowering plant was obtained. Using HPLC analysis as described above, the petunia transgenic line was identified as having a carotenoid that has the same retention time as astaxanthin as measured at 450 nm.

EXAMPLE 12

Marigolds that Have Ketocarotenoids in Their Flower Petals

PanAmerican Seed breeding line 13819 was transformed with a LIS1::rbcs::crtW::nos construct, pBHX586, and the resulting transformed plants were grown to maturity and flower. From a population of approximately 200 flowering plants, 26 plants were selected, based on flower color changes, for thin layer chromatography (TLC) screening. Line 13819 was used as a control.

Approximately 100 mg of fresh petal tissue from each mature individual flower was weighed into a 100×13 mm screw top tube containing five glass beads. Sealed vials were stored at −80 C. For analysis, 1 ml of extractant solvent, hexane:acetone:ethanol:toluene, 10:7:6:7 (v:v), was added, and the sealed tubes were vortexed for 1 hour. After vortexing, the solution was transferred to a 4 ml amber vial and evaporated to dryness under nitrogen. The procedure was repeated using 30 minutes of vortexing, and extracts were combined. Samples were resuspended in 125 µl of the above-described extraction solvent and 10 µl were spotted on 19 channel silica gel plates (J. T. Baker, Phillipsburg, N.J.). Plates were dried for approximately 5 minutes then developed for approximately 20 minutes in a two channel 25 cm developing tank containing 100 ml of hexane:acetone, 4:1 (v:v).

The results from the marigold transgenic lines were visually compared for the presence of ketocarotenoids to an Adonis aestivalis reference. Adonis aestivalis is a plant species having deep red flower color due in part to the accumulation of astaxanthin and other ketocarotenoids. Two lines denominated 586-3201-1-12 and 586-3701-1-22A were identified as having ketocarotenoids.

The line 586-3201-1-12 was used as a female parent in a cross with male parent 124-257, a mutant identified in Example 4 as exhibiting an increased zeaxanthin to lutein ratio compared to wild type. Seeds were collected and sown. The resulting 26 plants were grown to full flower.

All plants were heterozygotes; therefore, none had the recessive mutant carotenoid profile. A preliminary TLC screen of the flowers was performed using 124-257 and 13819 as controls and Adonis aestivalis as a ketocarotenoid reference. The screen followed the same procedure reported above with the exceptions of the vortexing being a minimum of 1 hour and 30 minutes and vortexing was not repeated. Six lines designated $F_1$-1 to $F_1$-6 were identified as having ketocarotenoids.

To quantify the ketocarotenoid levels in the transgenics, petals from lines $F_1$-1 to $F_1$-6, 586-3201-1-12 and 586-3701-1-22A and control line 13819 were harvested, lyophilized, and stored under argon at −80 C until analysis. Dried petal material was ground to pass through a No. 40 sieve mesh size, and an accurately weighed 50 mg sample was transferred into a 100×13 mm screw top tube containing five glass beads. Two milliliters of extractant solvent noted above was added, and sealed tubes were vortexed for 1 hour. After vortexing, samples were centrifuged for 5 minutes, the extractant solution transferred to a 4 ml amber vial and evaporated to dryness under nitrogen. This procedure was repeated 3 to 5 times until the extractant solution remained colorless. Dried samples were stored under an argon atmosphere at −80 C.

Using densitometry, samples were quantified relative to an Adonis aestivalis reference curve. For this analysis, samples were resuspended in 1.5 µl of the above-described extraction solvent and vortexed. To produce a reference curve of astaxanthin esters, 10 dilutions from 0.2% to 10.0% were made from the *Adonis aestivalis* extract. Samples were filtered through a cotton plugged five-and-one-half inch Pasteur pipet while being transferred into 2 ml autosampler vials fitted with snap caps.

Using a CAMAG Automatic TLC Sampler 4 (CAMAG Scientific Inc., 515 Cornelius Harnett Drive, Wilmington, N.C. 28401), 6 µl of each sample were spray applied as an 8 mm band to HPTLC silica gel 60 F 254, 20×10 cm plates (E. MERCK KgaA). The plating solvent was evaporated and the plate developed in a CAMAG twin trough chamber. Ten milliliters of hexane:acetone, 4:1 (v:v) were placed in each side of the chamber and the plate developed to 60 mm. After removal, the solvent was evaporated, and the plate was scanned using the CAMAG TLC Scanner 3 and an image of the plate was recorded using the CAMAG Reprostar™ 3.

Absorbances at Rf 0.37, Rf 0.28 and Rf 0.54 correlated to spectral signatures of astaxanthin, adonirubin and adonixanthin, respectively, in the Adonis extracts. In marigold samples, the absorbance at Rf 0.38 correlated to the astaxanthin spectral signature. The differences are believed to be due to the addition of alternate fatty acid moieties. Values for astaxanthin and adonirubin were calculated as a percent of the Adonis aestivalis reference. Data are presented in Table 15 below. The minor absorbance detected for control 13819 did not correlate to a ketocarotenoid compound. In all transgenics tested, the values for adonixanthin were higher than the Adonis aestivalis reference. From the calculated absorbances, the plants having the three highest observed values are $F_1$-3, 586-3201-1-12, and $F_1$-5, in order from highest to lowest.

TABLE 15

Ketocarotenoids in Transgenic Marigold

| Selection | Astaxanthin (% of Adonis) | Adonirubin (% of Adonis) |
|---|---|---|
| 13819 | <0.45 | not detected |
| 586-3201-1-12 | 2.04 | 6.7 |
| 586-3701-1-22A | 1.22 | 4.1 |
| $F_1$-1 | 1.74 | 5.9 |
| $F_1$-2 | 1.71 | 5.3 |
| $F_1$-3 | 2.11 | 6.0 |
| $F_1$-4 | 1.44 | 4.8 |
| $F_1$-5 | 2.09 | 7.0 |
| $F_1$-6 | 1.23 | 5.4 |

The plants $F_1$-1 to $F_1$-6, analyzed above, were used as females in independent backcrosses with male parent 124-257, a mutant identified in Example 4. Seeds were collected and sown. Plants were grown to full flower and transgene segregation in both the carotenoid mutant and the wild-type profiles were identified.

Fifty-nine plants including both mutant and wild-type carotenoid profiles were evaluated using the same densitometry procedure as stated above with the exception that before filtration, 150 µl were removed from the 1.5 ml reconstituted sample. Data for the highest 20 ketocarotenoid producers are presented below in Table 16. It should be noted, that the two highest astaxanthin producers were from plants having a mutant 124-257 profile of increased zeaxanthin to lutein ratio. As reported above, the values for adonixanthin were higher in all transgenics tested than the Adonis aestivalis reference. From the calculated absorbances, the plants having the three highest observed values are $F_2$#3-4, $F_2$#1-37 and $F_2$#1-20, in order from highest to lowest.

TABLE 16

Ketocarotenoids in Transgenic Marigold

| Selection | Astaxanthin (% of Adonis) | Adonirubin (% of Adonis) |
|---|---|---|
| $F_2$#1–20* | 4.1 | >7.7 |
| $F_2$#3–4* | 3.5 | 6.5 |
| $F_2$#3–2 | 3.1 | 5.6 |
| $F_2$#1–18 | 3.1 | 6.0 |
| $F_2$#6–19 | 2.9 | 7.0 |
| $F_2$#1–37 | 2.9 | >7.7 |
| $F_2$#3–1* | 2.8 | 5.0 |
| $F_2$#1–30* | 2.8 | 4.9 |
| $F_2$#3–31* | 2.7 | 5.2 |
| $F_2$#2–34 | 2.5 | 7.2 |
| $F_2$#1–27 | 2.4 | 5.3 |
| $F_2$#1–23 | 2.4 | 4.4 |
| $F_2$#2–24 | 2.4 | 5.3 |
| $F_2$#5–17 | 2.4 | 5.0 |
| $F_2$#3–38 | 2.4 | 4.4 |
| $F_2$#5–25* | 2.3 | >7.7 |
| $F_2$#1–22* | 2.3 | >7.7 |
| $F_2$#2–35 | 2.3 | 4.2 |
| $F_2$#3–41 | 2.3 | 5.2 |
| $F_2$#1–9 | 2.2 | 5.0 |

*mutant carotenoid profile

PanAmerican Seed breeding line 13819 was transformed with a LIS1::AdK6::nos construct, pBHX701, and the resulting transformed plants were grown to maturity and flower. The AdK6 sequence codes for a transit peptide as well as the ketolase. From a population of 61 flowering plants, 1 of these, line 701-2502-1-35, was selected based on flower color changes for thin layer chromatography (TLC) screening. The screen followed the same non-quantitative procedure reported above with the exceptions of the vortexing being a minimum of 1 hour and 30 minutes and vortexing was not repeated. Line 13819 was used as a control. The marigold transgenic line was identified as having ketocarotenoids based on the visual comparison to an *Adonis aestivalis* ketocarotenoid reference.

EXAMPLE 14

Particle Bombardment Transformation of Petunias with Carotenoid Transgenes

To further examine ketocarotenoid production in petunia, Easy Wave™ white, commercially available from PanAmerican Seed Co., 622 Town Road, West Chicago, Ill. 60185, was transformed with either plasmid pBHX689 UBQ3::nptII::LIS1::rbcs::crtB::nos::UBQ3::rbcs::crtI::nos or plasmid pBHX691 UBQ3::nptII::LIS::rbcs::crtW::nos::UBQ3::rbcs::crtZ::nos. The transformation system was particle bombardment of leaf-derived protoplasts. Techniques for petunia protoplast isolation and regeneration are well known in the art [See Binding, *Mongr Theor Appl Genet*, 9:123–132 (1984).]

In the present study, greenhouse-grown leaves three-fourths to fully expanded were selected for protoplast isolation. Prior to protoplast isolation, whole leaves were surface sterilized for approximately 12 minutes in a 12% Clorox® solution containing a few drops of Tween® 20. After surface sterilization, the leaves were rinsed four times with sterile distilled water. Leaves were then cut into approximately 0.2–0.5 mm strips, transferred to approximately 25 ml of a plasmolysis solution and allowed to incubate for approximately 40 minutes. The plasmolysis solution contained 13 grams of mannitol dissolved in 100 ml of a salt solution, designated CPW, that itself contained 0.272 mg/l $KH_2PO_4$, 1.01 mg/l KNO3, 2.46 mg/l $MgSO_4 \cdot 5H_2O$, 0.0016 mg/l KI, 0.00025 mg/l $CuSO_4 \cdot 2H_2O$, and 148.0 mg/l $CaCl_2 \cdot 2H_2O$. For the plasmolysis solution, the pH value was adjusted to 5.7 before autoclave sterilization.

After incubation, the plasmolysis solution was removed and replaced with a digestion enzyme solution. The digestion enzyme solution contained 500 mg cellulase R10 (Yakuit Honsha Co., Tokyo, Japan) and 100 mg macerase (CalBiochem, La Jolla, Calif.) dissolved in 100 ml CPW salt solution, as noted above, and the pH value adjusted to 5.7 before filter sterilization. The tissues were put on an oscillating shaker and incubated for approximately 14 hours.

The protoplasts were then transferred to a 50 ml conical centrifuge tube and pelleted via centrifugation at 45×g for 10 minutes, after which they were washed with a protoplast wash medium. The protoplast wash medium consisted of Murashige and Skoog basal salt medium without nitrogen, M531 (PhytoTechnology Laboratories LLC, Shawnee Mission, Kans.), with the following additives: 1.9 g/l KNO3, 100 mg/l glutamine, 20 mg/l casein hydrolysate, 10 mg/l thiamine HCl, 2 mg/l glycine, 0.5 mg/l nicotinic acid, 0.1 mg/l serine, 2 g/l myo-inositol, and 90 g/l sorbitol. The medium pH value was adjusted to 5.7 before autoclave sterilization.

For purification, the protoplasts were pelleted and re-suspended in 5 ml of the protoplast wash medium noted above and layered over 7 ml of a density gradient solution contained in a 15 ml conical centrifuge tube. The density gradient was prepared by dissolving 8.56 g of sucrose in 50 ml of the CPW salt solution noted above and 25 ml of histopaque (Sigma Chemical Co., St. Louis, Mo.). The pH value of the density gradient was adjusted to 5.7 before filter sterilization. The mixture was spun at 95×g for 12 minutes and protoplasts were collected at the interface.

Following purification, the protoplasts were pelleted and re-suspended in a modified Kao and Michayluk liquid medium consisting of K427 (PhytoTechnology Laboratories LLC, Shawnee Mission, Kans.) with the following additives: 250 mg/l casein hydrolysate, 20 ml/l coconut milk, 17.1 g/l sucrose, 63.8 g/l mannitol, 2 g/l myo-inositol, 1 mg/l 2,4-dichlorophenoxyacetic acid, 1 mg/l 1-naphthaleneacetic acid, and 0.5 mg/l 6-benzylaminopurine.

The medium pH value was adjusted to 5.7 before filter sterilization. The protoplast suspension was then plated onto a modified Murashige and Skoog solid medium containing M531, above, with the following additives: 1.9 g/l KN03, 100 mg/l glutamine, 20 mg/l casein hydrolysate, 10 mg/l thiamine HCl, 2 mg/l glycine, 0.5 mg/l nicotinic acid, 0.1 mg/l serine, 2 g/l myo-inositol, 17.1 g/l sucrose, 31.9 g/l mannitol, 31.5 g/l glucose, 1 mg/l 2,4-dichlorophenoxyacetic acid, 1 mg/l 1-naphthaleneacetic acid, and 0.5 mg/l 6-benzylaminopurine. The medium pH value was adjusted to 5.7 before the addition of 5 g/l washed agar and autoclave sterilization.

For culture, approximately 4 ml of the modified Kao and Michayluk liquid medium described above was layered on top of the modified Murashige and Skoog solid medium described above, and then approximately 1 ml of protoplast suspension was gently transferred to the liquid medium. Cultured cells were then placed in dark culture conditions at approximately 23–24° C. Approximately 8 to 10 days after initial culture, protoplast-derived cells were plated onto a modified Kao and Michayluk solid medium consisting of K427 with the following additives: 250 mg/l casein hydrolysate, 20 ml/l coconut milk, 103 g/l sucrose, 2 g/l myo-inositol, 1 mg/l 1-naphthaleneacetic acid, and 0.5 mg/l 6-benzylaminopurine. The medium pH value was adjusted to 5.7 before the addition of 5 g/l purified agar (Sigma Chemical Co., St. Louis, Mo.) and autoclave sterilization.

Three days after plating onto solid medium, cultures were bombarded using a Biolistic® Particle Delivery System, model PDS 1000 (Bio-Rad Laboratories, Hercules, Calif.). Bombardment conditions included a 900 psi rupture disk, 9 cm distance between the stopping screen to culture surface, and approximately 800 ng DNA vector per bombardment coated onto 0.6 µm gold particles.

Two bombardment treatments were performed per culture plate. Immediately after bombardment, plates were placed in dark conditions at approximately 23–24° C. for 48 hours. After this time, cultures were transferred to the modified Kao and Michayluk solid medium described above with the sucrose reduced to 80 g/l, the agar increased to 7 g/l, and the addition of 100 mg/l kanamycin that was filter sterilized. After an additional 8 to 14 days, cultures were transferred to a regeneration medium containing 100 mg/l kanamycin that was filter sterilized. The regeneration with the following additives: 30 g/l sucrose, 0.5 mg/l 6-benzylaminopurine, and 1 mg/l indole-3-acetic acid. The medium pH value was adjusted to 5.7 before the addition of 8 g/l agar and autoclave sterilization. Developing colonies were subcultured to the regeneration medium containing 100 mg/l kanamycin every 3 to 4 weeks until shoots were regenerated. Rooted plants were established and grown to flower in the greenhouse.

Using the plasmid pBHX689 construct, having the genes crtB encoding phytoene synthase (that makes phytoene from geranylgeranyl pyrophosphate) and crtI encoding for phytoene desaturase (that converts phytoene into lycopene), 225 plants were established in the greenhouse. Of these plants, 5 had a visible phenotype that included an orange coloration in the throat of the flower. Based on previous work, this phenotype is known to be associated with an increase in β-carotene. Ketocarotenoid production was not anticipated with this construct.

Using the plasmid pBHX691 construct, having the genes crtW β-carotene ketolase (that converts a carotenoid β-ionene ring that is unsubstituted at the 4-position as is present in β-carotene into a carotenoid having a β-ionene ring with a 4-keto group), and crtZ for β-carotene hydroxylase (that converts a carotenoid β-ionene ring that is unsubstituted at the 3-position into a carotenoid having a β-ionene ring with a 3-hydroxy group), 219 plants were established in the greenhouse. None of these plants exhibited phenotypic evidence of ketocarotenoid production. While not wishing to be bound by any theory, it is believed that these results reflect the limited substrate β-carotene availability in this set of plants studied.

Each of the patents and articles cited herein is incorporated by reference. The use of the article "a" or "an" is intended to include one or more. The contents of co-owned application Ser. No. xxxx filed on this date and having the title "Plant Expression Cassette" are also hereby incorporated by reference.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

SEQUENCE LISTING

<160> NUMBER OF SEQ ID NOS: 24

<210> SEQ ID NO 1
<211> LENGTH: 28
<212> TYPE: DNA
<213> ORGANISM: Artificial Sequence
<220> FEATURE:
<223> OTHER INFORMATION: Primer used to introduce a Kpn I restriction site at the 3' end of the B-carotene ketolase gene (crtW) from Haematococcus pluvialis.

<400> SEQUENCE: 1
gccagtgcca aggtacctct gtcatgcc                                      28

<210> SEQ ID NO 2
<211> LENGTH: 28
<212> TYPE: DNA
<213> ORGANISM: Artificial Sequence
<220> FEATURE:
<223> OTHER INFORMATION: Primer used to introduce a Nde I restriction site at the 5' end of the B-carotene ketolase gene (crtW) from Haematococcus pluvialis.

<400> SEQUENCE: 2
ccggggatcc tctacatatg cacgtcgc                                      28

<210> SEQ ID NO 3
<211> LENGTH: 30
<212> TYPE: DNA
<213> ORGANISM: Artificial Sequence
<220> FEATURE:
<223> OTHER INFORMATION: Primer used to introduce an Xma I restriction site at the 5' end of the transit peptide from the Nicotiana tabacum ribulose biosphosphate carboxylase small subunit.

<400> SEQUENCE: 3
ctcgtcgacc cgggatggct tcctcagttc                                    30

<210> SEQ ID NO 4
<211> LENGTH: 30
<212> TYPE: DNA
<213> ORGANISM: Artificial Sequence
<220> FEATURE:
<223> OTHER INFORMATION: Primer used to introduce a Nde I restriction site at the 3' end of the transit peptide from the Nicotiana tabacum ribulose biosphosphate carboxylase small subunit.

<400> SEQUENCE: 4
cccatatgtt gcactcttcc gccgttgctg                                    30

<210> SEQ ID NO 5
<211> LENGTH: 37
<212> TYPE: DNA
<213> ORGANISM: Artificial Sequence
<220> FEATURE:
<223> OTHER INFORMATION: Primer used to introduce a Hind III site and Sal I site at the 5' end of the ubiquitin 3 (UBQ3) gene promoter from Arabidopsis thaliana.

<400> SEQUENCE: 5
acaagctttc agagtcgact tcggatttgg agccaag                            37

<210> SEQ ID NO 6
<211> LENGTH: 28
<212> TYPE: DNA
<213> ORGANISM: Artificial Sequence

```
<220> FEATURE:
<223> OTHER INFORMATION: Primer used to introduce an Xma I site a
      the 3' end of the ubiquitin 3 (UBQ3) gene promoter from
      Arabidopsis thaliana.

<400> SEQUENCE: 6
tcatccccgg gatgtgaaag agagagtc                                    28

<210> SEQ ID NO 7
<211> LENGTH: 30
<212> TYPE: DNA
<213> ORGANISM: Artificial Sequence
<220> FEATURE:
<223> OTHER INFORMATION: Primer used to introduce a Hind III site at
      the 5' end of the upstream (promoter) region of the ubiquitin 11
      (UBQ11) gene from Arabidopsis thaliana.

<400> SEQUENCE: 7
caaagcttca gactagtcga cttgcctcaa                                  30

<210> SEQ ID NO 8
<211> LENGTH: 30
<212> TYPE: DNA
<213> ORGANISM: Artificial Sequence
<220> FEATURE:
<223> OTHER INFORMATION: Primer used to introduce an Xma I site at the
      3' end of the upstream (promoter) region of the ubiquitin 11
      (UBQ11) gene from Arabidopsis thaliana.

<400> SEQUENCE: 8
caattcgatg gggcccggga tcttgatcac                                  30

<210> SEQ ID NO 9
<211> LENGTH: 24
<212> TYPE: DNA
<213> ORGANISM: Artificial Sequence
<220> FEATURE:
<223> OTHER INFORMATION: Primer used to introduce a Kpn I restriction
      site at the 3' end of the Haematococcus pluvialis gene.

<400> SEQUENCE: 9
ccagtgccaa gctggtaccg tcat                                        24

<210> SEQ ID NO 10
<211> LENGTH: 26
<212> TYPE: DNA
<213> ORGANISM: Artificial Sequence
<220> FEATURE:
<223> OTHER INFORMATION: Primer used to introduce a Nde I restriction
      site at the 5' end of the Haematococcus pluvialis gene.

<400> SEQUENCE: 10
ggggatcctc tacatatgag cgcaca                                      26

<210> SEQ ID NO 11
<211> LENGTH: 29
<212> TYPE: DNA
<213> ORGANISM: Artificial Sequence
<220> FEATURE:
<223> OTHER INFORMATION: Primer used to synthesize an about 1kb fragment
      containing the LIS1 5'-flanking region of the Clarkia brewerii LIS1
      gene.

<400> SEQUENCE: 11
ccaagcttat ctaataatgt atcaaaatc                                   29

<210> SEQ ID NO 12
```

```
<211> LENGTH: 31
<212> TYPE: DNA
<213> ORGANISM: Artificial Sequence
<220> FEATURE:
<223> OTHER INFORMATION: Primer used to synthesize an about 1kb fragment
      containing the LIS1 5'-flanking region of the Clarkia breweri LIS1
      gene.

<400> SEQUENCE: 12
cagcccggga tggttgtctt gtttaaggtg g                                    31

<210> SEQ ID NO 13
<211> LENGTH: 29
<212> TYPE: DNA
<213> ORGANISM: Artificial Sequence
<220> FEATURE:
<223> OTHER INFORMATION: Primer used to introduce a Hind III site at the
      5' end to prepare a Hind III - EcoR I fragment consisting of the
      promoter-containing region of the Clarkia breweri LIS1 gene.

<400> SEQUENCE: 13
ccaagcttat ctaataatgt atcaaaatc                                       29

<210> SEQ ID NO 14
<211> LENGTH: 31
<212> TYPE: DNA
<213> ORGANISM: Artificial Sequence
<220> FEATURE:
<223> OTHER INFORMATION: Primer used to introduce a Sma I site at the
      3' end to prepare a Hind III - EcoR I fragment consisting of the
      promoter-containing region of the Clarkia breweri LIS1 gene.

<400> SEQUENCE: 14
cagcccggga tggttgtctt gtttaaggtg g                                    31

<210> SEQ ID NO 15
<211> LENGTH: 38
<212> TYPE: DNA
<213> ORGANISM: Artificial Sequence
<220> FEATURE:
<223> OTHER INFORMATION: Primer used to add a Hind III and a Mfe I site
      to the 5' end of the neomycin phosphotransferase II selectable
      marker gene.

<400> SEQUENCE: 15
gcacaagctt tggatcgcaa ttgatgattg aacaagat                             38

<210> SEQ ID NO 16
<211> LENGTH: 32
<212> TYPE: DNA
<213> ORGANISM: Artificial Sequence
<220> FEATURE:
<223> OTHER INFORMATION: Primer used to add a Kpn I site to the 3' end
      of the neomycin phosphotransferase II selectable marker gene.

<400> SEQUENCE: 16
cccaggtacc cgctcagaag aactcgtcaa ga                                   32

<210> SEQ ID NO 17
<211> LENGTH: 24
<212> TYPE: DNA
<213> ORGANISM: Artificial Sequence
<220> FEATURE:
<223> OTHER INFORMATION: Primer used to add a Pme III site to prepare
      the multi-cloning site from pUC19.

<400> SEQUENCE: 17
cacgtttaaa ctaccgcaca gatg                                            24
```

<210> SEQ ID NO 18
<211> LENGTH: 20
<212> TYPE: DNA
<213> ORGANISM: Artificial Sequence
<220> FEATURE:
<223> OTHER INFORMATION: Primer used to retain the Hind III site to
      prepare the multi-cloning site from pUC19.

<400> SEQUENCE: 18
ggccgcatac aggctgtcag                                                 20

<210> SEQ ID NO 19
<211> LENGTH: 30
<212> TYPE: DNA
<213> ORGANISM: Artificial Sequence
<220> FEATURE:
<223> OTHER INFORMATION: Primer used to add a Nde I site to the 5' end
      of the E. uredovora crtZ gene.

<400> SEQUENCE: 19
cggggatcct ctacatatga ccaatttcct                                      30

<210> SEQ ID NO 20
<211> LENGTH: 30
<212> TYPE: DNA
<213> ORGANISM: Artificial Sequence
<220> FEATURE:
<223> OTHER INFORMATION: Primer used to add a Kpn I site to the 3' end
      of the E. uredovora crtZ gene.

<400> SEQUENCE: 20
cgacggccgg taccaagcta gatctgtcac                                      30

<210> SEQ ID NO 21
<211> LENGTH: 28
<212> TYPE: DNA
<213> ORGANISM: Artificial Sequence
<220> FEATURE:
<223> OTHER INFORMATION: Primer used to add a Nde I site to the 5' end
      of A. aestivalis genomic DNA to prepare Adonis aestivalis
      ketolase genes.

<400> SEQUENCE: 21
gaaacctcat atggcagcag caatttca                                        28

<210> SEQ ID NO 22
<211> LENGTH: 32
<212> TYPE: DNA
<213> ORGANISM: Artificial Sequence
<220> FEATURE:
<223> OTHER INFORMATION: Primer used to add a Kpn I site to the 3' end
      of A. aestivalis genomic DNA to prepare Adonis aestivalis ketolase
      genes.

<400> SEQUENCE: 22
cacggtacct tcaggtagat ggttgcgttc gt                                   32

<210> SEQ ID NO 23
<211> LENGTH: 24
<212> TYPE: DNA
<213> ORGANISM: Artificial Sequence
<220> FEATURE:
<223> OTHER INFORMATION: One of an anneled pair of oligonucleotides
      used to prepare the plasmid pBHX612

<400> SEQUENCE: 23

```
ggccgcaagc ttgaggaggt cgac                                          24

<210> SEQ ID NO 24
<211> LENGTH: 24
<212> TYPE: DNA
<213> ORGANISM: Artificial Sequence
<220> FEATURE:
<223> OTHER INFORMATION: One of an anneled pair of oligonucleotides
      used to prepare the plasmid pBHX612

<400> SEQUENCE: 24
agctgtcgac ctcctcaagc ttgc                                          24
```

What is claimed:

1. A transgenic *Tagetes erecta* marigold plant or a regenerable portion thereof whose genome contains a transgene that encodes a chimeric ketolase enzyme polypeptide having two portions, (i) an N-terminal first portion comprising a plastid transit peptide portion fused to (ii) a second ketolase enzyme portion that converts a carotenoid β-ionene ring into a 4-keto-β-ionene ring, said transgene being operatively linked to a promoter that controls expression of said transgene, wherein the flower petals of said transgenic plant accumulate a carotenoid compound having a 4-keto-β-ionene ring, and wherein the flower petals of a host *Tagetes erecta* marigold that is not transformed with said chimeric ketolase, produce a carotenoid compound that contains a β-ionene ring having an unsubstituted 4-position and contains lutein that contains an β-ionene ring; and wherein said carotenoid compound produced in the petals of said host marigold contains a β-ionene ring having an unsubstituted 4-position that is one or both of β-carotene and zeaxanthin, and the ratio of the amount of β-carotene to the sum of the amounts of β-carotene and lutein present in said host flower petals is greater than about 1:10 or the ratio of the amount of zeaxanthin to the sum of the amounts of zeaxanthin and lutein present in said host flower petals is greater than about 1:10.

2. The *Tagetes erecta* marigold plant or a regenerable portion thereof according to claim 1 wherein said carotenoid compound having a 4-keto-β-ionene ring is a 4,4'-diketo-β-ionene ring carotenoid compound.

3. The *Tagetes erecta* marigold plant or a regenerable portion thereof according to claim 1 wherein said 4,4'-diketo-β-ionene ring carotenoid compound is canthaxanthin.

4. The *Tagetes erecta* marigold plant or a regenerable portion thereof according to claim 1 wherein said 4,4'-diketo-β-ionene ring carotenoid compound is astaxanthin.

5. The *Tagetes erecta* marigold plant or a regenerable portion thereof according to claim 1 wherein said plastid transit peptide portion is the RUBISCO transit peptide.

6. The *Tagetes erecta* marigold plant or a regenerable portion thereof according to claim 1 whose genome includes a second transgene that encodes a second chimeric polypeptide that contains (i) an N-terminal plastid transit peptide fused to (ii) a hydroxylase enzyme that converts a carotenoid β-ionene ring compound into a carotenoid 3-hydroxy-β-ionene ring compound, and said second transgene is operatively linked to a promoter that controls expression of said second transgene.

7. The *Tagetes erecta* marigold plant or a regenerable portion thereof according to claim 6 wherein said carotenoid compound having a 3-hydroxyl-β-ionene ring is a 3,3'-dihydroxy-β-ionene ring carotenoid compound.

8. The *Tagetes erecta* marigold plant or a regenerable portion thereof according to claim 7 wherein said 3,3'-dihydroxy-β-ionene ring carotenoid compound is zeaxanthin.

9. The *Tagetes erecta* marigold plant or a regenerable portion thereof according to claim 6 wherein said plastid transit peptide portion is the RUBISCO transit peptide.

10. The *Tagetes erecta* marigold plant or a regenerable portion thereof according to claim 1 wherein said ketolase enzyme portion that converts a carotenoid β-ionene ring into a carotenoid 4keto-β-ionene ring is a β-carotene-4oxygenase that is encoded by a gene present in one or more organisms selected from the group consisting of *Adonis aestivalis*, *Agrobacterium aurantiacum*, *Alcaligenes* sp., *Bradyrhizobium* sp., *Brevundimonas aurantiaca*, *Haematococcus pluvialis*, *Nostoc* sp., *Paracoccus marcusii*, *Xanthophyllomyces dendrorhous*, *Synechocystis* sp., *Therrnosynechococcus elongates*, and *Trichodesmium erythraeum*.

11. The *Tagetes erecta* marigold plant or a regenerable portion thereof according to claim 1 wherein said ketolase enzyme portion that converts a carotenoid 62 -ionene ring into a carotenoid 4-keto-β-ionene ring is encoded by the crtW gene of *Agrobacterium aurantiacum*.

12. The plant according to claim 1 wherein said ketolase enzyme portion that converts a carotenoid β-ionene ring into a carotenoid 4-keto-β-ionene ring is encoded by one or both of the AdK1 gene and AdK6 gene of *Adonis aestivalis*.

13. The *Tagetes erecta* marigold plant or a regenerable portion thereof according to claim 1 wherein said ketolase enzyme portion that converts a carotenoid β-ionene ring into a carotenoid 4-keto-β-ionene ring is encoded by the crtW gene of *Alcaligenes* sp.PC-1.

14. The *Tagetes erecta* marigold plant or a regenerable portion thereof according to claim 7 wherein said hydroxylase enzyme portion that converts a carotenoid β-ionene ring into a carotenoid 3-hydroxy-β-ionene ring is encoded by one or both of the crtZ genes of *Erwinia uredovora* and *Erwinia herbicola*.

15. The *Tagetes erecta* marigold plant or a regenerable portion thereof according to claim 1 wherein said promoter that controls expression of said transgene is a flower petal-preferred promoter.

16. The *Tagetes erecta* marigold plant or a regenerable portion thereof according to claim 1 wherein the carotenoid compound that contains a β-ionene ring having an unsubstituted 4-position produced in the flower petals of a plant of the same type that is not transformed with said chimeric ketolase is one or both of β-carotene and zeaxanthin.

17. The *Tagetes erecta* marigold plant or a regenerable portion thereof according to claim 16 wherein said plant of the same type that is not transformed with said chimeric ketolase is transformed with one or more DNA segments that encode one or more carotenoid-forming enzymes other than a ketolase.

18. The *Tagetes erecta* marigold plant or a regenerable portion thereof according to claim 1 that further includes one or more further transgenes selected from the group consisting of the (a) crtE, crtB, crtI, crtY and crtZ genes of *Erwinia uredovora* or (b) GGPP synthase, phytoene synthase, phytoene dehydrogenase(4H), lycopene cyclase, and β-carotene hydroxylase genes of *Erwinia herbicola*, wherein each of said further transgenes (i) is operatively linked to a promoter that directs flower petal-preferred expression of said transgene, and (ii) expresses a chimeric polypeptide enzyme that contains an N-terminal plastid transit peptide portion.

\* \* \* \* \*